United States Patent
Witty et al.

(10) Patent No.: US 9,045,485 B2
(45) Date of Patent: Jun. 2, 2015

(54) ASK 1 INHIBITING PYRROLOPYRIMIDINE DERIVATIVES

(75) Inventors: David R. Witty, Cambridge (GB); David Norton, Cambridge (GB); Jason Paul Tierney, Cambridge (GB); Ghislaine Lorthioir, Cambridge (GB); Mairi Sime, Cambridge (GB); Karen Louise Philpott, Cambridge (GB)

(73) Assignee: CONVERGENCE PHARMACEUTICALS LIMITED, London (GB)

(*) Notice: Subject to any disclaimer, the term of this patent is extended or adjusted under 35 U.S.C. 154(b) by 33 days.

(21) Appl. No.: 13/994,691

(22) PCT Filed: Dec. 15, 2011

(86) PCT No.: PCT/GB2011/052484
§ 371 (c)(1),
(2), (4) Date: Oct. 21, 2013

(87) PCT Pub. No.: WO2012/080735
PCT Pub. Date: Jun. 21, 2012

(65) Prior Publication Data
US 2014/0038957 A1    Feb. 6, 2014

Related U.S. Application Data

(60) Provisional application No. 61/423,865, filed on Dec. 16, 2010.

(51) Int. Cl.
| | |
|---|---|
| C07D 401/04 | (2006.01) |
| C07D 401/14 | (2006.01) |
| C07D 487/04 | (2006.01) |
| A61K 31/4523 | (2006.01) |
| A61K 31/519 | (2006.01) |
| A61P 19/02 | (2006.01) |

(52) U.S. Cl.
CPC .......... *C07D 487/04* (2013.01); *A61K 31/4523* (2013.01); *C07D 401/04* (2013.01); *C07D 401/14* (2013.01); *A61K 31/519* (2013.01)

(58) Field of Classification Search
CPC .. C07D 401/04; C07D 401/14; C07D 487/04; A61K 31/4523; A61K 31/519
USPC ........................................ 544/280; 514/265.1
See application file for complete search history.

(56) References Cited

U.S. PATENT DOCUMENTS

| | | | | |
|---|---|---|---|---|
| 7,582,643 | B2 * | 9/2009 | Blake et al. | 514/264.11 |
| 7,902,373 | B2 * | 3/2011 | Blake et al. | 546/300 |
| 8,067,589 | B2 * | 11/2011 | Blake et al. | 544/224 |
| 2009/0264450 | A1 | 10/2009 | Burgoon et al. | |

FOREIGN PATENT DOCUMENTS

| | | |
|---|---|---|
| EP | 2058309 | 5/2009 |
| WO | WO91/04254 | 4/1991 |
| WO | WO99/62518 | 12/1999 |
| WO | WO01/39777 | 6/2001 |
| WO | WO2004/014850 | 2/2004 |
| WO | WO2004/048565 | 6/2004 |
| WO | WO2005/117909 | 12/2005 |
| WO | WO2007/125310 | 11/2007 |
| WO | WO2007/125321 | 11/2007 |
| WO | WO2008/016131 | 2/2008 |
| WO | WO2008/075109 | 6/2008 |
| WO | WO2008/075110 | 6/2008 |
| WO | WO2008/075172 | 6/2008 |
| WO | WO2009/027283 | 3/2009 |
| WO | WO2009/047563 | 4/2009 |
| WO | WO2009/123986 | 10/2009 |
| WO | WO2010/080996 | 7/2010 |

OTHER PUBLICATIONS

Shiizaki et al., Advances in Biological Regulation 53 (2013) 135-144.*
Cecil Textbook of Medicine, edited by Bennet, J.C., and Plum F., 20th edition, vol. 1, 1004-101 O, 1996.*
Mass, R. D., Int. J. Radiation Oncology Bio. Phys.vol. 58(3): 932-940, 2004.*
Fabbro et al. Pharmacology & therapeutics 93, 79-98, 2002.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p. 4.*
Dermer et al., Bio/Technology, 1994, 12:320.*

* cited by examiner

*Primary Examiner* — Venkataraman Balasubramanian
(74) *Attorney, Agent, or Firm* — Foley & Lardner LLP

(57) ABSTRACT

This invention relates to pyrrolopyrimidine derivatives of formula (I): where $R_1$, X, p, $R_4$, $R_2$ and $R_3$ are as defined herein, and their use as pharmaceuticals.

(I)

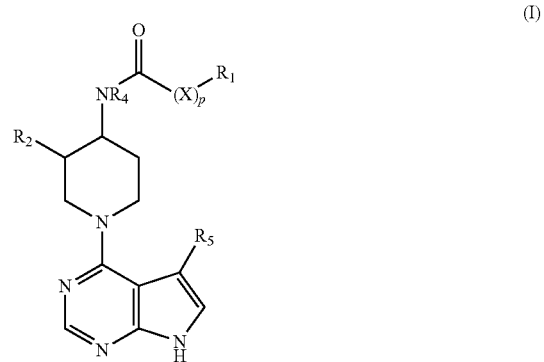

17 Claims, 2 Drawing Sheets

ASK 1 INHIBITING PYRROLOPYRIMIDINE DERIVATIVES

CROSS-REFERENCE TO RELATED APPLICATIONS

This application is the U.S. national stage application of International Patent Application No. PCT/GB2011/052484, filed on Dec. 15, 2011, which claims priority to U.S. Provisional Application No. 61/423,865, filed on Dec. 16, 2010, each of which is incorporated herein by reference in its entirety.

This invention relates to pyrrolopyrimidine derivatives and their use as pharmaceuticals.

Apoptosis signal-regulating kinase (ASK1) is a ubiquitously expressed Ser/Thr kinase on the mitogen-activated protein kinase (MAPK) signalling pathway inducing response to stress stimuli including proinflammatory molecules such as tumor necrosis factor-α (TNF-α) and lipopolysaccharide (LPS), endoplasmic stress, oxidative stress, genotoxic stress, free radicals, Fas ligand and calcium overload (Takeda K et al (2008) Annu Rev Pharacol Toxicol 248 pp 199-225; Nagai H et al (2007) J Biochem Mol Biol 40 pp 1-6).

ASK1 is one of a number of MAP kinase kinase kinases (MAP3Ks) which signal through MAP kinase kinases (MKKs). In the case of ASK1 signalling, MKK3 and MKK6 activate the p38 pathway and MKK4 and MKK7 activate the JNK pathway (Davis R J (2000) Cell 103 pp 239-252; Ichijo H et al (1997) Science 275 pp 90-94). Therefore inhibitors of ASK1 have the potential to suppress signalling pathways through both p38 and JNK.

The use of soluble TNF receptor: Fc fusion protein Enbrel (etanercept) has been shown to be efficacious in the clinic for inflammatory pain and also in pre-clinical models for neuropathic pain (Hao S et al (2007) Gene Therapy 14 pp 1010-1016) implying that TNF-α is a key mediator in pain response. IL-6 is a key downstream mediator of TNF-α signalling and there is clinical evidence supporting anti-IL-6 therapy as a valid therapeutic approach for rheumatoid arthritis (Roche has published positive Phase III results for Actemra/Tocilizumab in May 2008).

A number of cells that do not have functional ASK1 (isolated from ASK1 knockout mice, or following gene silencing) are resistant to TNF-α induced apoptosis (Tobiume K, et al (2001) EMBO Rep 2 pp 222-228). ASK1 is therefore pivotal in the TNF-α pathway and supports the hypothesis that disrupting the TNF-α signalling pathway via ASK1 inhibition would lead to beneficial downstream effects such as relief from pain. There is strong evidence to link activation of p38 and/or JNK with the production of pro-inflammatory mediators and subsequent pain response (Ji R-R and Suter M R (2007) Molecular Pain 3 pp 33-41; Cheng H T et al (2008) Neuroscience 155 pp 948-958; Ji R-R and Gao Y-J (2008) Neurosci Lett 437 pp 180-183). As ASK1 activation can lead to the activation of both p38 and JNK, inhibition of ASK1 has the potential to be more powerful than p38 inhibitors alone and, as it is higher up in the signalling cascade, may limit the likelihood of unwanted liabilities.

WO08/016,131 discloses fused heterocyclic ASK1 inhibitors for use in the treatment of diabetes and inflammatory disease. WO04/048565 describes a novel peptide which has ASK1 activity which may be useful in the treatment of cancer and degenerative diseases. WO2009/123986 and WO2009/027283 both describe ASK1 inhibitors.

The present invention describes a series of pyrrolopyrimidine derivatives which are inhibitors of the ASK1 kinase and which may be useful in the prevention or treatment of diseases and disorders where an inhibitor of ASK1 is required for example pain or inflammation.

Accordingly the present invention provides a compound of formula (I)

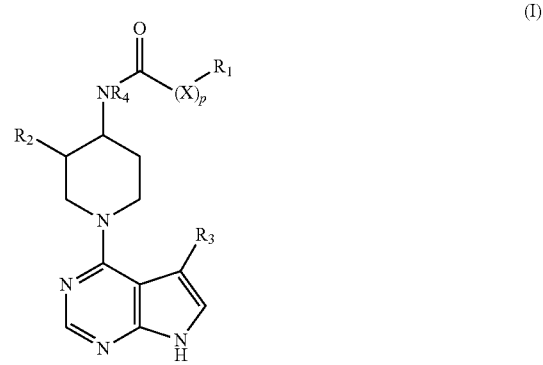

where
X is $(CH_2)_m$ or $CH_2O$, where m is 1 or 2;
p is 0 or 1;
$R_1$ is phenyl or a 5 or 6 membered heteroaryl group selected from the group consisting of imidazolyl, isoxazolyl, pyridinyl, pyridazinyl or pyrimidinyl, which phenyl or heteroaryl group is optionally substituted with 1 or 2 substituents selected from the group consisting of $(C_{1-4})$alkyl, $(C_{1-4})$alkoxy, halo, $(CH_2)_2NR_5R_6$ where $R_5$ and $R_6$ are independently H or $(C_{1-4})$alkyl and n is 0 or 1, pyrrolidinyl, morpholinyl, piperidinyl, pyrrolidin$(C_{1-4})$alkyl, morpholin$(C_{1-4})$alkyl, piperidin$(C_{1-4})$alkyl, pyrrolidin$(C_{1-4})$alkoxy, morpholin$(C_{1-4})$alkoxy, piperidin$(C_{1-4})$alkoxy wherein said pyrrolidinyl, morpholinyl or piperidinyl groups are optionally substituted with halo or $(C_{1-4})$alkyl, with the proviso that when $R_1$ is phenyl or a 6 membered heteroaryl group, which phenyl or 6 membered heteroaryl group has a substitutent on the atom at the para position, said substituent is selected from the group consisting of methyl, ethyl, isopropyl, methoxy, halo or $(CH_2)_nNR_5R_6$ where $R_5$ and $R_6$ are methyl;
$R_2$ is H, methoxy, ethoxy or $CH_2OCH_3$;
$R_3$ is H, $(C_{1-4})$alkyl, $(C_{2-4})$alkenyl, halo, cyano, furanyl or pyrazolyl, which pyrazolyl is optionally substituted with 1 methyl group;
$R_4$ is H or $(C_{1-4})$alkyl;
or a pharmaceutically acceptable salt thereof.

In one embodiment $R_1$ is unsubstituted phenyl or an unsubstituted 5 or 6 membered heteroaryl group selected from the group consisting of imidazolyl, isoxazolyl, pyridinyl, pyridazinyl or pyrimidinyl.

In one embodiment $R_1$ is unsubstituted phenyl. In an alternative embodiment $R_1$ is phenyl which is substituted at the 2 and 6 positions with methyl.

In one embodiment p is 0.
In one embodiment p is 1.
In one embodiment p is 1 and X is methyl or methoxy.
In one embodiment p is 1 and $R_1$ is unsubstituted phenyl.
In one embodiment $R_1$ is phenyl substituted with $(C_{1-4})$alkyl or $(C_{1-4})$alkoxy. In another embodiment $R_1$ is phenyl optionally substituted with methyl or methoxy.

In one embodiment $R_1$ is phenyl substituted with $(CH_2)_nNR_5R_6$ where $R_5$ and $R_6$ are independently H and n is 0 or 1.

In one embodiment $R_1$ is phenyl substituted with pyrrolidinyl, morpholinyl, piperidinyl, pyrrolidin($C_{1-4}$)alkyl, morpholin($C_{1-4}$)alkyl, piperidin($C_{1-4}$)alkyl, pyrrolidin($C_{1-4}$)alkoxy, morpholin($C_{1-4}$)alkoxy, piperidin($C_{1-4}$)alkoxy, halopyrrolidinylethoxy or dihalopyrrolidinylethoxy. In another embodiment $R_1$ is phenyl substituted with pyrrolidinylethoxy, morpholinylmethoxy, fluoropyrrolidinylethoxy or difluorpyrrolidinylethoxy.

In one embodiment $R_1$ is pyridinyl substituted with ($C_{1-4}$)alkyl or ($C_{1-4}$)alkoxy. In another embodiment $R_1$ is pyridinyl optionally substituted with methyl or methoxy.

In one embodiment $R_1$ is isoxazolyl substituted with 1 or 2 ($C_{1-4}$)alkyl groups. In another embodiment $R_1$ is isoxazolyl substituted with 1 or 2 methyl groups.

In one embodiment $R_1$ is imidazolyl substituted with 1 or 2 ($C_{1-4}$)alkyl groups. In another embodiment $R_1$ is imidazolyl substituted with 1 or 2 methyl groups In one embodiment $R_4$ is H. In another embodiment $R_4$ is methyl.

In one embodiment $R_2$ is H.

In one embodiment $R_3$ is methyl.

In one embodiment $R_2$ is methoxy or methoxymethyl.

In one embodiment $R_1$ is phenyl, $R_2$ is H and $R_3$ is methyl. In a further embodiment, $R_1$ is phenyl, $R_2$ is H, $R_3$ is methyl, $R_4$ is H and p is 0.

For the avoidance of doubt the substituent pyrrolidin($C_{1-4}$)alkyl or pyrrolidin($C_{1-4}$)alkoxy groups, and the morpholinyl and piperidinyl equivalents thereof, are attached to the phenyl or heteroaryl via the alkyl or alkoxy moiety.

When the compound contains a ($C_{1-4}$)alkyl group, whether alone or forming part of a larger group, e.g. ($C_{1-4}$)alkoxy, the alkyl group may be straight chain, branched or cyclic, or combinations thereof. Examples of ($C_{1-4}$)alkyl are methyl or ethyl. An example of a branched alkyl group is methylethyl. An example of a cyclic alkyl is cyclopropyl. An example of ($C_1$-4)alkoxy is methoxy.

Examples of ($C_{1-4}$)alkoxy include methoxy and ethoxy.

Examples of ($C_{2-4}$)alkenyl include ethenyl and n-propenyl.

Halogen or "halo" means fluoro, chloro, bromo or iodo.

It is to be understood that the present invention covers all combinations of particularised groups and substituents described herein above.

In one embodiment the invention provides the compound of formula (I) selected from the group consisting of:
N-[1-(7H-Pyrrolo[2,3-d]pyrimidin-4-yl)-4-piperidinyl]benzamide;
3-(Methyloxy)-N-[1-(1H-pyrrolo[2,3-d]pyrimidin-4-yl)-4-piperidinyl]benzamide;
3-(Dimethylamino)-N-[1-(1H-pyrrolo[2,3-d]pyrimidin-4-yl)-4-piperidinyl]benzamide;
4-(Dimethylamino)-N-[1-(1H-pyrrolo[2,3-d]pyrimidin-4-yl)-4-piperidinyl]benzamide;
2-(Dimethylamino)-N-[1-(1H-pyrrolo[2,3-d]pyrimidin-4-yl)-4-piperidinyl]benzamide;
3-[(Dimethylamino)methyl]-N-[1-(1H-pyrrolo[2,3-d]pyrimidin-4-yl)-4-piperidinyl]benzamide;
3-(1-Pyrrolidinyl)-N-[1-(1H-pyrrolo[2,3-d]pyrimidin-4-yl)-4-piperidinyl]benzamide;
3-(4-Morpholinyl)-N-[1-(1H-pyrrolo[2,3-d]pyrimidin-4-yl)-4-piperidinyl]benzamide;
N-[1-(1H-Pyrrolo[2,3-d]pyrimidin-4-yl)-4-piperidinyl]-2-pyridinecarboxamide;
N-[1-(1H-Pyrrolo[2,3-d]pyrimidin-4-yl)-4-piperidinyl]-3-pyridinecarboxamide;
N-[1-(1H-Pyrrolo[2,3-d]pyrimidin-4-yl)-4-piperidinyl]-4-pyridinecarboxamide;
2-Methyl-N-[1-(1H-pyrrolo[2,3-d]pyrimidin-4-yl)-4-piperidinyl]-4-pyridinecarboxamide;
N-[1-(1H-Pyrrolo[2,3-d]pyrimidin-4-yl)-4-piperidinyl]-4-pyridazinecarboxamide;
N-[1-(1H-Pyrrolo[2,3-d]pyrimidin-4-yl)-4-piperidinyl]-5-pyrimidinecarboxamide;
2-(Methyloxy)-N-[1-(1H-pyrrolo[2,3-d]pyrimidin-4-yl)-4-piperidinyl]-4-pyridinecarboxamide;
5-Methyl-N-[1-(1H-pyrrolo[2,3-d]pyrimidin-4-yl)-4-piperidinyl]-3-isoxazolecarboxamide;
N-[1-(5-Methyl-1H-pyrrolo[2,3-d]pyrimidin-4-yl)-4-piperidinyl]benzamide;
N-[1-(5-Ethyl-1H-pyrrolo[2,3-d]pyrimidin-4-yl)-4-piperidinyl]benzamide;
N-{1-[5-(1-Methylethenyl)-1H-pyrrolo[2,3-d]pyrimidin-4-yl]-4-piperidinyl}benzamide;
N-{1-[5-(1-Methylethyl)-1H-pyrrolo[2,3-d]pyrimidin-4-yl]-4-piperidinyl}benzamide;
N-[1-(5-Methyl-1H-pyrrolo[2,3-d]pyrimidin-4-yl)-4-piperidinyl]-2-pyridinecarboxamide;
6-Methyl-N-[1-(5-methyl-1H-pyrrolo[2,3-d]pyrimidin-4-yl)-4-piperidinyl]-3-pyridinecarboxamide;
2-(Methyloxy)-N-[1-(5-methyl-1H-pyrrolo[2,3-d]pyrimidin-4-yl)-4-piperidinyl]-4-pyridinecarboxamide;
3-(Methyloxy)-N-[1-(5-methyl-1H-pyrrolo[2,3-d]pyrimidin-4-yl)-4-piperidinyl]benzamide;
2-Methyl-N-[1-(5-methyl-7H-pyrrolo[2,3-d]pyrimidin-4-yl)-4-piperidinyl]-4-pyridinecarboxamide;
2-Methyl-N-[1-(5-methyl-7H-pyrrolo[2,3-d]pyrimidin-4-yl)-4-piperidinyl]benzamide;
N-[1-(5-methyl-7H-pyrrolo[2,3-d]pyrimidin-4-yl)-4-piperidinyl]-4-pyridinecarboxamide;
3,5-dimethyl-N-[1-(5-methyl-7H-pyrrolo[2,3-d]pyrimidin-4-yl)-4-piperidinyl]-4-isoxazolecarboxamide;
N-[1-(5-bromo-7H-pyrrolo[2,3-d]pyrimidin-4-yl)-4-piperidinyl]benzamide;
N-methyl-N-[1-(7H-pyrrolo[2,3-d]pyrimidin-4-yl)-4-piperidinyl]benzamide;
2,6-dimethyl-N-[1-(5-methyl-7H-pyrrolo[2,3-d]pyrimidin-4-yl)-4-piperidinyl]benzamide;
N-methyl-N-[1-(5-methyl-7H-pyrrolo[2,3-d]pyrimidin-4-yl)-4-piperidinyl]benzamide;
1-methyl-N-[1-(5-methyl-7H-pyrrolo[2,3-d]pyrimidin-4-yl)-4-piperidinyl]-1H-imidazole-5-carboxamide;
N-[3-(methyloxy)-1-(5-methyl-7H-pyrrolo[2,3-d]pyrimidin-4-yl)-4-piperidinyl]benzamide;
N-methyl-N-[1-(5-methyl-7H-pyrrolo[2,3-d]pyrimidin-4-yl)-4-piperidinyl]-4-pyridinecarboxamide;
N-[1-(5-bromo-7H-pyrrolo[2,3-d]pyrimidin-4-yl)-4-piperidinyl]-N-methyl-4-pyridinecarboxamide;
N-{1-[5-(1-methyl-1H-pyrazol-4-yl)-1H-pyrrolo[2,3-d]pyrimidin-4-yl]-4-piperidinyl}benzamide;
N-{1-[5-(3-furanyl)-1H-pyrrolo[2,3-d]pyrimidin-4-yl]-4-piperidinyl}benzamide;
N-[3-[(methyloxy)methyl]-1-(5-methyl-7H-pyrrolo[2,3-d]pyrimidin-4-yl)-4-piperidinyl]benzamide;
N-[1-(5-methyl-7H-pyrrolo[2,3-d]pyrimidin-4-yl)-4-piperidinyl]-3-{[2-(1-pyrrolidinyl)ethyl]oxy}benzamide;
N-[1-(5-chloro-1H-pyrrolo[2,3-d]pyrimidin-4-yl)-4-piperidinyl]benzamide;
N-[1-(5-cyano-1H-pyrrolo[2,3-d]pyrimidin-4-yl)-4-piperidinyl]benzamide;

N-[1-(5-methyl-1H-pyrrolo[2,3-d]pyrimidin-4-yl)-4-piperidinyl]-3-{[2-(4-morpholinypethyl]oxy}benzamide;

3-({2-[(3R)-3-fluoro-1-pyrrolidinyl]ethyl}oxy)-N-[1-(5-methyl-1H-pyrrolo[2,3-d]pyrimidin-4-yl)-4-piperidinyl]benzamide;

3-{[2-(3,3-difluoro-1-pyrrolidinyl)ethyl]oxy}-N-[1-(5-methyl-1H-pyrrolo[2,3-d]pyrimidin-4-yl)-4-piperidinyl]benzamide;

3-({2-[(2R)-2-methyl-1-pyrrolidinyl]ethyl}oxy)-N-[1-(5-methyl-7H-pyrrolo[2,3-d]pyrimidin-4-yl)-4-piperidinyl]benzamide;

2-(phenyloxy)-N-[1-(7H-pyrrolo[2,3-d]pyrimidin-4-yl)-4-piperidinyl]acetamide; and 2-phenyl-N-[1-(7H-pyrrolo[2,3-d]pyrimidin-4-yl)-4-piperidinyl]acetamide, or a pharmaceutically acceptable salt thereof.

In a further embodiment the invention provides the compound of formula (I) which is N-[1-(5-Methyl-1H-pyrrolo[2,3-d]pyrimidin-4-yl)-4-piperidinyl]benzamide (E17) or a pharmaceutically acceptable salt thereof.

It will be appreciated that for use in medicine the salts of the compounds of formula (I) should be pharmaceutically acceptable. Suitable pharmaceutically acceptable salts will be apparent to those skilled in the art. Pharmaceutically acceptable salts include those described by Berge, Bighley and Monkhouse J Pharm Sci (1977) 66 pp 1-19. Such pharmaceutically acceptable salts include acid addition salts formed with inorganic acids e.g. hydrochloric, hydrobromic, sulphuric, nitric or phosphoric acid and organic acids e.g. succinic, maleic, acetic, fumaric, citric, tartaric, benzoic, p-toluenesulfonic, methanesulfonic or naphthalenesulfonic acid. Other salts e.g. oxalates or formates, may be used, for example in the isolation of compounds of formula (I) and are included within the scope of this invention.

Certain of the compounds of formula (I) may form acid addition salts with one or more equivalents of the acid. The present invention includes within its scope all possible stoichiometric and non-stoichiometric forms.

The compounds of formula (I) may be prepared in crystalline or non-crystalline form and, if crystalline, may optionally be solvated, eg. as the hydrate. This invention includes within its scope stoichiometric solvates (eg. hydrates) as well as compounds containing variable amounts of solvent (eg. water).

It will be understood that the invention includes pharmaceutically acceptable derivatives of compounds of formula (I) and that these are included within the scope of the invention.

As used herein "pharmaceutically acceptable derivative" includes any pharmaceutically acceptable ester or salt of such ester of a compound of formula (I) which, upon administration to the recipient is capable of providing (directly or indirectly) a compound of formula (I) or an active metabolite or residue thereof.

The compounds of formula (I) may be achiral or R or S enantiomers. Where additional chiral centres are present in compounds of formula (I), the present invention includes within its scope all possible enantiomers and diastereoisomers, including mixtures thereof. The different isomeric forms may be separated or resolved one from the other by conventional methods, or any given isomer may be obtained by conventional synthetic methods or by stereospecific or asymmetric syntheses. The invention also extends to any tautomeric forms or mixtures thereof.

The subject invention also includes isotopically-labeled compounds which are identical to those recited in formula (I) but for the fact that one or more atoms are replaced by an atom having an atomic mass or mass number different from the atomic mass or mass number most commonly found in nature. Examples of isotopes that can be incorporated into compounds of the invention include isotopes of hydrogen, carbon, nitrogen, oxygen, fluorine, iodine and chlorine such as $^3H$, $^{11}C$, $^{14}C$, $^{18}F$, $^{123}I$ or $^{125}I$.

Compounds of the present invention and pharmaceutically acceptable salts of said compounds that contain the aforementioned isotopes and/or other isotopes of other atoms are within the scope of the present invention. Isotopically labeled compounds of the present invention, for example those into which radioactive isotopes such as $^3H$ or $^{14}C$ have been incorporated, are useful in drug and/or substrate tissue distribution assays. Tritiated, ie. $^3H$, and carbon-14, ie. $^{14}C$, isotopes are particularly preferred for their ease of preparation and detectability. $^{11}C$ and $^{18}F$ isotopes are particularly useful in PET (positron emission tomography).

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are given on a weight for weight basis). Impure preparations of the compounds may be used for preparing the more pure forms used in the pharmaceutical compositions.

SCHEMES

According to a further aspect of the present invention there is provided a process for the preparation of compounds of formula (I) and derivatives thereof. The following schemes, schemes 1 to 13, are examples of synthetic schemes that may be used to synthesise the compounds of the invention. In the following schemes reactive groups can be protected with protecting groups and deprotected according to well established techniques.

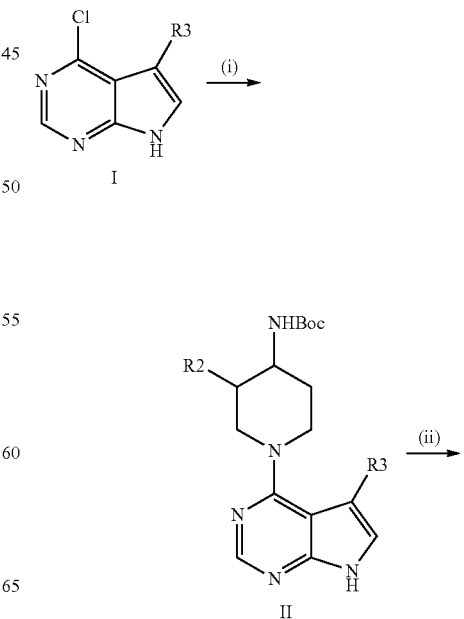

Scheme 1

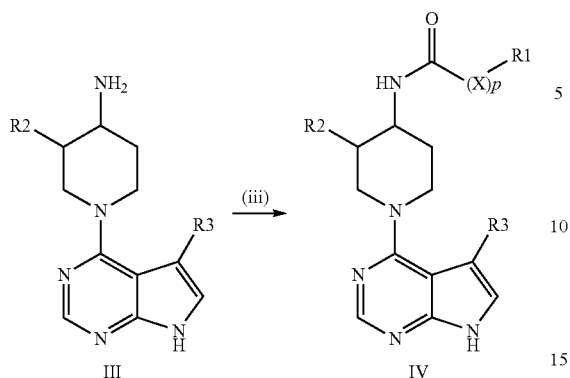

(i) Condition A: EtOH, 130° C.; condition B: DIPEA, DMP, 150° C.
(ii) Condition A: TFA, RT; condition B: 4M HCl in dioxane, RT
(iii) Condition A: R1(X)pCOCl, N-methylmorpholine, DMF, RT; condition B: R1(X)pCO2H, HATU, HOAt, DIPEA, DMF, RT; condition C: R1(X)pCO2H, EDC, HOAt, DIPEA, DMF, RT; condition D: R1(X)pCO2H, EDC, HOBt, DIPEA, DCM, RT; condition E: R1(X)pCOCl, PS-morpholine, DMF, RT; condition F: R1(X)pCOCl, DIPEA, DCM, RT Scheme 2

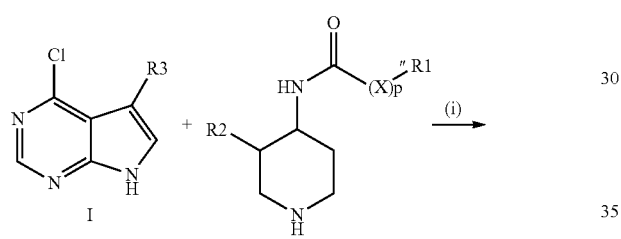

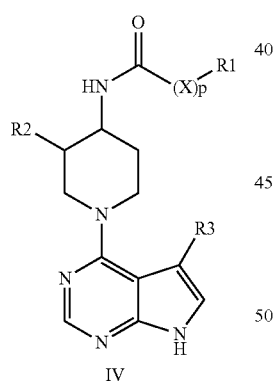

i) Condition A: EtOH, 130-150° C.; condition B: DIPEA, NMP, 150-180° C.

Scheme 3

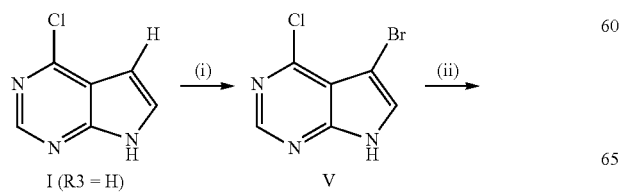

(R3 = Me)

(i) NBS, DMF, RT
(ii) 2.5M nBuLi, CH3—I, THF, -78° C.

Scheme 4

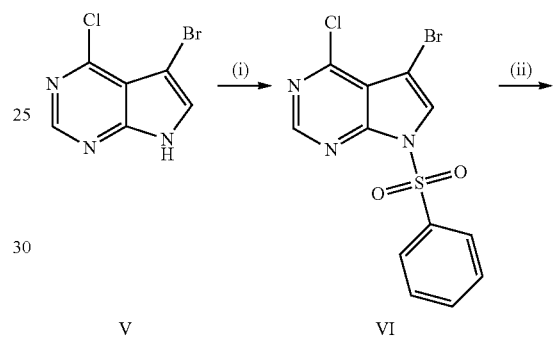

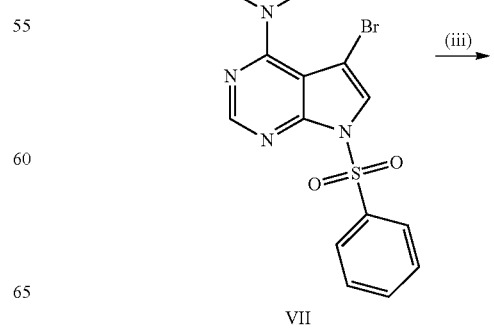

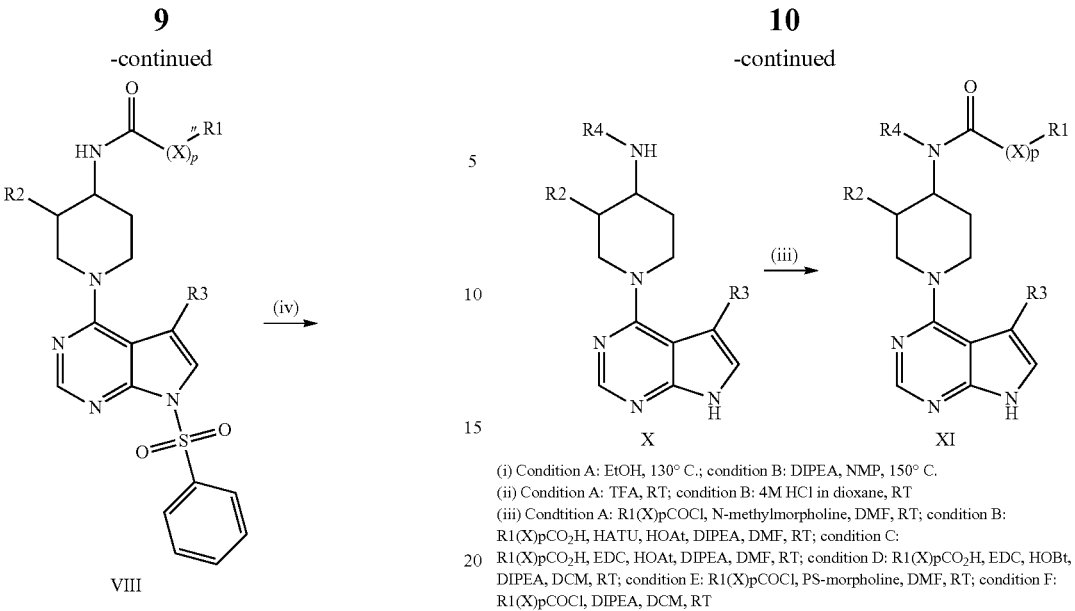

(i) Condition A: EtOH, 130° C.; condition B: DIPEA, NMP, 150° C.
(ii) Condition A: TFA, RT; condition B: 4M HCl in dioxane, RT
(iii) Condtition A: R1(X)pCOCl, N-methylmorpholine, DMF, RT; condition B: R1(X)pCO2H, HATU, HOAt, DIPEA, DMF, RT; condition C: R1(X)pCO2H, EDC, HOAt, DIPEA, DMF, RT; condition D: R1(X)pCO2H, EDC, HOBt, DIPEA, DCM, RT; condition E: R1(X)pCOCl, PS-morpholine, DMF, RT; condition F: R1(X)pCOCl, DIPEA, DCM, RT

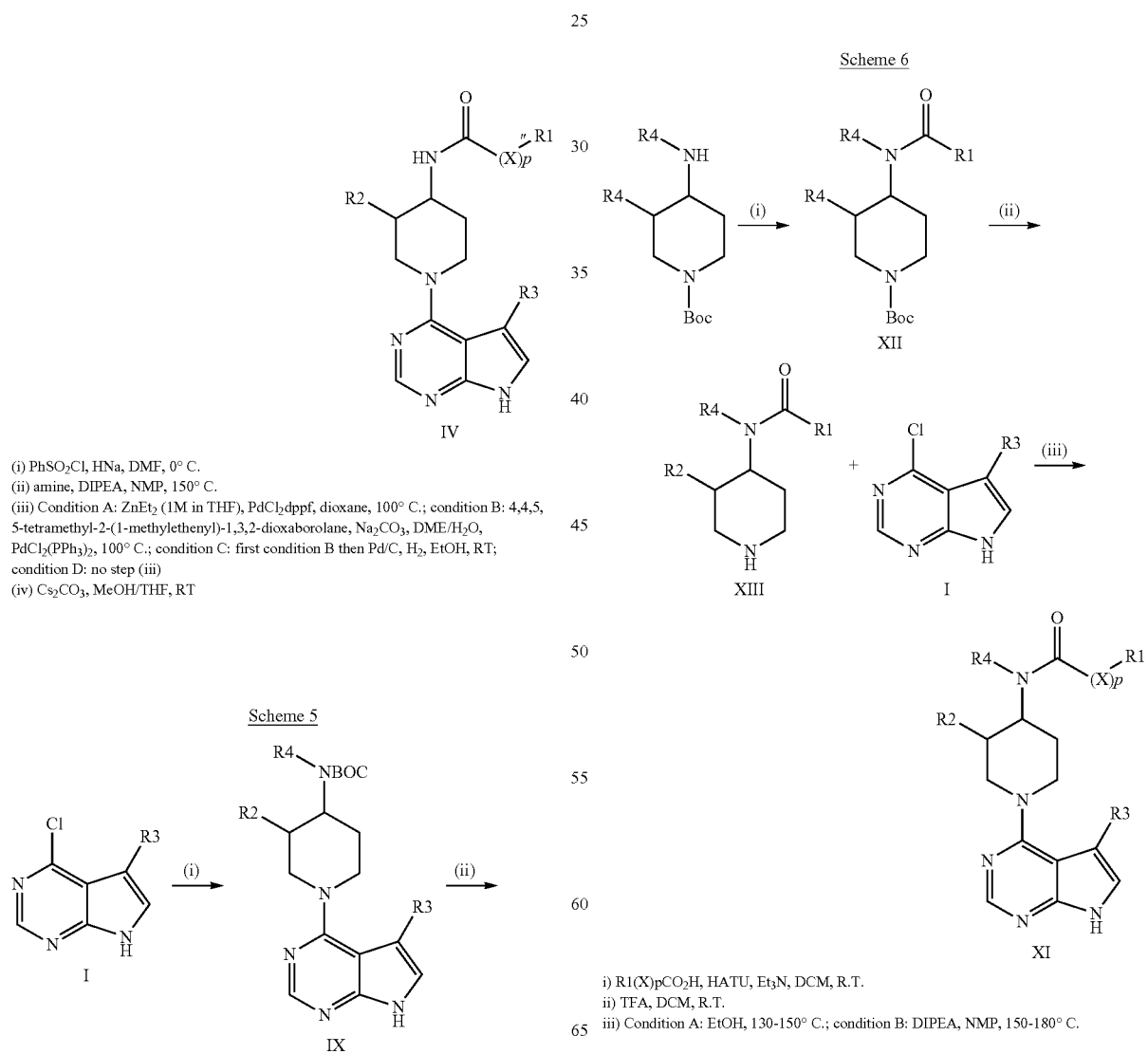

(i) PhSO2Cl, HNa, DMF, 0° C.
(ii) amine, DIPEA, NMP, 150° C.
(iii) Condition A: ZnEt2 (1M in THF), PdCl2dppf, dioxane, 100° C.; condition B: 4,4,5,5-tetramethyl-2-(1-methylethenyl)-1,3,2-dioxaborolane, Na2CO3, DME/H2O, PdCl2(PPh3)2, 100° C.; condition C: first condition B then Pd/C, H2, EtOH, RT; condition D: no step (iii)
(iv) Cs2CO3, MeOH/THF, RT i) R1(X)pCO2H, HATU, Et3N, DCM, R.T.
ii) TFA, DCM, R.T.
iii) Condition A: EtOH, 130-150° C.; condition B: DIPEA, NMP, 150-180° C.

Scheme 7
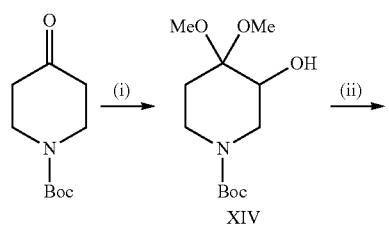
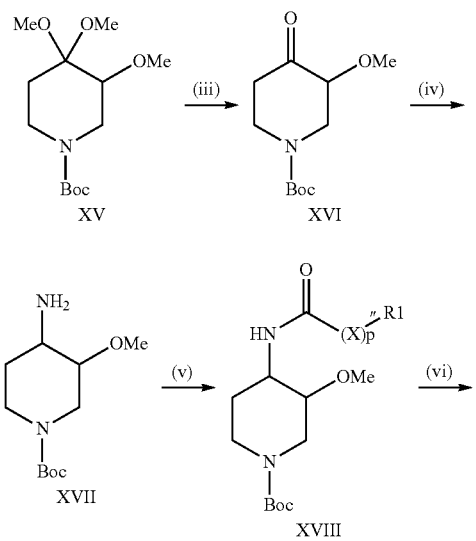
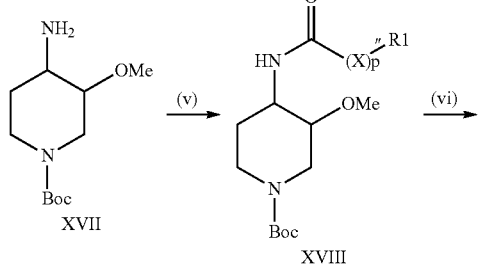
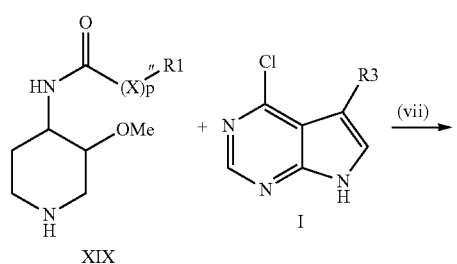
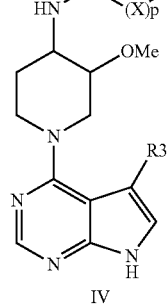
i) KOH, MeOH, I$_2$, 0° C. TO R.T.
ii) KOtBu, MeI, THF 0° C. to R.T
iii) HCl in 1,4-Dioxane, 50° C.
iv) NaCNBH$_4$, Ammonium acetate, MeOH, R.T.
v) R1(X)pCOCl, Et$_3$N, DCM, R.T.
vi) HCl in 1,4-dioxane, R.T.
vii) Condition A: EtOH, 130-150° C.; condition B: DIPEA, NMP, 150-180° C.
Scheme 8
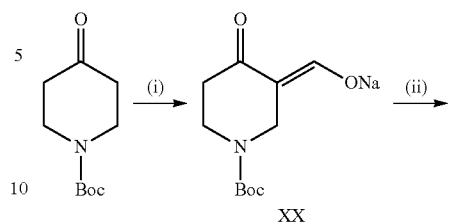
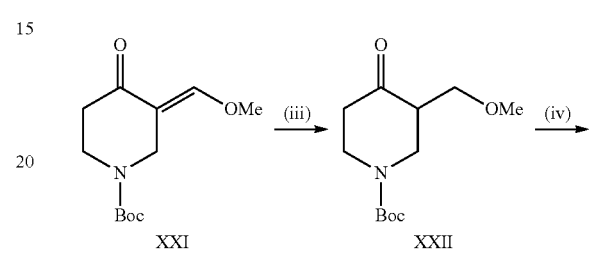
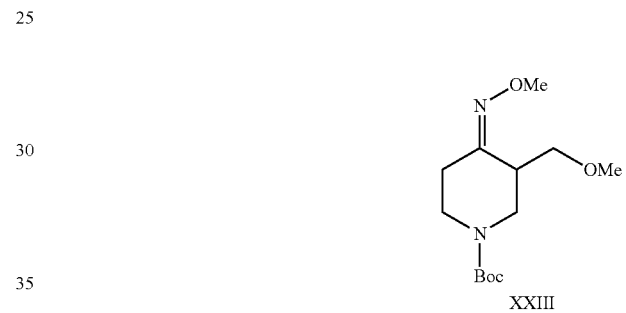
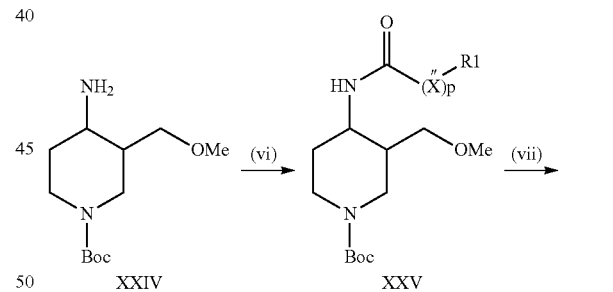
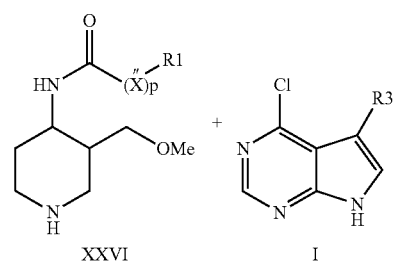
(viii)

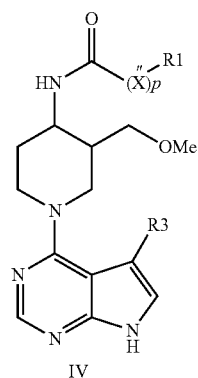
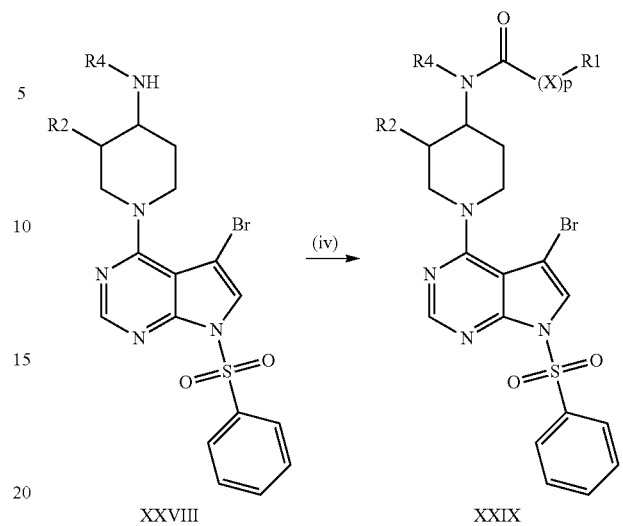
i) Na, Et2O, EtOH, Ethyl formate, 5° C.
ii) K₂CO₃, Me₂SO₄, Acetone, 65° C.
iii) 5% Pd/C, MeOH, H₂
iv) hydroxylamine HCl, EtOH, 78° C.
v) H₂, raney-nickel, MeOH
v) R1(X)pCOCl, Et3N, DCM, R.T.
vi) HCl in 1,4-dioxane, R.T.
vii) Condition A: EtOH, 130-150° C.; condition B: DIPEA, NMP, 150-180° C.
Scheme 9
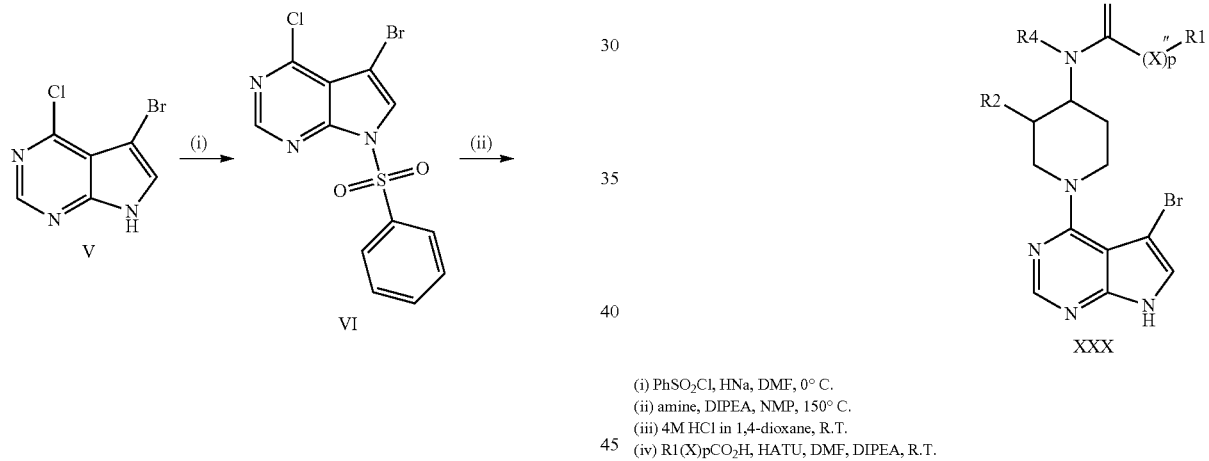
(i) PhSO₂Cl, HNa, DMF, 0° C.
(ii) amine, DIPEA, NMP, 150° C.
(iii) 4M HCl in 1,4-dioxane, R.T.
(iv) R1(X)pCO₂H, HATU, DMF, DIPEA, R.T.
(v) Cs₂CO₃, MeOH/THF, RT
Scheme 10
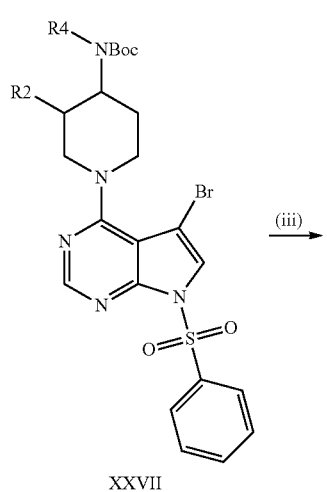
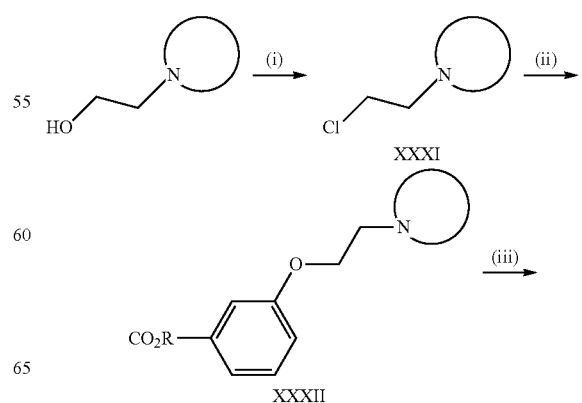

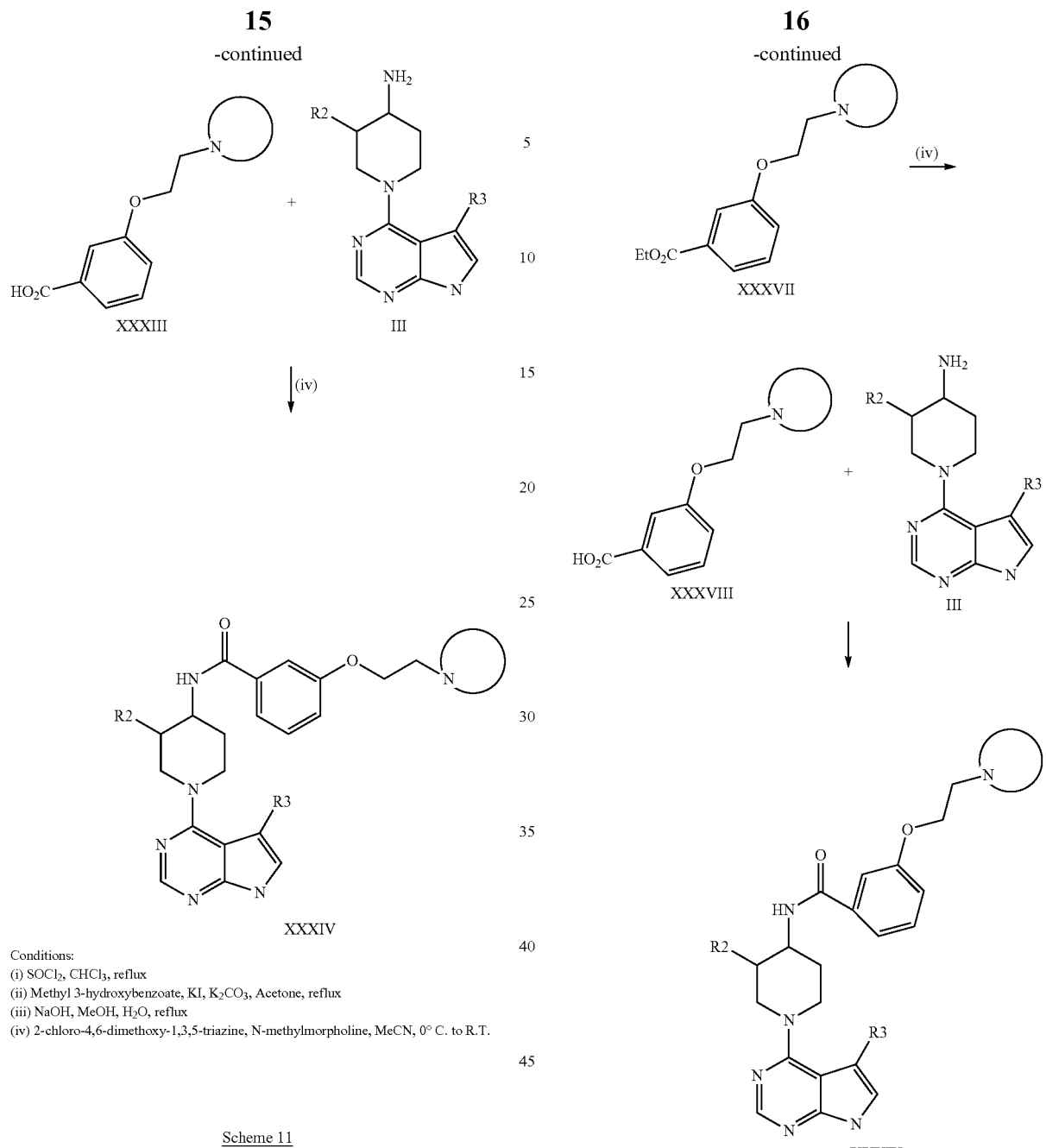
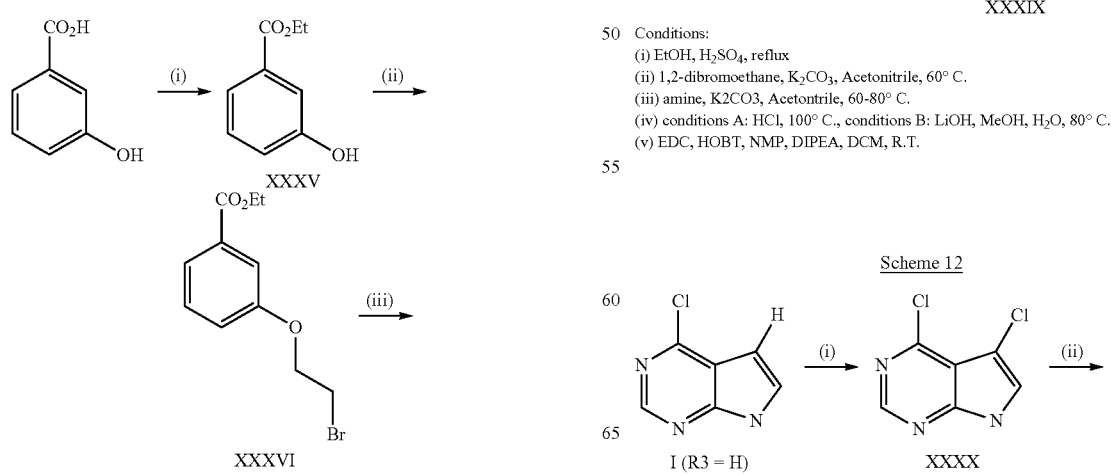

-continued

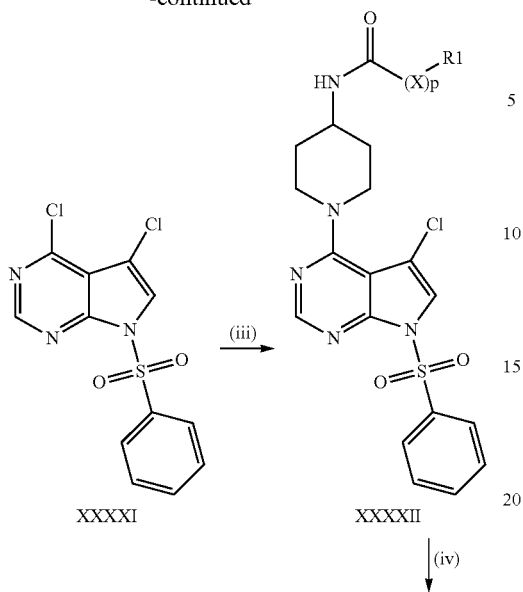

Conditions:
(i) NCS, DCM, R.T. then 60° C.
(ii) NaH(60% w/w in mineral oil), Phenyl sulfonyl chloride, DMF, 0° C.
(iii) amine, NMP, DIPEA, R.T.
(iv) NaOMe, MeOH, 75° C.

Scheme 13

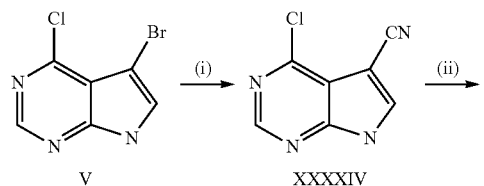

-continued

Conditions:
(i) nBu—Li, THF, 4-Methylbenzenesulfonyl chloride, -78° C. to R.T.
(ii) K₂CO₃, {2-[(chloromethyl)oxy]ethyl}(trimethyl)silane, DMF, R.T.
(iii) N-4-piperidinylbenzamide, DIPEA, NMP, 120° C.
(iv) LiBF₄, MeCN, 80° C.

It will be understood by those skilled in the art that certain compounds of the invention can be converted into other compounds of the invention according to standard chemical methods.

The starting materials for use in the schemes are commercially available, known in the literature or can be prepared by known methods.

Pharmaceutically acceptable salts may be prepared conventionally by reaction with the appropriate acid or acid derivative.

The present invention provides compounds of formula (I) or a pharmaceutically acceptable salt thereof for use in therapy.

The compounds of formula (I) or their pharmaceutically acceptable salts may be of use for the treatment or prophylaxis of a disease or disorder where an inhibitor of a human ASK1 is required.

The compounds of formula (I) or their pharmaceutically acceptable salts may be of use for the treatment or prophylaxis of pain, for example, chronic articular pain (e.g. rheumatoid arthritis, osteoarthritis, rheumatoid spondylitis, gouty arthritis and juvenile arthritis) including the property of disease modification and joint structure preservation; musculoskeletal pain; lower back and neck pain; sprains and strains;

neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea.

The compounds of formula (I) or their pharmaceutically acceptable salts may be particularly useful in the treatment or prophylaxis of neuropathic pain and symptoms associated therewith. Neuropathic pain syndromes include: diabetic neuropathy; sciatica; non-specific lower back pain; multiple sclerosis pain; fibromyalgia; HIV-related neuropathy; postherpetic neuralgia; trigeminal neuralgia; and pain resulting from physical trauma, amputation, cancer, toxins, chemotherapy induced neuropathy or chronic inflammatory conditions. Symptoms of neuropathic pain include spontaneous shooting and lancinating pain, or ongoing, burning pain. In addition, there is included pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold or mechanical hyperalgesia), continuing pain sensation after removal of the stimulation (hyperpathia) or an absence of or deficit in selective sensory pathways (hypoalgesia).

The compounds of formula (I) or their pharmaceutically acceptable salts may also be useful in the treatment or prophylaxis of inflammation, for example in the treatment of skin conditions (e.g. sunburn, burns, eczema, dermatitis, psoriasis); ophthalmic diseases such as glaucoma, retinitis, retinopathies, uveitis and of acute injury to the eye tissue (e.g. conjunctivitis); lung disorders (e.g. asthma, bronchitis, emphysema, allergic rhinitis, respiratory distress syndrome, pigeon fancier's disease, farmer's lung, COPD); gastrointestinal tract disorders (e.g. aphthous ulcer, Crohn's disease, atopic gastritis, gastritis varialoforme, ulcerative colitis, coeliac disease, regional ileitis, irritable bowel syndrome, inflammatory bowel disease, gastrointestinal reflux disease, diarrhoea, constipation); organ transplantation; other conditions with an inflammatory component such as rheumatoid arthritis, vascular disease, steatohepatitis, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, polymyositis, gingivitis, myocardial ischemia, pyrexia, systemic lupus erythematosus, polymyositis, tendinitis, bursitis, and Sjogren's syndrome.

The compounds of formula (I) or their pharmaceutically acceptable salts may also be useful in the treatment or prophylaxis of cardiovascular diseases such as hypertension or myocardial ischemia; functional or organic venous insufficiency; varicose therapy; haemorrhoids; shock states associated with a marked drop in arterial pressure (e.g. septic shock); cardiac hypertrophy, ventricular fibrosis, myocardial remodelling and atherosclerosis.

The compounds of formula (I) or their pharmaceutically acceptable salts may also be useful in the treatment or prophylaxis of neurodegenerative diseases and neurodegeneration such as dementia, particularly degenerative dementia (including senile dementia, Alzheimer's disease, Pick's disease, Huntingdon's chorea, Parkinson's disease and Creutzfeldt-Jakob disease, ALS and motor neuron disease); vascular dementia (including multi-infarct dementia); as well as dementia associated with intracranial space occupying lesions; trauma; infections and related conditions (including HIV infection); metabolism; toxins; anoxia and vitamin deficiency; and mild cognitive impairment associated with ageing, particularly Age Associated Memory Impairment.

The compounds of formula (I) or their pharmaceutically acceptable salts may also be useful in the treatment or prophylaxis of the underlying neuronal degeneration in neurodegenerative diseases (including peripheral neuropathies, retinopathies, glaucoma, macular degeneration, motor neurone disease, Parkinson's disease, Alzheimer's disease, multiple sclerosis, Huntingdon's chorea, stroke, cerebral ischemia and traumatic brain injury).

The compounds of formula (I) or their pharmaceutically acceptable salts may also be useful in the treatment or prophylaxis of neurological disorders and may be useful as neuroprotecting agents. The compounds of the invention may also be useful in the treatment of neurodegeneration following stroke, cardiac arrest, pulmonary bypass, traumatic brain injury, spinal cord injury or the like.

The compounds of formula (I) or their pharmaceutically acceptable salts may also be useful in the treatment of complications of Type 1 diabetes (e.g. diabetic microangiopathy, diabetic retinopathy, diabetic nephropathy, macular degeneration, glaucoma), nephrotic syndrome, diabetic cardiomyopathy, aplastic anaemia, uveitis, Kawasaki disease and sarcoidosis as well as disorders of fat metabolism which may be associated with diabetes or obesity for example hepatic steatosis.

The compounds of formula (I) or their pharmaceutically acceptable salts may also be useful in the treatment of cancers for example hepatocellular carcinoma, melanoma, gastric cancer, liposarcoma and cancers caused by oxidative stresses for example cervical spondylotic myelopathy.

The invention also provides a method of treating or preventing pain, for example those pain indications mentioned hereinabove, or a disease or disorder mentioned hereinabove, which comprises administering to a subject in need thereof an effective amount of a compound of formula (I) or a pharmaceutically acceptable salt thereof.

The invention also provides a compound of formula (I), or a pharmaceutically acceptable salt thereof, for use in the treatment or prophylaxis of pain, for example those pain indications mentioned hereinabove, or a disease or disorder mentioned hereinabove.

The invention also provides the use of a compound of formula (I), or a pharmaceutically acceptable salt thereof, in the manufacture of a medicament for the treatment or prophylaxis of pain, for example those pain indications mentioned hereinabove, or a disease or disorder mentioned hereinabove.

For use in therapy the compounds of the invention are usually administered as a pharmaceutical composition. The invention also provides a pharmaceutical composition comprising a compound of formula (I), or a pharmaceutically acceptable salt thereof, and a pharmaceutically acceptable carrier.

The compounds of formula (I) or their pharmaceutically acceptable salts may be administered by any convenient method, e.g. by oral, parenteral, buccal, sublingual, nasal, rectal or transdermal administration, and the pharmaceutical compositions adapted accordingly.

The compounds of formula (I) or their pharmaceutically acceptable salts which are active when given orally can be formulated as liquids or solids, e.g. as syrups, suspensions, emulsions, tablets, capsules or lozenges.

A liquid formulation will generally consist of a suspension or solution of the active ingredient in a suitable liquid carrier(s) e.g. an aqueous solvent such as water, ethanol or glycerine, or a non-aqueous solvent, such as polyethylene glycol or an oil. The formulation may also contain a suspending agent, preservative, flavouring and/or colouring agent.

A composition in the form of a tablet can be prepared using any suitable pharmaceutical carrier(s) routinely used for preparing solid formulations, such as magnesium stearate, starch, lactose, sucrose and cellulose.

A composition in the form of a capsule can be prepared using routine encapsulation procedures, e.g. pellets containing the active ingredient can be prepared using standard carriers and then filled into a hard gelatin capsule; alternatively a dispersion or suspension can be prepared using any suitable pharmaceutical carrier(s), e.g. aqueous gums, celluloses, silicates or oils and the dispersion or suspension then filled into a soft gelatin capsule.

Typical parenteral compositions consist of a solution or suspension of the active ingredient in a sterile aqueous carrier or parenterally acceptable oil, e.g. polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active ingredient in a pharmaceutically acceptable aqueous or non-aqueous solvent and are usually presented in single or multidose quantities in sterile form in a sealed container which can take the form of a cartridge or refill for use with an atomising device. Alternatively the sealed container may be a disposable dispensing device such as a single dose nasal inhaler or an aerosol dispenser fitted with a metering valve. Where the dosage form comprises an aerosol dispenser, it will contain a propellant which can be a compressed gas e.g. air, or an organic propellant such as a fluorochlorohydrocarbon or hydrofluorocarbon. Aerosol dosage forms can also take the form of pump-atomisers.

Compositions suitable for buccal or sublingual administration include tablets, lozenges and pastilles where the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

In one embodiment the composition is in unit dose form such as a tablet, capsule or ampoule.

The dose of the compound of formula (I), or a pharmaceutically acceptable salt thereof, used in the treatment or prophylaxis of the abovementioned disorders or diseases will vary in the usual way with the particular disorder or disease being treated, the weight of the subject and other similar factors. However, as a general rule, suitable unit doses may contain from 0.1% to 100% by weight, for example from 10 to 60% by weight, of the active material, depending on the method of administration. The composition may contain from 0% to 99% by weight, for example 40% to 90% by weight, of the carrier, depending on the method of administration. The composition may contain from 0.05 mg to 1000 mg, for example from 1.0 mg to 500 mg, of the active material, depending on the method of administration. The composition may contain from 50 mg to 1000 mg, for example from 100 mg to 400 mg of the carrier, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 500 mg, and such unit doses may be administered more than once a day, for example two or three a day. Such therapy may extend for a number of weeks or months.

Compounds of the invention may be identified and characterised using screening procedures and assays including, for example, activity assays and functional assays.

An example of an assay that may be used to characterise compounds which inhibit the activity of ASK1 is one that uses IMAP™ technology. In this method ASK1 activity is measured in an immobilised metal ion affinity-based fluorescence polarisation (IMAP™ FP) assay, which measures the degree of phosphorylation of a fluorescently labelled peptide substrate. IMAP™ technology is based on high affinity binding of phosphate at high salt concentrations by immobilized metal ($M^{III}$). The IMAP™ "binding reagent" complexes with phosphate groups on the phosphopeptide generated by the kinase reaction. Binding causes a change in the rate of the molecular motion of the peptide, resulting in an increase in fluorescence polarization (FP) observed. Hence, inhibition of activity is seen as a decrease in FP signal due to a lack of phospho-peptide.

Another example of an activity assay is an AlphaLISA0 assay (Eglen R M et al. (2008) Curr Chem Genomics 1 p2). In this assay ASK1 activity is determined by measuring the degree of phosphorylation of a protein substrate (for example MKK4 or MKK7).

AlphaLISA® technology is based on the binding of a substrate to two types of beads: acceptor and donor. Binding to one bead is through the tag of the substrate protein. Binding of the second bead is through phosphospecific binding of an antibody to the phosphosite of the substrate. This forms a sandwich, with the acceptor and donor beads in close proximity. When the donor beads are excited by light in the 680 nm range, a singlet oxygen is released and causes emission of light from the acceptor in the 620 nm range which can be detected in a suitable reader.

A suitable binding assay for determining ASK1 activity is a fluorescence polarisation (FP) ligand binding assay. As an example, this assay may involve the use of a Rhodamine Green labelled promiscuous kinase inhibitor that can be used as a competitor.

The present invention also provides ASK1 inhibitors, or their pharmaceutically acceptable salts, for use in the treatment or prophylaxis of pain, for example chronic articular pain (e.g. rheumatoid arthritis, osteoarthritis, rheumatoid spondylitis, gouty arthritis and juvenile arthritis) including the property of disease modification and joint structure preservation; musculoskeletal pain; lower back and neck pain; sprains and strains; neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea.

In particular ASK1 inhibitors or their pharmaceutically acceptable salts may be particularly useful in the treatment or prophylaxis of neuropathic pain and symptoms associated therewith. Neuropathic pain syndromes include: diabetic neuropathy; sciatica; non-specific lower back pain; multiple sclerosis pain; fibromyalgia; HIV-related neuropathy; post-herpetic neuralgia; trigeminal neuralgia; and pain resulting from physical trauma, amputation, cancer, toxins or chronic inflammatory conditions. Symptoms of neuropathic pain include spontaneous shooting and lancinating pain, or ongoing, burning pain. In addition, there is included pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold or mechanical hyperalgesia), continuing pain sensation after removal of the stimulation (hyperpathia) or an absence of or deficit in selective sensory pathways (hypoalgesia).

The invention also provides a method of treating pain, for example those pain indications mentioned hereinabove, which comprises administering to a subject in need thereof an effective amount of an ASK1 inhibitor or a pharmaceutically acceptable salt thereof.

The invention also provides an ASK1 inhibitor, or a pharmaceutically acceptable salt thereof, for use in the treatment or prophylaxis of pain, for example those pain indications mentioned hereinabove.

The invention also provides the use of an ASK1 inhibitor, or a pharmaceutically acceptable salt thereof, in the manufacture of a medicament for the treatment or prophylaxis of pain, for example those pain indications mentioned hereinabove.

For use in therapy the ASK1 inhibitors are usually administered as a pharmaceutical composition for example a composition comprising an ASK1 inhibitor or a pharmaceutically acceptable salt thereof, and a pharmaceutically acceptable carrier. Examples of such compositions, and methods of administration thereof, which compositions comprise a compound of formula (I) or a pharmaceutically acceptable salt thereof, are described hereinabove. Such compositions and methods of administration may also be used for other ASK1 inhibitors or pharmaceutically acceptable salts thereof, in the treatment of pain, for example those pain indications mentioned hereinabove.

ASK1 inhibitors for use in the treatment of pain, for example those pain indications mentioned hereinabove may be identified and characterised using screening procedures as described hereinabove.

Throughout the specification and claims which follow, unless the context requires otherwise, the word 'comprise', and variations such as 'comprises' and 'comprising' will be understood to imply the inclusion of a stated integer or step or group of integers but not to the exclusion of any other integer or step or group of integers or steps.

All publications, including but not limited to patents and patent applications, cited in this specification are herein incorporated by reference as if each individual publication were specifically and individually indicated to be incorporated by reference herein as though fully set forth.

The following Examples illustrate the preparation of certain compounds of formula (I) or salts thereof. The Descriptions 1 to 54 illustrate the preparation of intermediates used to make compounds of formula (I) or salts thereof.

In the procedures that follow, after each starting material, reference to a description is typically provided. This is provided merely for assistance to the skilled chemist. The starting material may not necessarily have been prepared from the Description referred to.

The yields were calculated assuming that products were 100% pure if not stated otherwise.

Abbreviations
ACN Acetonitrile
Aza-HOBt 1-Hydroxy-7-azabenzotriazole
BOC t-Butyloxycarbonyl
nBu-Li n-Butyl Lithium
$CDCl_3$ deuterated chloroform
$CHCl_3$ Chloroform
DCM Dichloromethane
DIPEA N,N-Diisopropylethylamine
DMF N,N-Dimethylformamide
DMSO Dimethylsulphoxide
EA Ethyl acetate
EDC N-(3-Dimethylaminopropyl)-N' ethylcarbodiimide hydrochloride
e.e Enantiomeric excess
$Et_2O$ Diethyl ether
EtOAc Ethyl acetate
ETOH Ethanol
HATU 0-(7-Azabenzotriazol-1-yl)-N,N,N',N'-tetramethyluronium hexafluorophosphate
HCl Hydrogen chloride
$H_2O$ Water
HOAt 1-Hydroxy-7-azabenzotriazole
HOBt 1-Hydroxybenzotriazole
$H_2SO_4$ Sulfuric acid
$K_2CO_3$ Potassium carbonate
LCMS Liquid chromatography coupled to mass spectrometer
$LiBE_4$ Lithium tetrafluoroborate
MDAP Mass-directed auto preparative high performance liquid chromatography
MeCN Acetonitrile
MeOH Methanol
$MgSO_4$ Magnesium Sulfate
$Na_2CO_3$ Sodium carbonate
$NaHCO_3$ Sodium bicarbonate
NaOH Sodium hydroxide
$Na_2SO_4$ Sodium Sulfate
NBS N-Bromo succinimide
NCS N-Chloro succinimide
$NH_3$ Ammonia
$NH_4Cl$ Ammonium chloride
$NH_4HCO_3$ Ammonium bicarbonate
NMP 1-methyl 2-pyrrolidinone
NMR nuclear magnetic resonance
Pd/C Palladium on carbon
$PdCl_2(dppf)-CH_2Cl_2$ [1,1'-Bis(diphenylphosphino)ferrocene]dichloropalladium(II); complex with Dichloromethane
Pet Eth petroleum ether
Pol-NMM Polymer supported morpholine
SCX-2 silica-based sorbent with a chemically bonded propylsulfonic acid functional group
Si—$NH_2$ Silica based sorbant with chemically bonded aminopropyl functional group
TEA Triethylamine
TFA Trifluoroacetic acid
THF Tetrahydrofuran
Mass-Directed Automated HPLC
Where applicable, purification by mass-directed automated HPLC was carried out using the following apparatus and conditions:
Hardware:
    Waters 2525 Binary Gradient Module
    Waters 515 Makeup Pump
    Waters Pump Control Module
    Waters 2767 Inject Collect
    Waters Column Fluidics Manager
    Waters 2996 Photodiode Array Detector
    Waters ZQ Mass Spectrometer Gilson 202 fraction collector
Gilson Aspec waste collector
Software: Waters MassLynx version 4 SP2
Column: the columns used were Waters Atlantis, the dimensions of which are 19 mm×100 mm (small scale) and 30 mm×100 mm (large scale). The stationary phase particle size is 5 μm.
Acidic Method:
Solvents:
A: Aqueous solvent=Water+0.1% Formic Acid
B: Organic solvent=Acetonitrile+0.1% Formic Acid
Make up solvent=Methanol:Water 80:20
Needle rinse solvent=Methanol
Methods:
There are five methods used depending on the analytical retention time of the compound of interest. They have a 13.5-minute runtime, which comprises of a 10-minute gradient followed by a 3.5 minute column flush and re-equilibration step.
Large/Small Scale 1.0-1.5 (HPLC), 0.4-0.6 (UPLC)=5-30% B
Large/Small Scale 1.5-2.2 (HPLC), 0.6-0.9 (UPLC)=15-55% B
Large/Small Scale 2.2-2.9 (HPLC), 0.9-1.2 (UPLC)=30-85% B
Large/Small Scale 2.9-3.6 (HPLC), 1.2-1.4 (UPLC)=50-99% 0
Large/Small Scale 3.6-5.0 (HPLC), 1.4-2.0 (UPLC)=80-99% B (in 6 minutes followed by 7.5 minutes flush and re-equilibration)
Flow rate: all of the above methods have a flow rate of either 20 mls/min (Small Scale) or 40 mls/min (Large Scale).
High pH Method:
Column: the HPLC analysis was conducted on an)(Bridge C18 column (100 nm×19 nm i.d. 5 μm packing diameter) at ambient temperature
Solvents:
A: 10 mM Ammonium bicarbonate in water, adjusted to pH 10 with ammonia solution.
B: Acetonitrile.
Methods:
There are five methods used depending on the analytical retention time of the compound of interest. They have a 15-minute runtime, which comprises of a 10 minute gradient followed by a 5 minute column flush and re-equilibration step.
Large/Small Scale 1.0-1.5 (HPLC), 0.4-0.6 (UPLC)=1-30% B
Large/Small Scale 1.5-2.2 (HPLC), 0.6-0.9 (UPLC)=15-55% B
Large/Small Scale 2.2-2.9 (HPLC), 0.9-1.2 (UPLC)=30-85% B
Large/Small Scale 2.9-3.6 (HPLC), 1.2-1.4 (UPLC)=50-99% B
Large/Small Scale 3.6-5.0 (HPLC), 1.4-2.0 (UPLC)=80-99% B (in 6 minutes followed by 7.5 minutes flush an re-equilibration)
Flow rate: all of the above methods have a flow rate of either 20 ml/min (small scale) or 40 ml/min (large scale)
Liquid Chromatography/Mass Spectrometry
Analysis of the above Examples by Liquid Chromatography/Mass Spectrometry (LC/MS) was carried out using the apparatus and conditions indicated in the methods shown below:

Liquid Chromatography:
5 Minute Method:
Formic Acid Generic Analytical HPLC Open Access LC/MS
The HPLC analysis was conducted on a Sunfire C18 column (30 mm×4.6 mm i.d. 3.5 μm packing diameter) at 30 degrees centigrade.
The solvents employed were:
A: 0.1% v/v solution of Formic Acid in Water.
B: 0.1% v/v solution of Formic Acid in Acetonitrile.

| Time (min) | Flow Rate (ml/min) | % A | % B |
| --- | --- | --- | --- |
| 0 | 3 | 97 | 3 |
| 0.1 | 3 | 97 | 3 |
| 4.2 | 3 | 0 | 100 |
| 4.8 | 3 | 0 | 100 |
| 4.9 | 3 | 97 | 3 |
| 5.0 | 3 | 97 | 3 |

The UV detection was an averaged signal from wavelength of 210 nm to 350 nm and mass spectra were recorded on a mass spectrometer using alternate-scan positive and negative mode electrospray ionization.
2 Minute Method:
Formic Acid Generic Analytical UPLC Open Access LC/MS
The UPLC analysis was conducted on an Acquity UPLC BEH C18 column (2.1 mm×50 mm i.d. 1.7 μm packing diameter) at 40 degrees centigrade.
The solvents employed were:
A: 0.1% v/v solution of Formic Acid in Water.
B: 0.1% v/v solution of Formic Acid in Acetonitrile.

| Time (min) | Flow Rate (ml/min) | % A | % B |
| --- | --- | --- | --- |
| 0 | 1 | 97 | 3 |
| 1.5 | 1 | 0 | 100 |
| 1.9 | 1 | 0 | 100 |
| 2.0 | 1 | 97 | 3 |

The UV detection was an averaged signal from wavelength of 210 nm to 350 nm and mass spectra were recorded on a mass spectrometer using alternate-scan positive and negative mode electrospray ionization.
High pH 5 minute Method:
High pH Generic Analytical HPLC Open Access LC/MS 5 Minute Method
The HPLC analysis was conducted on an)(Bridge C18 column (50 mm×4.6 mm i.d. 3.5 μm packing diameter) at 30 degrees centigrade.
The solvents employed were:
A: 10 mM Ammonium bicarbonate in water, adjusted to pH 10 with ammonia solution.
B: Acetonitrile.
The gradient employed was:

| Time (min) | Flow Rate (ml/min) | % A | % B |
| --- | --- | --- | --- |
| 0 | 3 | 99 | 1 |
| 0.1 | 3 | 99 | 1 |
| 4.0 | 3 | 3 | 97 |
| 5.0 | 3 | 3 | 97 |

The UV detection was an averaged signal from wavelength of 210 nm to 350 nm and mass spectra were recorded on a mass spectrometer suing alternate-scan positive and negative mode electrospray ionization.

High pH 2 minute Method:

High pH Generic analytical UPLC Open Access LC/MS 2 Minute Method

The UPLC analysis was conducted on an Acquity UPLC BEH C18 column (2.1 mm×50 mm i.d. 1.7 μm packing diameter) at 40 degrees centigrade.

The solvents employed were:

A: 10 mM Ammonium bicarbonate in water adjusted to pH 10 with ammonia solution.

B: Acetonitrile.

The gradient employed was:

| Time (min) | Flow Rate (ml/min) | % A | % B |
|---|---|---|---|
| 0 | 1 | 99 | 1 |
| 1.5 | 1 | 3 | 97 |
| 1.9 | 1 | 3 | 97 |
| 2.0 | 1 | 0 | 100 |

The UV detection was an averaged signal from wavelength of 220 nm to 350 nm and mass spectra were recorded on a mass spectrometer using alternate-scan positive and negative mode electrospray iodization.

Description 1 (D1)

1,1-dimethylethyl[1-(7H-pyrrolo[2,3-d]pyrimidin-4-yl)-4-piperidinyl]carbamate

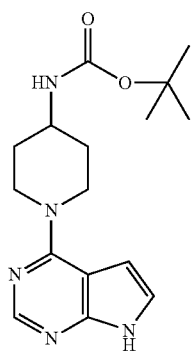

A mixture of 4-chloro-7H-pyrrolo[2,3-d]pyrimidine (0.154 g, 1 mmol) and 1,1-dimethylethyl 4-piperidinylcarbamate (0.240 g, 1.200 mmol) in ethanol (3 mL) was microwaved at 130° C. for 15 minutes. The white solid precipitate was filtered and washed with Et$_2$O to give the title product D1 (171 mg), $^1$H NMR (d6-DMSO) δ 11.68 (1H, brs), 8.12 (1H, s), 7.17 (1H, dd), 6.87 (1H, d), 6.56 (1H, dd), 4.59 (2H, dt), 3.58 (1H, m), 3.15 (2H, dt), 1.83 (2H, m), 1.39 (9H, s), 1.36 (2H, m), MS(ES+) 318 [M+H]$^+$.

Description 2 (D2)

1-(7H-pyrrolo[2,3-d]pyrimidin-4-yl)-4-piperidinamine

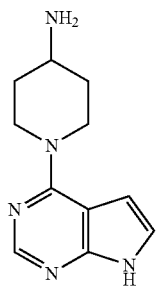 [SMILES: NC1CCN(c2ncnc3[nH]ccc23)CC1]

Trifluoroacetic acid (TFA) (5 ml) was added to 1,1-dimethylethyl[1-(7H-pyrrolo[2,3-d]pyrimidin-4-yl)-4-piperidinyl]carbamate D1 (0.945 g). The mixture was stirred at room temperature for 1 hour the TFA was evaporated. The crude mixture was purified by a 10 g Isolute SCX-2 silica cartridge (Biotage) eluting with MeOH then with a 2M NH$_3$ in MeOH solution. The product-containing fraction was evaporated and the crude product was triturated with Et$_2$O to give the title product D2 (653 mg), $^1$H NMR (d6-DMSO) δ 11.68 (1H, brs), 8.12 (1H, s), 7.16 (1H, dd), 6.60 (1H, d), 4.56 (2H, dt), 4.10 (1H, brs), 3.30 (3H, m), 2.90 (1H, m), 1.80 (2H, m), 1.25 (2H, m), MS(ES+) 218 [M+H]$^+$.

Description 3 (D3)

5-Bromo-4-chloro-7H-pyrrolo[2,3-d]pyrimidine

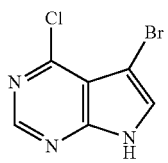

To a solution of 4-chloro-7H-pyrrolo[2,3-d]pyrimidine (2 g, 13.02 mmol) in DMF (40 mL) was added N-bromosuccinimide (2.318 g, 13.02 mmol) and the solution was stirred for 1 hour. LCMS showed almost complete conversion, but 50 mg of NBS was added to complete the reaction. The solvent was removed in vacuo and the resulting solid triturated with water and then washed with further water before drying in a vacuum oven for 18 hours at 50° C. D3 (2.613 g) was obtained as a pale brown solid, $^1$H NMR (d6-DMSO) δ 13.0 (1H, brs), 8.63 (1H, s), 7.96 (1H, s), MS(ES+) 232 [M(C$_6$H$_3$$^{79}$Br$^{35}$ClN$_3$)+H]$^+$.

Description 4 (D4)

4-Chloro-5-methyl-7H-pyrrolo[2,3-d]pyrimidine

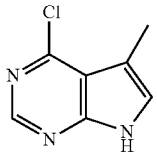

To a solution of 5-bromo-4-chloro-7H-pyrrolo[2,3-d]pyrimidine D3 (300 mg) in THF (10 mL) at −78° C. under argon was added n-butyllithium (1.16 mL, 2.90 mmol, 2.5M in hexanes) and the reaction was stirred for 20 minutes. Iodomethane (0.11 mL, 1.742 mmol) was then added dropwise and the reaction allowed to warm to room temperature in the cold bath. The reaction was quenched with water (1 mL) and the mixture concentrated in vacuo. The residue was partitioned between EtOAc (20 mL) and water (10 mL) and the organic phase was washed with brine (10 mL) before it was dried (MgSO$_4$), filtered and the solvent removed in vacuo. Attempting to dissolve the compound in DCM with some MeOH, gave some precipitate that was filtered off. This precipitate corresponds to pure D4. The filtrate was purified by silica chromatography, eluting 0-5% MeOH in DCM to give D4 as a pale grey solid. The pure D4 fractions were combined (136 mg) and analysed, NMR (d6-DMSO) δ 12.25 (1H, brs), 8.51 (1H, s), 7.44 (1H, s), 2.41 (3H, s), MS(ES+) 168 [M(C$_7$H$_6$$^{35}$ClN$_3$)+H]$^+$.

Description 5 (D5)

5-bromo-4-chloro-7-(phenylsulfonyl)-7H-pyrrolo[2,3-d]pyrimidine

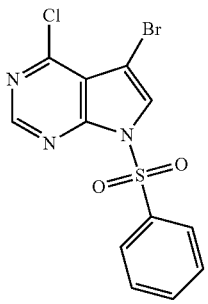 [SMILES: O=S(=O)(c1ccccc1)n1cc(Br)c2c(Cl)ncnc21]

To a solution of 5-bromo-4-chloro-7H-pyrrolo[2,3-d]pyrimidine D3 (1.00 g) in DMF (10 mL) at 0° C. was added sodium hydride (0.224 g, 5.59 mmol) and the mixture stirred for 20 minutes. Benzenesulfonyl chloride (0.66 mL, 5.16 mmol) was then added dropwise and the reaction mixture stirred in the cool bath for 1 hour. The mixture was poured onto water (140 mL) and the precipitate filtered, washed with water and dried in a vacuum oven to give D5 (1.60 g) as an off white solid, $^1$H NMR (CDCl$_3$) δ 8.77 (1H, s), 8.23 (2H, dd), 7.85 (1H, s), 7.70 (1H, m), 7.59 (2H, ddd), MS(ES+) 372 [M(C$_{12}$H$_7$$^{79}$Br$^{35}$ClN$_3$O$_2$S)+H]$^+$. The crude product was used without further purification into the preparation of D6.

Description 6 (D6)

N-{1-[5-bromo-7-(phenylsulfonyl)-7H-pyrrolo[2,3-d]pyrimidin-4-yl]-4-piperidinyl}benzamide

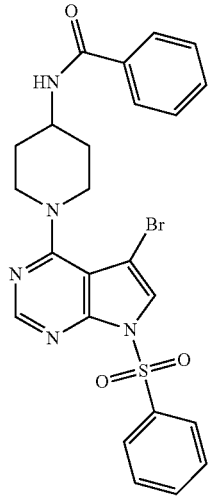 [SMILES: O=C(NC1CCN(c2ncnc3c2c(Br)cn3S(=O)(=O)c2ccccc2)CC1)c1ccccc1]

A mixture of 5-bromo-4-chloro-7-(phenylsulfonyl)-7H-pyrrolo[2,3-d]pyrimidine (1.60 g) D5, N-4-piperidinylbenzamide (1.316 g, 6.44 mmol) and DIPEA (1.87 mL, 10.73 mmol) in NMP (8 mL) was heated in the microwave at 150° C. for 20 minutes. The mixture was partitioned between EtOAc (70 mL) and water (60 mL), and the organic phase washed with water (2×60 mL) and brine (50 mL) before it was dried (MgSO$_4$), filtered and the solvent removed in vacuo. The crude material was purified by silica chromatography, eluting 0-5% MeOH in DCM to give D6 as a pure white solid (338 mg), $^1$H NMR (CDCl$_3$) δ 8.47 (1H, s), 8.23 (2H, dd), 7.75 (2H, dd), 7.63 (2H, m), 7.52 (3H, m), 6.95 (2H, m), 6.02 (1H, d), 4.28 (1H, m), 4.24 (2H, dt), 3.22 (2H, dt), 2.19 (2H, m), 1.73 (2H, m), MS(ES+) 540 [M(C$_{24}$H$_{22}$$^{79}$BrN$_5$O$_3$S)+H]$^+$.

Description 7 (D7)

N-{1-[5-ethyl-7-(phenylsulfonyl)-7H-pyrrolo[2,3-d]pyrimidin-4-yl]-4-piperidinyl}benzamide

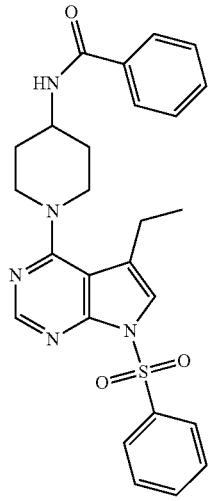 [SMILES: CCc1cn(S(=O)(=O)c2ccccc2)c2ncnc(N3CCC(NC(=O)c4ccccc4)CC3)c12]

To a suspension of N-{1-[5-bromo-7-(phenylsulfonyl)-7H-pyrrolo[2,3-d]pyrimidin-4-yl]-4-piperidinyl}benzamide D6 (200 mg) in 1,4-dioxane (3 mL) under a flush of argon was added diethylzinc (0.74 mL, 0.740 mmol) (1M in THF) followed by PdCl$_2$(dppf)-CH$_2$Cl$_2$ adduct (30.2 mg, 0.037 mmol) and the mixture heated to reflux at 100° C. for 1 hour. The mixture was allowed to cool and was partioned between EtOAc (10 mL) and aqueous sodium bicarbonate (10 mL). The organic phase was washed with water (10 mL) and brine (10 mL) before it was dried (MgSO$_4$), filtered and the solvent removed in vacuo to give crude D7 (174 mg), which was used directly for the preparation of Example 18. MS(ES+) 490 [M+H]$^+$.

Description 8 (D8)

N-{1-[5-(1-methylethenyl)-7-(phenylsulfonyl)-7H-pyrrolo[2,3-d]pyrimidin-4-yl]-4-piperidinyl}benzamide

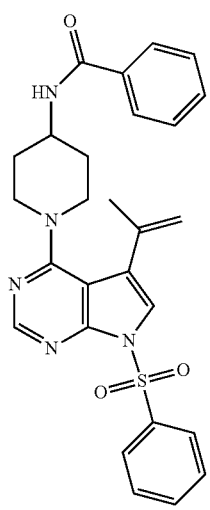 [SMILES: C=C(C)c1cn(S(=O)(=O)c2ccccc2)c2ncnc(N3CCC(NC(=O)c4ccccc4)CC3)c12]

To a mixture of N-{1-[5-bromo-7-(phenylsulfonyl)-7H-pyrrolo[2,3-d]pyrimidin-4-yl]-4-piperidinyl}benzamide D6 (600 mg), 4,4,5,5-tetramethyl-2-(1-methylethenyl)-1,3,2-dioxaborolane (373 mg, 2.220 mmol) and sodium carbonate (235 mg, 2.220 mmol) in 1,2-dimethoxyethane (7 mL) and water (3 mL) was added bis(triphenylphosphine)palladium (II) chloride (39.0 mg, 0.056 mmol). The mixture was heated in the microwave at 100° C. for 20 minutes. The mixture was partitioned between EtOAc (50 mL) and water (40 mL) and the layers separated. The organic phase was washed with water (2×40 mL) and brine (30 mL), dried (MgSO$_4$) and the solvent removed in vacuo. The crude product was purified by silica column, eluting 0-5% MeOH in DCM to give D8 (442 mg) as a white solid, $^1$H NMR (d6-DMSO) δ 8.39 (1H, s), 8.20 (2H, dd), 7.80 (4H, m), 7.72 (2H, m), 7.51 (1H, m), 7.46 (2H, dd), 5.24 (1H, d), 5.17 (1H, d), 4.05 (2H, dt), 3.65 (1H, m), 3.05 (2H, dt), 2.11 (3H, s), 1.82 (2H, m), 1.62 (2H, m), MS(ES+) 502 [M+H]$^+$.

Description 9 (D9)

N-{1-[5-(1-methylethyl)-7-(phenylsulfonyl)-7H-pyrrolo[2,3-d]pyrimidin-4-yl]-4-piperidinyl}benzamide

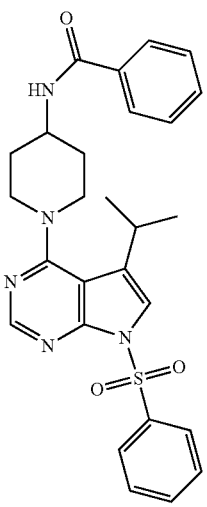 [SMILES: CC(C)c1cn(S(=O)(=O)c2ccccc2)c2ncnc(N3CCC(NC(=O)c4ccccc4)CC3)c12]

To a solution of N-{1-[5-(1-methylethenyl)-7-(phenylsulfonyl)-7H-pyrrolo[2,3-d]pyrimidin-4-yl]-4-piperidinyl}benzamide D8 (150 mg) in ethanol (40 mL) was added Pd on carbon (20 mg) and the reaction stirred under an atmosphere of hydrogen for 3 hours. The reaction was left for a further 18 hours before the mixture was filtered through celite and the filtrate concentrated in vacuo to give D9 (143 mg). The product was not purified further, but used crude for the synthesis of Example 20, $^1$H NMR (d6-DMSO) δ 8.40 (1H, s), 8.20 (2H, dd), 7.80 (4H, m), 7.72 (2H, m), 7.51 (1H, m), 7.46 (2H, dd), 4.07 (1H, m), 3.90 (2H, dt), 3.15 (1H, m), 3.05 (2H, dt), 1.90 (2H, m), 1.60 (2H, m), 1.29 (3H, d), 1.27 (3H, d), MS(ES+) 504 [M+H]$^+$.

Description 10 (D10)

1,1-dimethylethyl[1-(5-methyl-7H-pyrrolo[2,3-d]pyrimidin-4-yl)-4-piperidinyl]carbamate

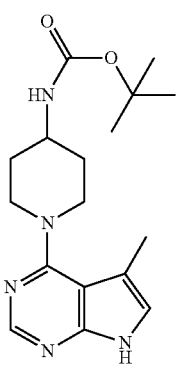 [SMILES: Cc1c[nH]c2ncnc(N3CCC(NC(=O)OC(C)(C)C)CC3)c12]

A mixture of 4-chloro-5-methyl-7H-pyrrolo[2,3-d]pyrimidine D4 (1.50 g), 1,1-dimethylethyl 4-piperidinylcarbamate (2.69 g, 13.43 mmol) and DIPEA (3.91 mL, 22.38 mmol) in NMP (10 mL) was heated in the microwave at 150° C. for 20 minutes. The mixture was partitioned between EtOAc (70 mL) and water (70 mL) and the organic phase washed with water (2×50 mL) and brine (50 mL) before it was dried (MgSO$_4$), filtered and the solvent removed in vacuo. The crude product was purified by silica chromatography, eluting 40-100% EtOAc in isohexane to give D10 (1.395 g), $^1$H NMR (d6-DMSO) δ 11.55 (1H, brs), 8.18 (1H, s), 7.04 (1H, s), 6.90 (1H, d), 3.94 (2H, dt), 3.47 (1H, m), 2.96 (2H, dt), 2.32 (3H, s), 1.86 (2H, m), 1.53 (2H, m), 1.36 (9H, s), MS(ES+) 332 [M+H]$^+$.

Description 11 (D11)

1-(5-methyl-7H-pyrrolo[2,3-d]pyrimidin-4-yl)-4-piperidinamine hydrochloride

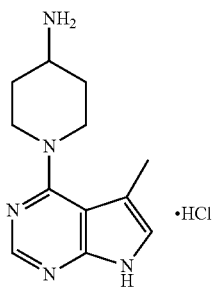

4M HCl in dioxane (10 mL) was added to 1,1-dimethylethyl[1-(5-methyl-7H-pyrrolo[2,3-d]pyrimidin-4-yl)-4-piperidinyl]carbamate D10 (1.39 g) and the mixture stirred at room temperature for 1.5 hour. The white precipitate was filtered off, washed with dioxane and then Et$_2$O before it was dried in a vacuum oven to give D11 (1.149 g) as a white solid, $^1$H NMR (d6-DMSO) δ 12.60 (1H, brs), 8.36 (1H, s), 8.34 (2H, m), 7.35 (1H, s), 4.20 (3H, m), 3.40 (2H, dt), 2.37 (3H, s), 2.10 (2H, m), 1.80 (2H, m), MS(ES+) 232 [M+H]$^+$.

Description D11a (D11a)

1-(5-methyl-7H-pyrrolo[2,3-d]pyrimidin-4-yl)-4-piperidinamine

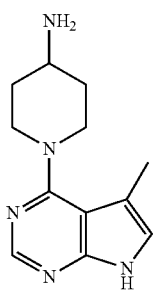 [SMILES: Cc1c[nH]c2ncnc(N3CCC(N)CC3)c12]

Trifluoroacetic acid (TFA) (5 ml) was added to a solution of 1,1-dimethylethyl[1-(5-methyl-7H-pyrrolo[2,3-d]pyrimidin-4-yl)-4-piperidinyl]carbamate D10 (580 mg, 1.313 mmol). The mixture was stirred at room temperature during one hour. The solvent was evaporated and purified using and SCX cartridge (5 g). The cartridge was washed sequentially with MeOH and then Ammonia in MeOH (0.5M and 1M). The washings with Ammonia in methanol 0.5M and 1M were combined and evaporated to give D11a (280 mg) as a white solid. LCMS [M+H]$^+$232@0.36 mins (2 minute run).

Description 12 (D12)

1,1-dimethylethyl methyl[1-(7H-pyrrolo[2,3-d]pyrimidin-4-yl)-4-piperidinyl]carbamate

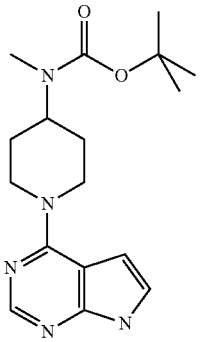 [SMILES: CN(C(=O)OC(C)(C)C)C1CCN(c2ncnc3[nH]ccc23)CC1]

1) a mixture of 4-chloro-1H-pyrrolo[2,3-d]pyrimidine (307 mg, 2 mmol, commercially available from e.g. Aldrich, Apollo or Matrix) and 1,1-dimethylethyl methyl(4-piperidinyl)carbamate (429 mg, 2.000 mmol, commercially available from e.g. Fluorochem, Astatech or Apollo) in Ethanol (4 ml) was microwaved twice at 130° C. for 15 min on normal absorption. After evaporation of the solvent, the crude product was purified via MDAP using the High pH extended method. Fractions containing product from each MDAP were combined and evaporated to give D12 as a white solid in 139 mg. LCMS [M+H]+332.06@0.76 min (2 min run)

2) a mixture of 4-chloro-1H-pyrrolo[2,3-d]pyrimidine (307 mg, 2 mmol, commercially available from e.g. Aldrich, Apollo or Matrix) and 1,1-dimethylethyl methyl(4-piperidinyl)carbamate (429 mg, 2.000 mmol, commercially available from e.g. Fluorochem, Astatech or Apollo)) in Ethanol (4 ml) was microwaved at 120° C. for 1 h on normal absorption. After evaporation of the solvent, the crude product was purified via MDAP using the High pH extended method. Fractions containing product from each MDAP were combined and evaporated to give D12 as a white solid in 158 mg. LCMS [M+H]+332.06@0.76 min (2 min run)

Description 13 (D13)

N-methyl-1-(7H-pyrrolo[2,3-d]pyrimidin-4-yl)-4-piperidinamine

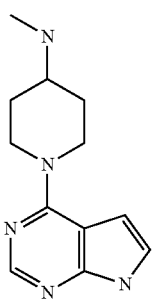 [SMILES: CNC1CCN(c2ncnc3[nH]ccc23)CC1]

Trifluoroacetic acid (TFA) (2 ml) was added to a solution of 1,1-dimethylethyl methyl[1-(7H-pyrrolo[2,3-d]pyrimidin-4-yl)-4-piperidinyl]carbamate D12 (287 mg). The mixture was stirred at room temperature during one hour. The solvent was evaporated and the mixture was checked by LCMS, the LCMS showed the desired product. Then the mixture was purified by a cartridge SCX (5 g). The fraction containing the product was evaporated, triturate with diethyl ether to give the title product D13 in 177 mg. LCMS [M+H]+231.99@0.32 min (2 min run)

Description 14 (D14)

1,1-dimethylethyl 4-[methyl(phenylcarbonyl)amino]-1-piperidinecarboxylate

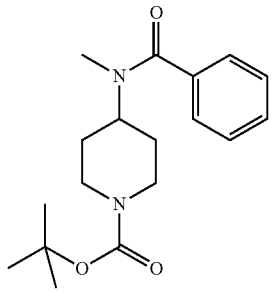 [SMILES: CN(C(=O)c1ccccc1)C1CCN(C(=O)OC(C)(C)C)CC1]

In a round bottomed flask benzoic acid (0.627 g, 5.13 mmol, commercially available from e.g. Sigma-Aldrich) and HATU (2.129 g, 5.60 mmol) were dissolved in DCM (10 mL). The reaction mixture was stirred at room temperature for 30 minutes before 1-boc-4-methylaminopiperidine (1 g, 4.67 mmol, commercially available from e.g. Apollo, Fluorochem or Astatech) was added followed by triethylamine (1.626 mL, 11.67 mmol). The reaction was stirred at room temperature overnight. Solvent was removed in vacuo and the crude dissolved in DCM then organic phase was extracted with a saturated NaHCO$_3$ solution (twice), a 10% citric acid solution (twice) then washed with brine and dried over MgSO$_4$. Solvent was removed in vacuo and the crude purified on a silica column (40+M) eluting with DCM/MeOH; 90/10. Fractions containing desired compound were joined and solvents were removed in vacuo, to give title compound D14 as a pale yellow oil in 1.66 g. LCMS [M+H]+319.13 [M+H-tBu]+263.03@1.01 min (2 min run)

Description 15 (D15)

N-methyl-N-4-piperidinylbenzamide

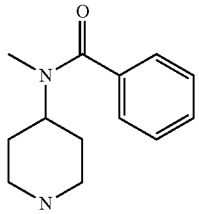 [SMILES: CN(C(=O)c1ccccc1)C1CCNCC1]

1,1-dimethylethyl 4-[methyl(phenylcarbonyl)amino]-1-piperidinecarboxylate D14 (1.66 g) was dissolved in DCM (5 mL) then TFA (4.02 mL, 52.1 mmol) was slowly added. The reaction was stirred at room temperature for 30 minutes. TFA and DCM were removed in vacuo. The crude mixture was poured on a top of an Isolute Si—SCX-2 cartridge, eluting with DCM then MeOH then a 2M NH$_3$ in MeOH solution. Fractions containing desired compound were evaporated in vacuo to give title compound D15 in 1.18 g. LCMS [M+H]+219.01@0.45 min (2 min run)

Description 16 (D16)

1,1-dimethylethyl 3-hydroxy-4,4-bis(methyloxy)-1-piperdinecarboxylate

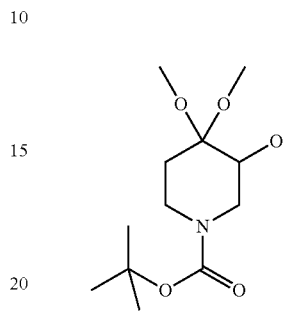

To a solution of 1,1-dimethylethyl 4-oxo-1-piperidinecarboxylate (10 g, 0.05 mol, commercially available from e.g. Sigma-Aldrich, Fluka or Apollo) in MeOH (100 ml), was added potassium hydroxide (5.2 g, 0.09 mol), at 0° C. A solution of iodine (14 g, 0.055 mol) in MeOH (100 ml) was added to the above stirred reaction mixture dropwise over 0.5 hours at 0-5° C. The reaction mixture was then allowed to warm up to room temperature and stirred for another 2 hours. After that the resulting solution was concentrated in vacuo. The residue was purified by column chromatography on silica gel eluting with Pet Eth/EtOAC 10/1 to obtain the desired product D16 as a yellow oil in 11 g.

Description 17 (D17)

1,1-dimethylethyl 3,4,4-tris(methyloxy)-1-piperidinecarboxylate

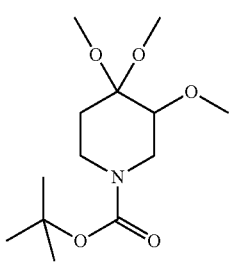 [SMILES: COC1CN(C(=O)OC(C)(C)C)CCC1(OC)OC]

To a solution of 1,1-dimethylethyl 3-hydroxy-4,4-bis(methyloxy)-1-piperidinecarboxylate D16 (11 g) in THF (150 ml) was added Potassium t-Butoxide (23.5 g, 210 mmol) at 0° C. The reaction mixture was stirred for 20 mins and the methyliodide (5.2 ml, 84 mmol) was added. The reaction mixture was allowed to warm up to room temperature and stirred overnight. The resulting mixture was concentrated and dissolved in EtOAc and washed with water. The organic layer was concentrated in vacuo to obtain crude product. Product was purified on silica gel eluting with DCM/MeOH 50/1 to obtain the desired product D17 as a yellow oil in 5 g. LCMS [MH+] 298@1.385 min (5 min run)

Description 18 (D18)

1,1-dimethylethyl 3-(methyloxy)-4-oxo-1-piperidinecarboxylate

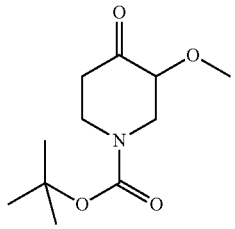 [SMILES: COC1CN(C(=O)OC(C)(C)C)CCC1=O]

To a solution of 1,1-dimethylethyl 3,4,4-tris(methyloxy)-1-piperidinecarboxylate D17 (4.85 g) in HCl/1,4-Dioxane (50 mL) was heated at 50° C. and stirred overnight. Water (50 ml) was added to the reaction mixture and the pH adjusted to 10.0 using sodium hydroxide. After that BOC anhydride (4.22 g, 19.4 mmol) was added to the reaction mixture and stirred for 4 hours. The resulting mixture was extracted with EtOAc (3×100 ml). The organic layer was dried over anhydrous MgSO$_4$, concentrated in vacuo to afford the desired product D18 in 3.1 g. LCMS [M-55]=174@1.29 min (5 min run)

Description D19 (D19)

1,1-dimethylethyl 4-amino-3-(methyloxy)-1-piperidinecarboxylate

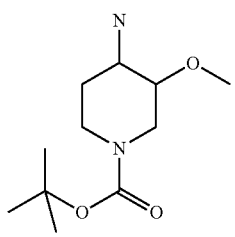 [SMILES: COC1CN(C(=O)OC(C)(C)C)CCC1N]

To a solution of 1,1-dimethylethyl 3-(methyloxy)-4-oxo-1-piperidinecarboxylate D18 (2.9 g) in MeOH (100 ml), was added sodium cyanoborohydride (7.9 g, 126 mmol) and ammonium acetate (9.7 g, 126 mmol) at R.T. The reaction mixture was stirred for 4 hours. The resulting mixture was concentrated in vacuo, dissolved in water, basified with sodium hydroxide to pH10 and extracted with DCM. The organic layer was dried over anhydrous MgSO$_4$, concentrated in vacuo to get the desired product D19 in 2.85 g. LCMS [MH+] 231@0.83 min (5 min run)

Description D20 (D20)

1,1-dimethylethyl 3-(methyloxy)-4-[(phenylcarbonyl)amino]-1-piperidinecarboxylate

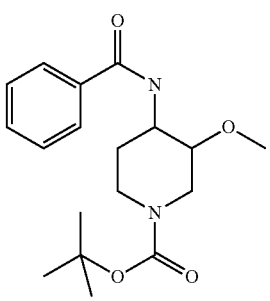 [SMILES: COC1CN(C(=O)OC(C)(C)C)CCC1NC(=O)c1ccccc1]

To a solution of 1,1-dimethylethyl 4-amino-3-(methyloxy)-1-piperidinecarboxylate D19 (2.85 g) in DCM (100 ml) was added triethylamine (5.2 ml, 37.2 mmol), and benzoyl chloride (2.2 ml, 18.6 mmol) at room temperature. The reaction mixture was stirred at room temperature for 4 hours. The resulting mixture was poured into water and extracted with DCM. The organic layer was dried over anhydrous MgSO$_4$, concentrated in vacuo to get the desired product D20 as an oil in 4.0 g. LCMS [MH+] 335@1.56 and 1.61 min (isomers seen) (5 min run)

Description 21 (D21)

N-[3-(methyloxy)-4-piperidinyl]benzamide

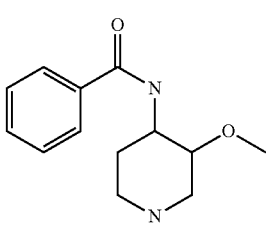 [SMILES: COC1CNCCC1NC(=O)c1ccccc1]

To a solution of 1,1-dimethylethyl 3-(methyloxy)-4-[(phenylcarbonyl)amino]-1-piperidinecarboxylate D20 (4.0 g) in HCl/1,4-dioxane (30 ml) was stirred at room temperature for overnight. The resulting mixture was dissolved in water (50 ml) and basified with sodium hydroxide to pH 10.0 then extracted with DCM (3×100 ml). The organic layer was dried over anhydrous MgSO$_4$, concentrated in vacuo to desired product D21 as an oil in 500 mg. LCMS [MH+] 235@1.17 and 1.19 (isomers) (5 min run)

Description 22 (D22)

1,1-dimethylethyl methyl[1-(5-methyl-7H-pyrrolo[2,3-d]pyrimidin-4-yl)-4-piperidinyl]carbamate

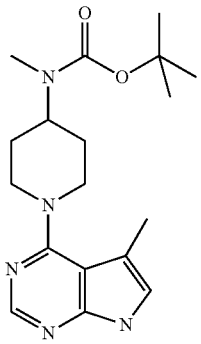 [SMILES: Cc1c[nH]c2ncnc(N3CCC(N(C)C(=O)OC(C)(C)C)CC3)c12]

A mixture of 4-chloro-5-methyl-7H-pyrrolo[2,3-d]pyrimidine D4 (1 g), 1,1-dimethylethyl methyl(4-piperidinyl)carbamate (1.918 g, 8.95 mmol, commercially available from e.g. Fluorochem, Apollo or Butt Park) and N,N-diisopropylethylamine (2.61 mL, 14.92 mmol) was heated at 150° C. for 20 minutes. LC/MS showed incomplete reaction. Further NMP (2 mL) and DIPEA (1.3 mL) was added. The mixture was heated at 150° C. for 20 minutes. The mixture was partitioned between ethyl acetate (70 mL) and water (60 mL) and the organic phase washed with water (2×60 mL) and brine (50 mL). It was dried (MgSO$_4$), filtered and the solvent removed in vacuo. The crude material was purified by silica chromatography, eluting 50-100% EtOAc in isohexane. The desired fractions collected and the solvent has been evaporated to give the desired product D22 in 0.793 g as a white solid. LCMS [M+H]+345.87@0.88 min (2 min run)

Description 23 (D23)

N-methyl-1-(5-methyl-7H-pyrrolo[2,3-d]pyrimidin-4-yl)-4-piperidinamine hydrochloride

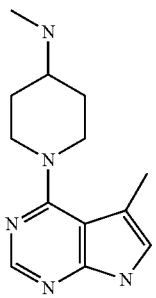 [SMILES: CNC1CCN(c2ncnc3[nH]cc(C)c23)CC1]

4M HCl in 1,4-Dioxane (6 mL) was added to 1,1-dimethylethyl methyl[1-(5-methyl-7H-pyrrolo[2,3-d]pyrimidin-4-yl)-4-piperidinyl]carbamate D22 (0.793 g) and the mixture stirred for 2 hours. The mixture was filtered under vacuum. The solid was washed with dioxane and Et$_2$O. The white powder was dried under vacuum all the night to give the desired product D23 in 0.6479 g. LCMS [M+H]+ 246.16@1.58 min (5 min run)

Description 24 (D24)

1,1-dimethylethyl {1-[5-bromo-7-(phenylsulfonyl)-7H-pyrrolo[2,3-d]pyrimidin-4-yl]-4-piperidinyl}methylcarbamate

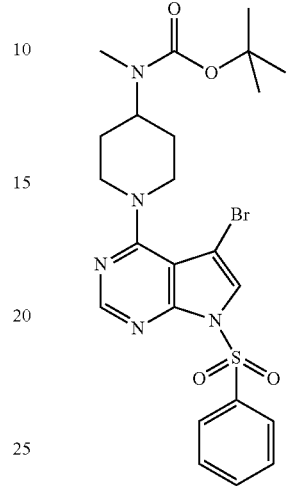

A mixture of 5-bromo-4-chloro-7-(phenylsulfonyl)-7H-pyrrolo[2,3-d]pyrimidine D5 (1.5 g), 1,1-dimethylethyl methyl(4-piperidinyl)carbamate (1.294 g, 6.04 mmol, commercially available from e.g Fluorochem, Apollo, or Astatech) and N,N-diisopropylethylamine (1.758 mL, 10.06 mmol) was heated at 150° C. for 20 min. Crude product needs to be purified by silica chromatography eluting with 10-50% EtOAc in isohexane. The fractions have been collected and the solvent has been evaporated to give the product D24 in 0.763 g. LC/MS [M+H]+549.71/551.79@1.50 min (2 min run)

Description 25 (D25)

1-[5-bromo-7-(phenylsulfonyl)-7H-pyrrolo[2,3-d]pyrimidin-4-yl]-N-methyl-4-piperidinamine

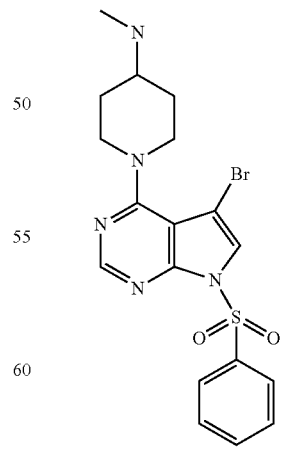

Was synthesised according to the methods described below
a) 4 M HCl in 1,4-Dioxane (20 mL) was added to 1,1-dimethylethyl {1-[5-bromo-7-(phenylsulfonyl)-7H- pyrrolo[2,3-d]pyrimidin-4-yl]-4-
piperidinyl}methylcarbamate D24 (0.52 g) and stirred
for 2 hours. The mixture was filtrated under vacuum. The
solid was washed with dioxane and Et₂O. The white
powder was dried under vacuum all the night to give the
product D25 in 0.1919 g. LCMS [M+H]+449.91/
451.93@2.55 min (5 min run).

b) 4 M HCl in 1,4-Dioxane (6 mL) was added to 1,1-
dimethylethyl {1-[5-bromo-7-(phenylsulfonyl)-7H-
pyrrolo[2,3-d]pyrimidin-4-yl]-4-
piperidinyl}methylcarbamate D24 (150 mg) and stirred
for 2 hours. The mixture was filtrated under vacuum. The
solid was washed with dioxane and Et₂O. The white
powder was dried under vacuum overnight to give the
product D25 in 0.0974 g. LCMS [M+H]+449.93/
451.93@ 2.56 min (5 min run)

Description 26 (D26)

N-{1-[5-bromo-7-(phenylsulfonyl)-7H-pyrrolo[2,3-
d]pyrimidin-4-yl]-4-piperidinyl}-N-methyl-4-pyridi-
necarboxamide

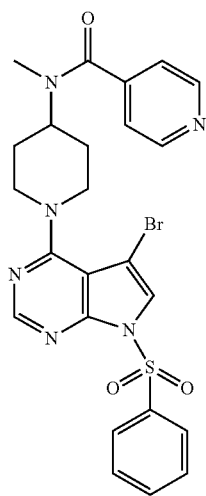 [SMILES: CN(C(=O)c1ccncc1)C1CCN(c2ncnc3c2c(Br)cn3S(=O)(=O)c2ccccc2)CC1]

4-pyridinecarboxylic acid (30.3 mg, 0.247 mmol) was dis-
solve in N,N-Dimethylformamide (DMF) (3 mL) under
argon flow. HATU (86 mg, 0.226 mmol) was added. After 30
minutes of stirring, 1-[5-bromo-7-(phenylsulfonyl)-7H-pyr-
rolo[2,3-d]pyrimidin-4-yl]-N-methyl-4-piperidinamine D25
(100 mg) was added. After 20 minutes of stirring, DIPEA
(0.144 mL, 0.822 mmol) was added. The mixture was stirred
at room temperature under argon flow for all the night. DCM
(10 mL) has been added to the mixture. The work-up has been
done with 2×10 mL of Na₂CO₃, 10 mL of brine. The organic
layer was filtrated by a phase separator and put under vacuo to
remove the solvent. The crude material was purified by silica
chromatography eluting by a gradiant of solvent: 0-5% of
MeOH in DCM. The fractions were collected and the solvent
has been evaporated to give the product D26 in 41 mg. LCMS
[M+H]+555.01/557.03 g 2.64 min (5 min run)

Description 27 (D27)

N-{1-[5-(1-methyl-4H-pyrazol-4-yl)-7-(phenylsulfo-
nyl)-7H-pyrrolo[2,3-d]pyrimidin-4-yl]-4-
piperidinyl}benzamide

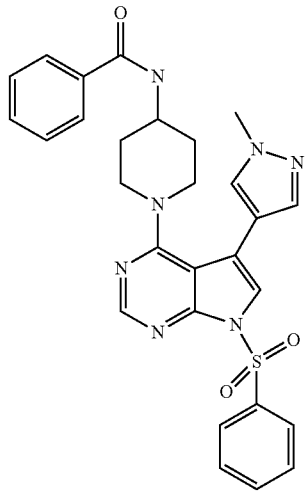 [SMILES: Cn1cc(-c2cn(S(=O)(=O)c3ccccc3)c3ncnc(N4CCC(NC(=O)c5ccccc5)CC4)c23)cn1]

N-{1-[5-bromo-7-(phenylsulfonyl)-7H-pyrrolo[2,3-d]py-
rimidin-4-yl]-4-piperidinyl}benzamide D6 (400 mg), 1-me-
thyl-4-(4,4,5,5-tetramethyl-1,3,2-dioxaborolan-2-yl)-1H-
pyrazole (185 mg, 0.89 mmol, commercially available from
Maybridge, Sigma-Aldrich and Fluorochem), potassium
phosphate trihydrate (590 mg, 2.22 mmol), palladium tetrakis
(26 mg, 0.022 mmol) were dissolved in 1,4-dioxane (10 ml)
and water (2 ml) and stirred under nitrogen at 90° C. over-
night. Cooled to room temperature and the solvent removed in
vacuo. Water (30 ml) was added and extracted with EtOAc
(3×30 ml). The combined extracts were washed with brine
and dried over MgSO₄, concentrated to give crude product
which was purified by silica gel column eluting with EtOAc
to give 160 mg of desired product D27. LCMS [MH+]
542.2@1.56 min (5 min run)

Description 28 (D28)

N-{1-[5-(3-furanyl)-7-(phenylsulfonyl)-7H-pyrrolo
[2,3-d]pyrimidin-4-yl]-4-piperidinyl}benzamide

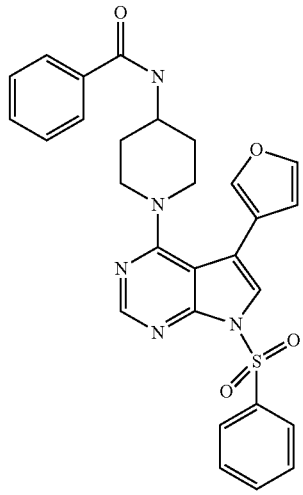 [SMILES: O=C(NC1CCN(c2ncnc3c2c(-c2ccoc2)cn3S(=O)(=O)c2ccccc2)CC1)c1ccccc1]

N-{1-[5-bromo-7-(phenylsulfonyl)-7H-pyrrolo[2,3-d]pyrimidin-4-yl]-4-piperidinyl}benzamide D6 (450 mg), 2-(3-furanyl)-4,4,5,5-tetramethyl-1,3,2-dioxaborolane (240 mg, 1.245 mmol, commercially available from e.g. Maybridge, Sigma-Aldrich or Apollo), potassium phosphate trihydrate (660 mg, 2.5 mmol), palladium tetrakis (30 mg, 0.026 mmol) were dissolved in 1,4-dioxane (20 ml) and water (4 ml) and stirred under nitrogen at 90° C. overnight. Cooled to room temperature, solvent removed in vacuo, water (150 ml) was added extracted with EtOAc (3×150 ml). The combined extracts were washed with brine and dried over MgSO₄, concentrated to give crude product which was purified by silica gel column eluting with pet eth/EtOAc 1:1 to give 60 mg of desired product D28. LCMS [MH+] 528.2@1.88 min (5 min run)

Description 29 (D29)

(E)-(1-{[(1,1-dimethylethy)oxy]carbonyl}-4-oxo-3-piperklinylidene) sodium methanolate

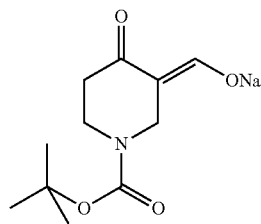

Sodium (1.2 g, 50 mmol) was dissolved in diethyl ether (200 mL) and then ethanol (5 ml) was added to the reaction. The reaction mixture was cooled to 5° C. then ethyl formate (5.6 g, 75 mmol) was added dropwise and then 1,1-dimethylethyl 4-oxo-1-piperidinecarboxylate (10 g, 50 mmol, commercially available from e.g. Sigma-Aldrich, Fluka or Apollo) was added. The reaction mixture was stirred for 6 hours. The yellow solid formed was filtered and washed with diethyl ether and dried in vacuo to give the desired product D29 in 6.8 g. LCMS [M-100-23]+128.1 @1.14 min (5 min run)

Description 30 (D30)

1,1-dimethylethyl (3E)-3-[(methyloxy)methylidene]-4-oxo-1-piperidinecarboxylate

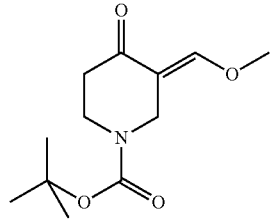 [SMILES: CO/C=C1\CN(C(=O)OC(C)(C)C)CCC1=O]

(E)-(1-{[(1,1-dimethylethyl)oxy]carbonyl}-4-oxo-3-piperidinylidene)sodium methanolate D29 (4 g) was dissolved in acetone (30 mL) and then potassium carbonate (4.4 g, 32 mmol) was added. Dimethylsulfate (2.3 g, 17.6 mmol) was added and the reaction mixture heated to 65° C. for 6 hours. Solvent removed and Ethyl acetate (excess) was added, organics were washed with water (3×) and brine, dried with MgSO₄, filtered and concentrated to obtain a yellow oil of desired product D30 in 1.8 g. LCMS [M-56+H] 186.1, [M-100+H] 142.1@1.52 min (5 min run)

Description 31 (D31)

1,1-dimethylethyl 3-[(methyloxy)methyl]-4-oxo-1-piperidinecarboxylate

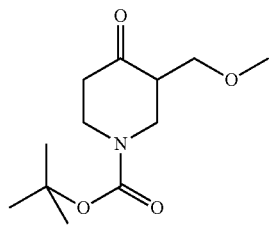 [SMILES: COCC1CN(C(=O)OC(C)(C)C)CCC1=O]

1,1-dimethylethyl (3E)-3-[(methyloxy)methylidene]-4-oxo-1-piperidinecarboxylate D30 (1.5 g) was dissolved in methanol (30 ml), and then 5% Pd/C (1 g) was added. The reaction mixture was hydrogenated at atmospheric pressure for 6 hours. Then the Pd/C was removed by filtration and the solution was evaporated in vacuo to afford the desired product D31 as a pale yellow oil in 1.2 g. LCMS [M-56+H] 188.1@1.53 min (5 min run)

Description D32 (D32)

1,1-dimethylethyl (4Z)-4-[(methyloxy)imino]-3-[(methyloxy)methyl]-1-piperidinecarboxylate

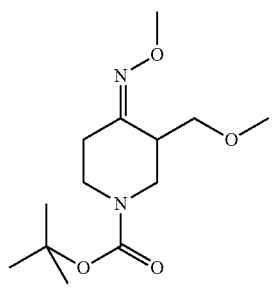 [SMILES: COCC1CN(C(=O)OC(C)(C)C)CC/C1=N/OC]

1,1-dimethylethyl 3-[(methyloxy)methyl]-4-oxo-1-piperidinecarboxylate D31 (1.2 g) and hydroxylamine hydrochloride (410 mg, 4.9 mmol) were dissolved in ethanol (60 ml). The reaction mixture was heated to 78° C. for 4 hours. Solvent was removed and dichloromethane (excess) was added. The organic layer was washed with water (3×), brine, collected and solvent removed to afford a yellow oil of the desired product D32 in 1.3 g. LCMS [M-56+H] 217.1@ 1.68 min (5 min run)

Description 33 (D33)

1,1-dimethylethyl 4-amino-3-[(methyloxy)methyl]-1-piperidinecarboxylate

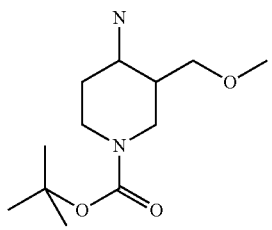 [SMILES: COCC1CN(C(=O)OC(C)(C)C)CCC1N]

1,1-dimethylethyl (4Z)-4-[(methyloxy)imino]-3-[(methyloxy)methyl]-1-piperidinecarboxylate D32 (1.2 g) was dissolved in methanol (40 ml), raney-nickel (0.6 g) was added under nitrogen. The reaction mixture was then hydrogenated at atmospheric pressure for 16 hours. The raney-nickel was filtered off and the solution was evaporated in vacuo to afford a yellow oil of desired product D33 in 0.7 g. LCMS [M+H] 245.2 [M-56+H] 189.1@1.36 min (5 min run)

Description 34 (D34)

1,1-dimethylethyl 3-[(methyloxy)methyl]-4-[(phenylcarbonyl)amino]-1-piperidinecarboxylate

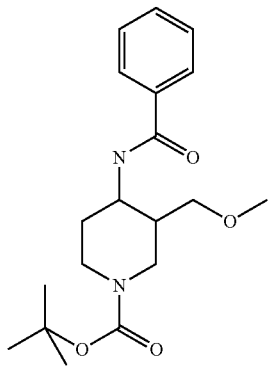 [SMILES: COCC1CN(C(=O)OC(C)(C)C)CCC1NC(=O)c1ccccc1]

1,1-dimethylethyl 4-amino-3-[(methyloxy)methyl]-1-piperidinecarboxylate D33 (0.7 g), and benzoyl chloride (490 mg, 3.5 mmol, commercially available from e.g. Sigma-Aldrich, Fluka or Fisher) were dissolved in dichloromethane (30 ml) and then triethylamine (1.3 ml, 8.7 mmol) was added. The reaction mixture was stirred at room temperature for 18 hours, then washed with water (2×), brine, dried with MgSO$_4$, filtered and solvent removed to obtain a yellow oil of crude product which was purified by column chromatography on silica gel eluting with pet eth/EA (2/1) to give clean desired product D34 as a yellow oil in 0.8 g. LCMS [M-56+H] 293.1@1.62 min (5 min run)

Description 35 (D35)

N-{3-[(methyloxy)methyl]-4-piperidinyl}benzamide

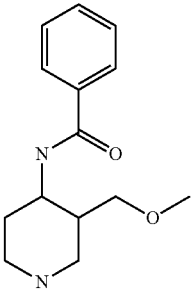 [SMILES: COCC1CNCCC1NC(=O)c1ccccc1]

1,1-dimethylethyl 3-[(methyloxy)methyl]-4-[(phenylcarbonyl)amino]-1-piperidinecarboxylate D34 (0.8 g) was dissolved in dichloromethane (25 ml). Trifluoroacetic acid (10 ml) was then added dropwise at room temperature. The reaction mixture was then stirred at room temperature for 3 hours, solvent was removed. A light yellow oil was obtained of desired product D35 in 0.6 g. LCMS [M+H] 249.1@1.20 min (5 min run)

Description 36 (D36)

1-(2-chloroethyl)pyrrolidine

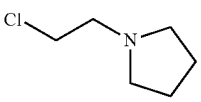

A solution of 2-(1-pyrrolidinyl)ethanol (9.5 g, 82.5 mmol) and thionyl chloride (11 ml) in CHCl$_3$ (50 ml) were refluxed for 1 hour. The reaction mixture was concentrated to give 9.2 g of a black solid of desired product D36. LCMS [MH+] 134.1@1.25 min (5 min run)

Description 37 (D37)

Methyl 3-{[2-(1-pyrrolidinyl)ethyl]oxy}benzoate

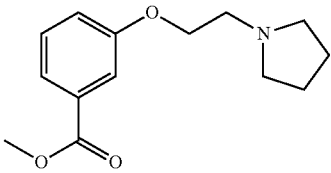 [SMILES: COC(=O)c1cccc(OCCN2CCCC2)c1]

A solution of 1-(2-chloroethyl)pyrrolidine D36 (9.2 g) and methyl 3-hydroxybenzoate (12.5 g, 82 mmol) and potassium iodide (13.68 g, 82 mmol) and potassium carbonate (11.37 g, 82 mmol) in acetone (200 ml) was refluxed for 2 days. The reaction was filtered and concentrated to give crude product which was purified by chromatography on silica gel eluting with pet eth/EtOAc 5/1 and EtOAc and MeOH to give 1.6 g of desired product D37 as a brown product. LCMS [MH+] 250.1 g 1.53 min (5 min run)

Description 38 (D38)

3-{[2-(1-pyrrolidinyl)ethyl]oxy}benzoic acid

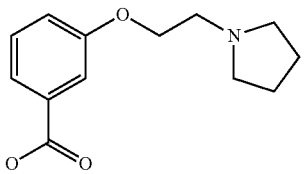 [SMILES: O=C(O)c1cccc(OCCN2CCCC2)c1]

A solution of methyl 3-{[2-(1-pyrrolidinyl)ethyl]oxy}benzoate D37 (1.6 g) and sodium hydroxide (708 mg, 18.2 mmol) in MeOH (50 ml) and water (10 ml) was refluxed for 18 hours. The reaction was concentrated and water added and acidified to pH3 with 2M HCl solution. The reaction was concentrated and was added MeOH and was filtered, concentrated to give a brown solid of desired product D38 in 1.5 g. LCMS [MH+] 236.1@0.96 min (5 min run)

Description 39 (D39)

4,5-dichloro-1H-pyrrolo[2,3-d]pyrimidine

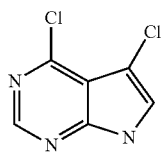 [SMILES: Clc1c[nH]c2ncnc(Cl)c12]

4-chloro-1H-pyrrolo[2,3-d]pyrimidine (1 g, 6.5 mmol, commercially available from e.g. Sigma-Aldrich, Apollo or Alfa Aesar) was dissolved in DCM (30 ml) and then NCS (1.04 g, 7.8 mmol) was added. The reaction mixture was stirred at room temperature for 16 hours, and then heated at 60° C. for 22 hours. After cooling a light yellow solid was obtained by filtration of the desired product in 1.2 g. LCMS [MH+] 188.0@1.42 min (5 min run)

Description 40 (D40)

4,5-dichloro-7-(phenylsulfonyl)-7H-pyrrolo[2,3-d]pyrimidine

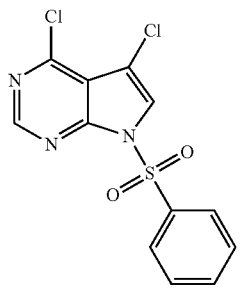 [SMILES: O=S(=O)(c1ccccc1)n1cc(Cl)c2c(Cl)ncnc21]

To a solution of 4,5-dichloro-1H-pyrrolo[2,3-d]pyrimidine D39 (1 g) in DMF (20 ml) at 0° C. was added sodium hydride (60% w/w in mineral oil, 255 mg, 6.4 mmol) and the mixture stirred for 20 mins. Phenylsulfonyl chloride (1.31 g, 7.4 mmol) was the added dropwise and the reaction mixture was kept in a cool bath for 15 hours. The mixture was poured into water (40 ml), and the precipitate was filtered, washed with water and Et₂O, dried in a vacuum to give the desired product D40 in 1.62 g as an ashen solid. LCMS [MH+] 329.9@1.77 min (5 min run)

Description 41 (D41)

N-{1-[5-chloro-7-(phenylsulfonyl)-7H-pyrrolo[2,3-d]pyrimidin-4-yl]-4-piperidinyl}benzamide

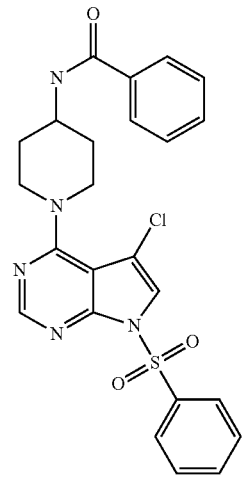 [SMILES: O=C(NC1CCN(c2ncnc3c2c(Cl)cn3S(=O)(=O)c2ccccc2)CC1)c1ccccc1]

4,5-dichloro-7-(phenylsulfonyl)-7H-pyrrolo[2,3-d]pyrimidine D40 (400 mg) and N-4-piperidinylbenzamide (300 mg, 1.46 mmol) were dissolved in NMP (4 ml), then N,N-diisopropylethylamine (315 mg, 2.44 mmol) was added dropwise. The reaction was stirred at room temperature for 16 hours then poured into water extracted with EtOAc (2×100 ml). Organic layer was washed with water (4×30 ml), brine (50 ml), dried with MgSO₄, filtered and solvent removed. Yellow solid obtained was purified by flash chromatography on silica gel eluting with pet eth/ethyl acetate 3/1 to give the desired product D41 in 260 mg as a yellow solid. LCMS [MH+] 496.0@1.54 min (5 min run)

Description 42 (D42)

4-chloro-1H-pyrrolo[2,3-d]pyrimidine-5-carbonitrile

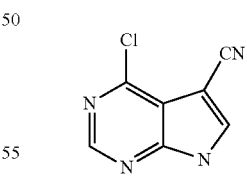

To a solution of anhydrous THF (40 ml) containing 5-Bromo-4-chloro-7H-pyrrolo[2,3-c]pyrimidine D3 (1 g) was added nBu-Li (2.5M, 5.2 ml, 12.9 mmol) dropwise at −78° C. under nitrogen. After this addition the resulting solution was stirred for 1 hour at −78° C. before adding 4-methylbenzenesulfonyl cyanide (935 mg, 5.2 mmol) and the resulting solution stirred for 1 hour at −78° C. and then allowed to warm up to room temperature overnight. The reaction was quenched with a saturated NH₄Cl solution at 0° C., extracted with EtOAc (100 ml) and organic layer was washed with 5% NaHCO₃ solution, dried Na₂SO₄, filtered and concentrated in vacuo to afford a yellow solid. Purified by flash chromatography on silica gel eluting with Pet Eth/EtOAc 1/2 to give the desired product D42 as a yellow solid in 350 mg. LCMS [MH+] 179.0 @1.17 min (5 min run)

Description 43 (D43)

4-chloro-7-({[2-(trimethylsilyl)ethyl]oxy}methyl)-7H-pyrrolo[2,3-d]pyrimidine-5-carbonitrile

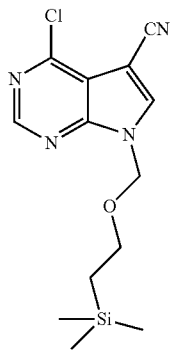 [SMILES: C[Si](C)(C)CCOCn1cc(C#N)c2c(Cl)ncnc21]

4-chloro-1H-pyrrolo[2,3-d]pyrimidine-5-carbonitrile D42 (60 mg) and potassium carbonate (282 mg, 2.04 mmol) were dissolved in DMF (6 ml), {2-[(chloromethyl)oxy]ethyl}(trimethyl)silane (69 mg, 0.41 mmol) was added dropwise. The reaction mixture was stirred at R.T. for 16 hours. The reaction mixture was poured onto water (30 ml), extracted with EtOAc (60 ml). Organic layer was washed with water (3×20 ml), brine (20 ml), dried (Na₂SO₄), filtered and concentrated in vacuo to obtain a yellow oil of desired product D43 in 105 mg. LCMS [MH+] 308.9@1.83 min (5 min run)

Description 44 (D44)

N-{1-[5-cyano-7-({[2-(trimethylsilyl)ethyl]oxy}methyl)-7H-pyrrolo[2,3-d]pyrimidin-4-yl]-4-piperidinyl}benzamide

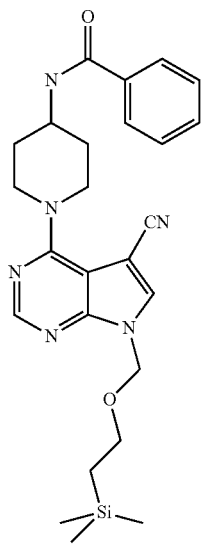 [SMILES: C[Si](C)(C)CCOCn1cc(C#N)c2c(N3CCC(NC(=O)c4ccccc4)CC3)ncnc21]

4-chloro-7-({[2-(trimethylsilyl)ethyl]oxy}methyl)-7H-pyrrolo[2,3-d]pyrimidine-5-carbonitrile D43 (100 mg) and N-4-piperidinylbenzamide (86 mg, 0.42 mmol, commercially available from e.g. Fluorochem, Alfa Aesar and Apollo) were dissolved in NMP and then N,N-diisopropylethylamine was added dropwise. The reaction mixture was carried out in the microwave at 120° C. for 45 minutes. The reaction mixture was poured onto water extracted with EtOAc (2×60 ml). Organic layers were washed water (3×20 ml), brine (30 ml), dried (MgSO₄), filtered and solvent removed. Crude product obtained was purified by flash chromatography on silica gel eluting with Pet Eth/EtOAc 3/1-2/1 to give the desired product D44 in 69 mg. LCMS [MH+] 477.2@1.80 min (5 min run)

Description 45 (D45)

ethyl 3-hydroxybenzoate

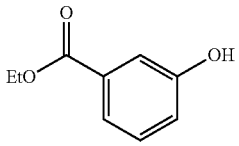 [SMILES: CCOC(=O)c1cccc(O)c1]

To a solution of 3-hydroxybenzoic acid (10 g, 72.4 mmol) in Ethanol (150 mL) stirred under nitrogen was added H₂SO₄ (3.86 mL, 72.4 mmol). The reaction mixture was refluxed at 85° overnight. The reaction mixture was concentrated and partitioned between ethyl acetate 100 mL and water 30 mL. The organic layers were combined and dried over Na₂SO₄, evaporated in vacuo to give the crude product D45 in 11 g. LCMS Retention time=1.45 mins, [M+H]⁺167 (5 min run)

Description 46 (D46)

ethyl 3-[(2-bromoethyl)oxy]benzoate

To a solution of ethyl 3-hydroxybenzoate D45 (5 g) and K₂CO₃ (12.48 g, 90 mmol) in Acetonitrile (150 mL) stirred under nitrogen was added 1,2-dibromoethane (33.9 g, 181 mmol). The reaction mixture was stirred at 60° C. overnight. The reaction mixture was filtered, concentrated to give the crude as clear oil. The crude was purified to give the expected product D46 in 4.2 g, eluting with Petroleum oil/EtOAc=3/1. LCMS Retention time=1.76 mins, [M+H]⁺273 (5 min run)

Description 47 (D47)

ethyl 3-{[2-(4-morpholinyl)ethyl]oxy}benzoate

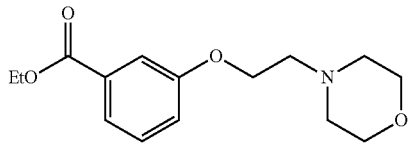

To a solution of ethyl 3-[(2-bromoethyl)oxy]benzoate D46 (100 mg), morpholine (44.7 mg, 0.513 mmol) in Acetonitrile (2 mL) stirred under nitrogen at 25° C. was added $K_2CO_3$ (106 mg, 0.769 mmol). The reaction mixture was stirred at 60° overnight. The mixture was filtered and the filtrate was concentrated in vacuo to give 98 mg of the crude product D47 without more purification. LCMS Retention time=1.57 mins, $[M+H]^+$ 280 (5 min run)

Description 48 (D48)

ethyl 3-({2-[(3R)-3-fluoro-1-pyrrolidinyl]ethyl}oxy)benzoate

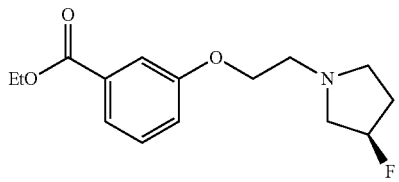

To a solution of ethyl 3-[(2-bromoethyl)oxy]benzoate D46 (200 mg) and (3R)-3-fluoropyrrolidine (129 mg, 1.025 mmol) in Acetonitrile (10 ml) was added $K_2CO_3$ (213 mg, 1.538 mmol). The reaction mixture was stirred at 60° C. overnight. The reaction mixture was filtered and the filtrate was concentrated to give the expected product D48 in 220 mg. LCMS: rt=1.63 min, M+H=282.1 (5 min run)

Description 49 (D49)

ethyl 3-{[2-(3,3-difluoro-1-pyrrolidinyl)ethyl]oxy}benzoate

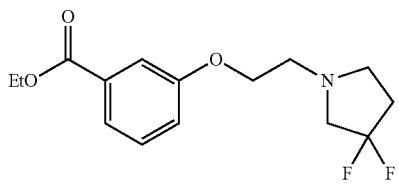

To a suspension of ethyl 3-[(2-bromoethyl)oxy]benzoate D46 (476 mg) and potassium carbonate (481 mg, 3.48 mmol) in Acetonitrile (20 mL) stirred at 20° C. was added 3,3-difluoropyrrolidine (250 mg, 1.741 mmol). The reaction mixture was stirred at 70° C. for 36 h. After cooled to room temperature the mixture was filtrated and the filtrate was concentrated. The crude product was added to a silica gel column and was eluted with Hexane/EtOAc/TEA in ratio 50/50/0.5. Fractions isolated and solvent evaporated to afford the title product D49 in 400 mg as a yellow oil. LCMS Retention time=1.20 mins, $[M+H]^+$ 300 (5 min run)

Description 50 (D50)

ethyl 3-({2-[(2R)-2-methyl-1-pyrrolidinyl]ethyl}oxy)benzoate

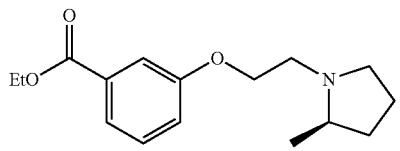 [SMILES: CCOC(=O)c1cccc(OCCN2CCC[C@H]2C)c1]

To a suspension of (2R)-2-methylpyrrolidine (300 mg, 3.52 mmol) and potassium carbonate (974 mg, 7.05 mmol) in Acetonitrile (20 mL) stirred at room temperature was added ethyl 3-[(2-bromoethyl)oxy]benzoate D46 (962 mg). The reaction mixture was stirred at 80° C. for 24 hours. After cooled to room temperature the mixture was filtrated and the filtrate was concentrated. The crude product was added to a silica gel column and was eluted with Hexane/EtOAc/TEA in ratio 50/50/0.5. The relevant fractions were isolated and solvent evaporated to afford the title compound D50 in 900 mg as a yellow oil. LCMS Retention time=1.09 mins, $[M+H]^+$ 278 (5 min run)

Description 51 (D51)

3-{[2-(4-morpholinyl)ethyl]oxy}benzoic acid

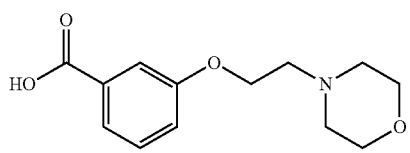 [SMILES: O=C(O)c1cccc(OCCN2CCOCC2)c1]

To the material of ethyl 3-{[2-(4-morpholinyl)ethyl]oxy}benzoate D47 (98 mg) was added HCl (0.5 mL, 16.46 mmol) at room temperature. The reaction was stirred at 100° for 2.5 hours. The mixture was concentrated in vacuo. To the residue was added 2 ml of ether and stirred for 0.5 hours, filtered. The filtrate was evaporated in vacuo to give the expected product D51 in 90 mg, as a white solid. LCMS Retention time=0.84 mins, $[M+H]^+$ 252 (5 min run)

Description 52 (D52)

3-({2-[(3R)-3-fluoro-1-pyrrolidinyl]ethyl}oxy)benzoic acid

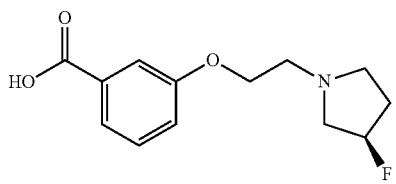 [SMILES: O=C(O)c1cccc(OCCN2CC[C@@H](F)C2)c1]

To the material of ethyl 3-({2-[(3R)-3-fluoro-1-pyrrolidinyl]ethyl}oxy)benzoate D48 (220 mg) was added HCl (0.3 ml, 9.87 mmol) at room temperature. The reaction was stirred at 100° for 2.5 hours. The mixture was concentrated in vacuo. To the residue was added 5 ml of ether and stirred 0.5 hours, filtered and the filtrate was evaporated in vacuo to give the expected product D52 in 160 mg. LCMS Retention time=0.90 mins, [M+H]$^+$254 (5 min run)

Description 53 (D53)

3-{[2-(3,3-difluoro-1-pyrrolidinyl)ethyl]oxy}benzoic acid

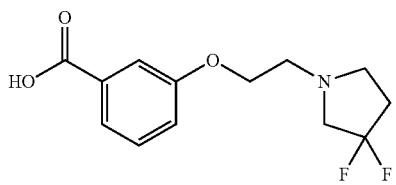 [SMILES: O=C(O)c1cccc(OCCN2CCC(F)(F)C2)c1]

To a solution of ethyl 3-{[2-(3,3-difluoro-1-pyrrolidinyl)ethyl]oxy}benzoate D49 (400 mg) in Methanol (20 mL) stirred at 20° C. was added a solution of lithium hydroxide (100 mg, 2.383 mmol) in water (5 mL). The reaction mixture was stirred at 80° C. for 12 hours. The solvent was removed and the residue was purified with combined flash. (Mobile Phase: A=0.05% TFA/H$_2$O, B=MeCN, 20% MeCN) to afford the title compound D53 in 200 mg, as a pale solid. LCMS Retention time=1.15 mins, [M+H]$^+$272 (5 min run)

Description 54 (D54)

3-({2-[(2R)-2-methyl-1-pyrrolidinyl]ethyl}oxy)benzoic acid

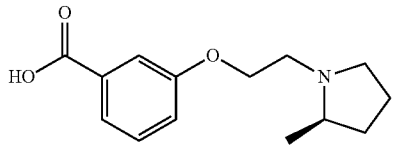 [SMILES: C[C@@H]1CCCN1CCOc1cccc(C(=O)O)c1]

To a solution of ethyl 3-({2-[(2R)-2-methyl-1-pyrrolidinyl]ethyl}oxy)benzoate D50 (900 mg) in Methanol (30 mL) stirred at 20° C. was added a solution of lithium hydroxide (200 mg, 4.77 mmol) in Water (6 mL). The reaction mixture was stirred at 80° C. overnight.

The solvent was removed and the residue was purified with combined flash. (Mobile Phase: A=0.05% TFA/H$_2$O, B=MeCN, 20% MeCN) to afford the title compound D54 in 300 mg, as a pale solid. LCMS Retention time=1.15 mins, [M+H]$^+$272 (5 min run)

Example 1 (E1)

N-[1-(7H-Pyrrolo[2,3-d]pyrimidin-4-yl)-4-piperidinyl]benzamide

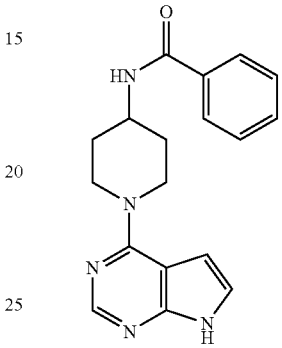

A mixture of 4-chloro-7H-pyrrolo[2,3-d]pyrimidine (0.15 g, 1.0 mmol) and N-4-piperidinylbenzamide (0.24 g, 1.200 mmol) in ethanol (3 mL) was microwaved at 150° C. for 20 minutes. The white solid appearing after cooling was filtered, washed with Et$_2$O then purified by MDAP using a high pH method to afford E1 (59 mg); $^1$H NMR (d6-DMSO) δ 11.60 (1H, brs), 8.29 (1H, d), 8.15 (1H, s), 7.84 (2H, dd), 7.52 (1H, m), 7.49 (2H, dd), 7.19 (1H, d), 6.65 (1H, d), 4.70 (2H, dt), 4.18 (1H, m), 3.24 (2H, dt), 1.91 (2H, m), 1.60 (2H, m), MS(ES+) 322 [M+H]$^+$.

Example 2 (E2)

3-(Methyloxy)-N-[1-(1H-pyrrolo[2,3-d]pyrimidin-4-yl)-4-piperidinyl]benzamide

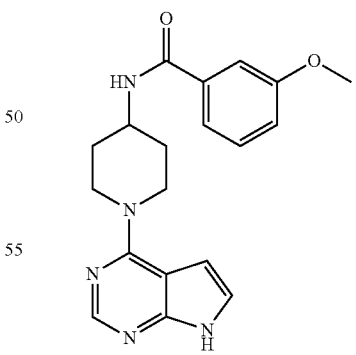

A mixture of 1-(7H-pyrrolo[2,3-d]pyrimidin-4-yl)-4-piperidinamine D2 (65 mg), 3-(methyloxy)benzoyl chloride (61.2 mg, 0.359 mmol) and N-methylmorpholine (0.1 mL, 0.897 mmol) in DMF (1.5 mL) was stirred at room temperature for 3 hours. The solvent was removed in vacuo. The crude mixture was purified by MDAP using a formic acid method to provide E2 (45 mg); $^1$H NMR (d6-DMSO) δ 11.60 (1H, brs), 8.25 (1H, d), 8.15 (1H, s), 7.45 (1H, dd), 7.35 (2H, m), 7.20 (1H, d), 7.06 (1H, dd), 6.62 (1H, d), 4.72 (2H, dt), 4.17 (1H, m), 3.32 (3H, s), 3.20 (2H, dt), 1.95 (2H, m), 1.60 (2H, m), MS(ES+) 352 [M+H]⁺.

Example 3 (E3)

3-(Dimethylamino)-N-[1-(1H-pyrrolo[2,3-d]pyrimidin-4-yl)-4-piperidinyl]benzamide

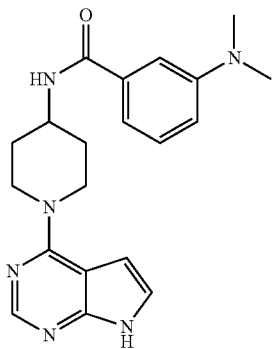 [SMILES: CN(C)c1cccc(C(=O)NC2CCN(c3ncnc4[nH]ccc34)CC2)c1]

To a mixture of 1-(7H-pyrrolo[2,3-d]pyrimidin-4-yl)-4-piperidinamine D2 (65.2 mg), 3-(dimethylamino)benzoic acid (49.6 mg, 0.300 mmol), HATU (137 mg, 0.360 mmol) and HOAt (24.5 mg, 0.180 mmol) in DMF (1.5 mL) was added DIPEA (252 μL, 1.440 mmol). The reaction mixture was stirred overnight at room temperature then the solvent was removed in vacuo. The crude mixture was purified by MDAP using a formic acid method to afford E3 (7 mg), ¹H NMR (d6-DMSO) δ 11.60 (1H, brs), 8.15 (2H, m), 7.25 (2H, m), 7.15 (2H, m), 6.85 (1H, dd), 6.62 (1H, d), 4.72 (2H, dt), 4.17 (1H, m), 3.20 (2H, dt), 2.91 (6H, s), 1.90 (2H, m), 1.60 (2H, m), MS(ES+) 365 [M+H]⁺.

Example 4 (E4)

4-(Dimethylamino)-N-[1-(1H-pyrrolo[2,3-d]pyrimidin-4-yl)-4-piperidinyl]benzamide

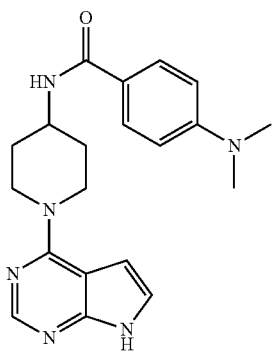 [SMILES: CN(C)c1ccc(C(=O)NC2CCN(c3ncnc4[nH]ccc34)CC2)cc1]

To a mixture of 1-(7H-pyrrolo[2,3-d]pyrimidin-4-yl)-4-piperidinamine D2 (65.2 mg), 4-(dimethylamino)benzoic acid (49.6 mg, 0.300 mmol), HATU (137 mg, 0.360 mmol) and HOAt (24.5 mg, 0.180 mmol) in DMF (1.5 mL) was added DIPEA (252 μL, 1.440 mmol). The reaction mixture was stirred overnight at room temperature then the solvent was removed in vacuo. The crude mixture was purified by MDAP using a formic acid method to afford E4 (41 mg), ¹H NMR (d6-DMSO) δ 11.67 (1H, brs), 8.15 (1H, d), 7.88 (1H, d), 7.70 (2H, dd), 7.17 (1H, d), 6.67 (2H, dd), 6.61 (1H, d), 4.70 (2H, dt), 4.15 (1H, m), 3.17 (2H, dt), 2.95 (6H, s), 1.88 (2H, m), 1.57 (2H, m), MS(ES+) 365 [M+H]⁺.

Example 5 (E5)

2-(Dimethylamino)-N-[1-(1H-pyrrolo[2,3-d]pyrimidin-4-yl)-4-piperidinyl]benzamide

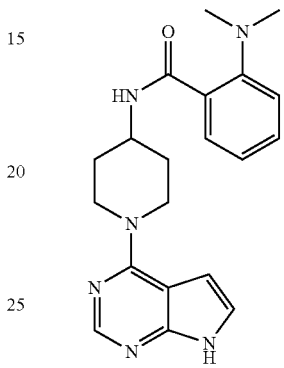

To a mixture of 1-(7H-pyrrolo[2,3-d]pyrimidin-4-yl)-4-piperidinamine D2 (65.2 mg), 2-(dimethylamino)benzoic acid (74.3 mg, 0.450 mmol), EDC (103 mg, 0.450 mmol) and HOAt (12.25 mg, 0.090 mmol) in DMF (1.5 mL) was added DIPEA (131 μL, 0.750 mmol). The reaction mixture was stirred overnight at room temperature then solvent was removed in vacuo. The crude mixture was purified by MDAP using a formic acid method to afford E5 (48.5 mg), ¹H NMR (d6-DMSO) δ 11.70 (1H, brs), 9.00 (1H, d), 8.15 (1H, s), 7.57 (1H, dd), 7.37 (1H, m), 7.19 (1H, d), 7.12 (1H, d), 7.02 (1H, m), 6.60 (1H, d), 4.60 (2H, dt), 4.15 (1H, m), 3.45 (2H, dt), 2.69 (6H, s), 1.97 (2H, m), 1.55 (2H, m), MS(ES+) 365 [M+H]⁺.

Example 6 (E6)

3-[(Dimethylamino)methyl]-N-[1-(1H-pyrrolo[2,3-d]pyrimidin-4-yl)-4-piperidinyl]benzamide, formic acid salt

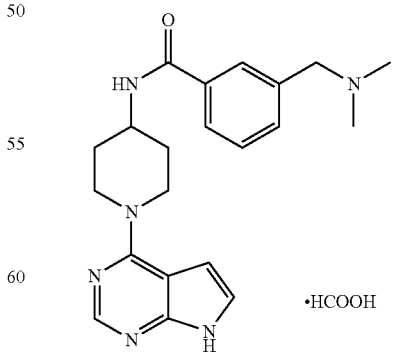

To a mixture of 1-(7H-pyrrolo[2,3-d]pyrimidin-4-yl)-4-piperidinamine D2 (65.2 mg), 3-[(dimethylamino)methyl]benzoic acid (81 mg, 0.450 mmol), EDC (103 mg, 0.450 mmol)

and HOAt (12.25 mg, 0.090 mmol) in DMF (1.5 mL) was added DIPEA (131 μL, 0.750 mmol). The reaction mixture was stirred overnight at room temperature then the solvent was removed in vacuo. The crude mixture was purified by MDAP using a formic acid method to afford E6 (40 mg), $^1$H NMR (d6-DMSO) δ 11.70 (1H, brs), 8.30 (1H, d), 8.15 (2H, s), 7.79 (1H, s), 7.75 (1H, dd), 7.40 (2H, m), 7.20 (1H, d), 6.60 (1H, d), 4.70 (2H, dt), 4.17 (1H, m), 3.42 (2H, s), 3.20 (2H, dt), 2.15 (6H, s), 1.90 (2H, m), 1.60 (2H, m), MS(ES+) 379 [M+H]$^+$.

Example 7 (E7)

3-(1-Pyrrolidinyl)-N-[1-(1H-pyrrolo[2,3-d]pyrimidin-4-yl)-4-piperidinyl]benzamide

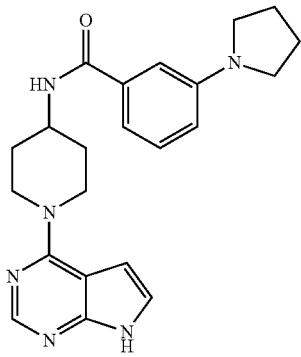 [SMILES: O=C(NC1CCN(c2ncnc3[nH]ccc23)CC1)c1cccc(N2CCCC2)c1]

To a mixture of 1-(7H-pyrrolo[2,3-d]pyrimidin-4-yl)-4-piperidinamine D2 (65.2 mg), 341-pyrrolidinyl)benzoic acid (57.4 mg, 0.300 mmol), HATU (137 mg, 0.360 mmol) and HOAt (24.50 mg, 0.180 mmol) in DMF (1.5 mL) was added DIPEA (252 μL, 1.440 mmol). The reaction mixture was stirred overnight at room temperature then the solvent was removed in vacuo. The crude mixture was purified by MDAP using a formic acid method to afford E7 (50 mg), $^1$H NMR (d6-DMSO) δ 11.70 (1H, brs), 8.17 (1H, s), 8.12 (1H, d), 7.20 (2H, m), 7.07 (1H, d), 6.97 (1H, s), 6.62 (2H, m), 4.70 (2H, dt), 4.17 (1H, m), 3.27 (4H, m), 3.18 (2H, dt), 1.95 (6H, m), 1.57 (2H, m), MS(ES+) 391 [M+H]$^+$.

Example 8 (E8)

3-(4-Morpholinyl)-N-[1-(1H-pyrrolo[2,3-d]pyrimidin-4-yl)-4-piperidinyl]benzamide

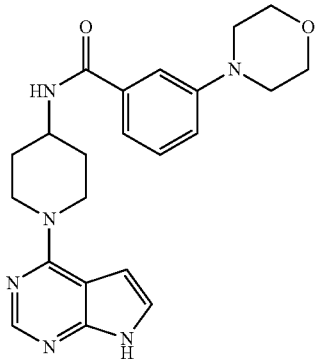 [SMILES: O=C(NC1CCN(c2ncnc3[nH]ccc23)CC1)c1cccc(N2CCOCC2)c1]

To a mixture of 1-(7H-pyrrolo[2,3-d]pyrimidin-4-yl)-4-piperidinamine D2 (65.2 mg), 3-(4-morpholinyl)benzoic acid (62.2 mg, 0.300 mmol), HATU (137 mg, 0.360 mmol) and HOAt (24.50 mg, 0.180 mmol) in DMF (1.5 mL) was added DIPEA (252 μL, 1.440 mmol). The reaction mixture was stirred overnight at room temperature then the solvent was removed in vacuo. The crude mixture was purified by MDAP using a formic acid method to afford E8 (45 mg); $^1$H NMR (d6-DMSO) δ 11.70 (1H, brs), 8.17 (2H, d), 7.35 (1H, s), 7.30 (2H, d), 7.20 (1H, d), 7.07 (1H, d), 6.60 (1H, d), 4.70 (2H, dt), 4.17 (1H, m), 3.72 (4H, t), 3.20 (2H, dt), 3.13 (4H, t), 1.90 (2H, m), 1.57 (2H, m), MS(ES+) 407 [M+H]$^+$.

Example 9 (E9)

N-[1-(1H-Pyrrolo[2,3-d]pyrimidin-4-yl)-4-piperidinyl]-2-pyridinecarboxamide

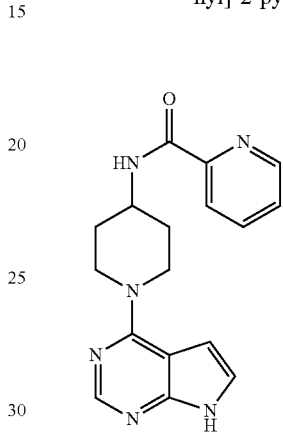

To a mixture of 1-(7H-pyrrolo[2,3-d]pyrimidin-4-yl)-4-piperidinamine D2 (65.2 mg), 2-pyridinecarboxylic acid (36.9 mg, 0.300 mmol), HATU (137 mg, 0.360 mmol) and HOAt (24.50 mg, 0.180 mmol) in DMF (1.5 mL) was added DIPEA (252 μL, 1.440 mmol). The reaction mixture was stirred overnight at room temperature then the solvent was removed in vacuo. The crude mixture was purified by MDAP using a formic acid method to afford E9 (23 mg), $^1$H NMR (d6-DMSO) δ 11.70 (1H, brs), 8.70 (1H, d), 8.65 (1H, d), 8.17 (1H, s), 8.05 (1H, d), 8.0 (1H, m), 7.60 (1H, m) 7.20 (1H, d) 6.60 (1H, d), 4.70 (2H, dt), 4.17 (1H, m), 3.20 (2H, dt), 1.90 (2H, m), 1.70 (2H, m), MS(ES+) 323 [M+H]$^+$.

Example 10 (E10)

N-[1-(1H-Pyrrolo[2,3-d]pyrimidin-4-yl)-4-piperidinyl]-3-pyridinecarboxamide

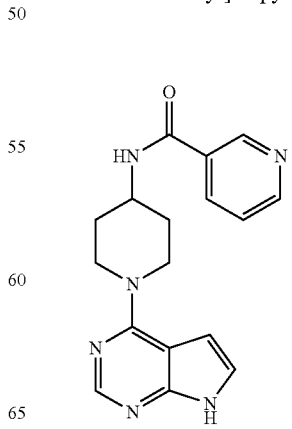

To a mixture of 1-(7H-pyrrolo[2,3-d]pyrimidin-4-yl)-4-piperidinamine D2 (100 mg), 3-pyridinecarboxylic acid (56.7 mg, 0.460 mmol), HATU (210 mg, 0.552 mmol) and HOAt (37.60 mg, 0.276 mmol) in DMF (2.3 mL) was added DIPEA (386 μL, 2.209 mmol). The reaction mixture was stirred at room temperature for 2 hours then the solvent was removed in vacuo. The crude mixture was purified by MDAP using a high pH method to afford E10 (113 mg), $^1$H NMR (d6-DMSO) δ 11.70 (1H, brs), 9.0 (1H, s), 8.70 (1H, d), 8.50 (1H, d), 8.17 (2H, m), 7.50 (1H, m), 7.17 (1H, d), 6.62 (1H, d), 4.70 (2H, dt), 4.17 (1H, m), 3.22 (2H, dt), 1.95 (2H, m), 1.55 (2H, m), MS(ES+) 323 [M+H]$^+$.

Example 11 (E11)

N-[1-(1H-Pyrrolo[2,3-d]pyrimidin-4-yl)-4-piperidinyl]-4-pyridinecarboxamide

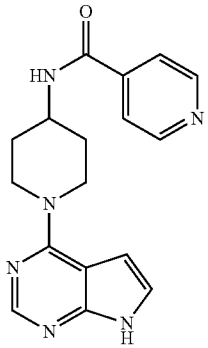 [SMILES: O=C(NC1CCN(c2ncnc3[nH]ccc23)CC1)c1ccncc1]

To a mixture of 1-(7H-pyrrolo[2,3-d]pyrimidin-4-yl)-4-piperidinamine D2 (100 mg), 4-pyridinecarboxylic acid (56.7 mg, 0.460 mmol), HATU (210 mg, 0.552 mmol) and HOAt (37.60 mg, 0.276 mmol) in DMF (2.3 mL) was added DIPEA (386 μL, 2.209 mmol). The reaction mixture was stirred at room temperature for 2 hours then the solvent was removed in vacuo. The crude mixture was purified by MDAP using a high pH method to afford E11 (75 mg), $^1$H NMR (d6-DMSO) δ 11.70 (1H, brs), 8.70 (2H, d), 8.57 (1H, d), 8.17 (1H, s), 7.72 (2H, d), 7.18 (1H, d), 6.60 (1H, d), 4.70 (2H, dt), 4.15 (1H, m), 3.20 (2H, dt), 1.90 (2H, m), 1.60 (2H, m), MS(ES+) 323 [M+H]$^+$.

Example 12 (E12)

2-Methyl-N-[1-(1H-pyrrolo[2,3-d]pyrimidin-4-yl)-4-piperidinyl]-4-pyridinecarboxamide

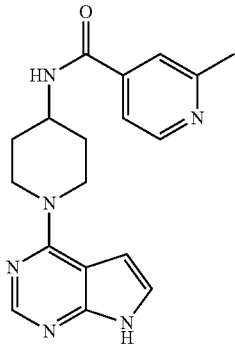 [SMILES: Cc1cc(C(=O)NC2CCN(c3ncnc4[nH]ccc34)CC2)ccn1]

To a mixture of 1-(7H-pyrrolo[2,3-d]pyrimidin-4-yl)-4-piperidinamine D2 (100 mg), 2-methyl-4-pyridinecarboxylic acid (63.1 mg, 0.460 mmol), HATU (210 mg, 0.552 mmol) and HOAt (37.60 mg, 0.276 mmol) in DMF (2.3 mL) was added DIPEA (386 μL, 2.209 mmol). The reaction mixture was stirred at room temperature for 2 hours then the solvent was removed in vacuo. The crude mixture was purified by MDAP using a high pH method to afford E12 (72 mg), $^1$H NMR (d6-DMSO) δ 11.70 (1H, brs), 8.55 (2H, m), 8.17 (1H, s), 7.62 (1H, s), 7.53 (1H, d), 7.18 (1H, d), 6.60 (1H, d), 4.70 (2H, dt), 4.15 (1H, m), 3.35 (3H, s), 3.25 (2H, dt), 1.90 (2H, m), 1.53 (2H, m), MS(ES+) 337 [M+H]$^+$.

Example 13 (E13)

N-[1-(1H-Pyrrolo[2,3-d]pyrimidin-4-yl)-4-piperidinyl]-4-pyridazinecarboxamide

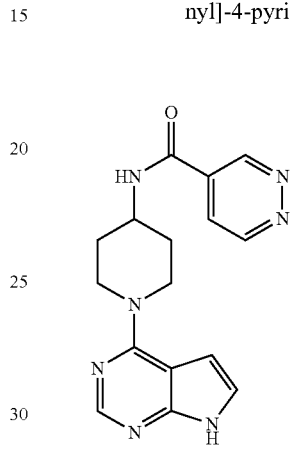

To a mixture of 1-(7H-pyrrolo[2,3-d]pyrimidin-4-yl)-4-piperidinamine D2 (100 mg), 4-pyridazinecarboxylic acid (57.1 mg, 0.460 mmol), HATU (210 mg, 0.552 mmol) and HOAt (37.60 mg, 0.276 mmol) in DMF (2.3 mL) was added DIPEA (386 μL, 2.209 mmol). The reaction mixture was stirred at room temperature for 2 hours then the solvent was removed in vacuo. The crude mixture was purified by MDAP using a formic acid method to afford E13 (44 mg), $^1$H NMR (d6-DMSO) δ 11.70 (1H, brs), 9.55 (1H, s), 9.42 (1H, d), 8.80 (1H, d), 8.17 (1H, s), 8.0 (1H, d), 7.20 (1H, d), 6.60 (1H, d), 4.70 (2H, dt), 4.15 (1H, m), 3.25 (2H, dt), 1.90 (2H, m), 1.60 (2H, m), MS(ES+) 324 [M+H]$^+$.

Example 14 (E14)

N-[1-(1H-Pyrrolo[2,3-d]pyrimidin-4-yl)-4-piperidinyl]-5-pyrimidinecarboxamide

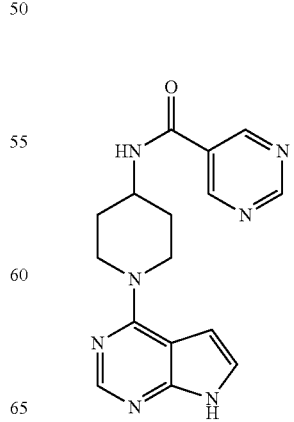

To a mixture of 1-(7H-pyrrolo[2,3-d]pyrimidin-4-yl)-4-piperidinamine D2 (65.2 mg), 5-pyrimidinecarboxylic acid (37.2 mg, 0.300 mmol), HATU (137 mg, 0.360 mmol) and HOAt (24.50 mg, 0.180 mmol) in DMF (1.5 mL) was added DIPEA (252 µL, 1.440 mmol). The reaction mixture was stirred at room temperature until reaction was complete then solvent was removed in vacuo. The crude mixture was purified by MDAP using a high pH method to afford E14 (21 mg); $^1$H NMR (d6-DMSO) δ 11.70 (1H, brs), 9.30 (1H, s), 9.15 (2H, s), 8.65 (1H, d), 8.17 (1H, s), 7.17 (1H, d), 6.60 (1H, d), 4.65 (2H, dt), 4.15 (1H, m), 3.25 (2H, dt), 1.90 (2H, m), 1.55 (2H, m), MS(ES+) 324 [M+H]$^+$.

Example 15 (E15)

2-(Methyloxy)-N-[1-(1H-pyrrolo[2,3-d]pyrimidin-4-yl)-4-piperidinyl]-4-pyridinecarboxamide

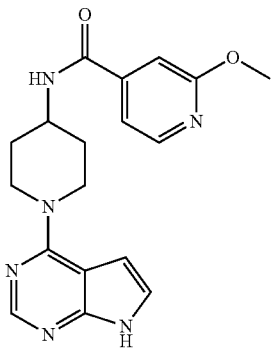 [SMILES: COc1cc(C(=O)NC2CCN(c3ncnc4[nH]ccc34)CC2)ccn1]

To a mixture of 1-(7H-pyrrolo[2,3-d]pyrimidin-4-yl)-4-piperidinamine D2 (65.2 mg), 2-(methyloxy)-4-pyridinecarboxylic acid (45.9 mg, 0.300 mmol), HATU (137 mg, 0.360 mmol) and HOAt (24.50 mg, 0180 mmol) in DMF (1.5 mL) was added DIPEA (252 µL, 1.440 mmol). The reaction mixture was stirred at room temperature for 3 hours then the solvent was removed in vacuo. The crude mixture was purified by MDAP using a high pH method to afford E15 (40 mg); $^1$H NMR (d6-DMSO) δ 11.70 (1H, brs), 8.50 (1H, d), 8.30 (1H, d), 8.17 (1H, s), 7.35 (1H, d), 7.20 (2H, d), 6.60 (1H, d), 4.67 (2H, dt), 4.15 (1H, m), 3.88 (3H, s), 3.20 (2H, dt), 1.90 (2H, m), 1.55 (2H, m), MS(ES+) 353 [M+H]$^+$.

Example 16 (E16)

5-Methyl-N-[1-(1H-pyrrolo[2,3-d]pyrimidin-4-yl)-4-piperidinyl]-3-isoxazolecarboxamide

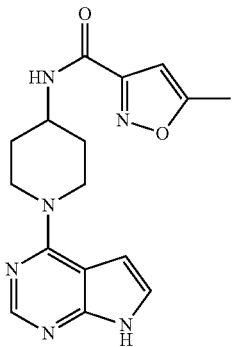

5-methyl-3-isoxazolecarbonyl chloride (0.029 g, 0.200 mmol) in DCM (1 mL) and DMF (0.5 mL) was added to a solution of 1-(7H-pyrrolo[2,3-d]pyrimidin-4-yl)-4-piperidinamine D2 (0.043 g) in DMF (1.5 mL) in the presence of polymer-supported morpholine (0.279 g, 0.600 mmol, loading 2.15 mmol/g). The reaction mixture was shaken overnight at room temperature. The morpholine resin was filtered off and washed with a DCM:DMF (1:1) mixture. The unreacted acid chloride was removed by filtration on a Si—NH$_2$ cartridge [Biotage] eluting with a DCM:DMF 1:1 mixture, and then the solvents were removed in vacuo. The crude mixture was purified by MDAP using a formic acid method to afford E16 (23.4 mg); $^1$H NMR (d6-DMSO) δ 11.70 (1H, brs), 8.64 (1H, d), 8.14 (1H, s), 7.18 (1H, d), 6.59 (1H, d), 6.52 (1H, s), 4.71 (2H, dt), 4.12 (1H, m), 3.15 (2H, dt), 2.44 (3H, s), 1.85 (2H, m), 1.60 (2H, m), MS(ES+) 326 [M+H]$^+$.

Example 17 (E17)

N-[1-(5-Methyl-1H-pyrrolo[2,3-d]pyrimidin-4-yl)-4-piperidinyl]benzamide

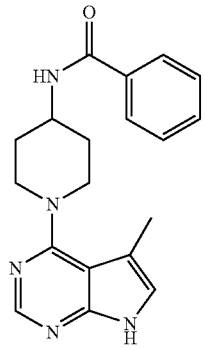 [SMILES: Cc1c[nH]c2ncnc(N3CCC(NC(=O)c4ccccc4)CC3)c12]

A mixture of 4-chloro-5-methyl-7H-pyrrolo[2,3-d]pyrimidine D4 (136 mg), N-4-piperidinylbenzamide (249 mg, 1.217 mmol) and DIPEA (0.354 mL, 2.029 mmol) in NMP (1 mL) was heated in the microwave at 150° C. for 20 minutes. EtOAc (10 mL) was added to the mixture and a precipitate formed which was filtered off—this was shown to be remaining piperidinylbenzamide starting material. The filtrate was diluted with further EtOAc (10 mL) and washed with water (3×15 mL). On the third washing a precipitate formed—this was filtered off and found to be mainly desired product. The filtrate was dried (phase separator) and concentrated to give further solid. Both solids were purified by MDAP and the clean fractions combined and concentrated in vacuo before drying in a drying pistol to give E17 (117 mg); $^1$H NMR (d6-DMSO) δ 11.54 (1H, brs), 8.48 (1H, d), 8.21 (1H, s), 7.86 (2H, d), 7.52 (1H, t), 7.45 (2H, t), 7.08 (1H, s), 4.13-3.98 (3H, m), 3.04 (2H, t), 2.33 (3H, s), 1.93 (2H, dd), 1.72 (2H, ddd), MS(ES+) 336 [M+H]$^+$.

Example 18 (E18)

N-[1-(5-Ethyl-1H-pyrrolo[2,3-d]pyrimidin-4-yl)-4-piperidinyl]benzamide

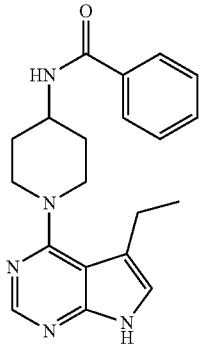

A mixture of N-{1-[5-ethyl-7-(phenylsulfonyl)-7H-pyrrolo[2,3-d]pyrimidin-4-yl]-4-piperidinyl}benzamide D7 (174 mg) and cesium carbonate (347 mg, 1.066 mmol) in MeOH (1.5 mL) and THF (3 mL) was stirred at room temperature for 3 hours. LCMS showed loss of starting material so the mixture was partitioned between EtOAc (10 mL) and water (10 mL). The organic phase was isolated (phase separator) and then concentrated. The crude material was purified by MDAP to give E18 (6 mg), $^1$H NMR (d6-DMSO) δ 11.59 (1H, brs), 8.38 (1H, d), 8.24 (1H, s), 8.78 (2H, d), 7.52 (1H, t), 7.46 (2H, t), 7.09 (1H, s), 4.06 (1H, m), 3.95 (2H, d), 3.02 (2H, t), 2.77 (2H, q), 1.94 (2H, d), 1.76 (2H, ddd), 1.26 (3H, t), MS(ES+) 350 [M+H]$^+$.

Example 19 (E19)

N-{1-[5-(1-Methylethenyl)-1H-pyrrolo[2,3-d]pyrimidin-4-yl]-4-piperidinyl}benzamide

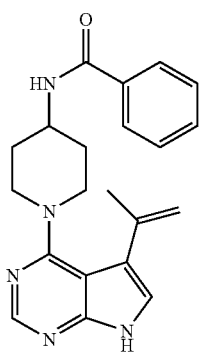 [SMILES: C=C(C)c1c[nH]c2ncnc(N3CCC(NC(=O)c4ccccc4)CC3)c12]

A mixture of N-{1-[5-(1-methylethenyl)-7-(phenylsulfonyl)-7H-pyrrolo[2,3-d]pyrimidin-4-yl]-4-piperidinyl}benzamide D8 (100 mg) and cesium carbonate (195 mg, 0.598 mmol) in THF (1.4 mL) and MeOH (0.7 mL) was stirred at room temperature for 4 hours. LCMS showed complete loss of starting material, but a few products were present. The mixture was partitioned between EtOAc (15 mL) and water (15 mL) and then the organic layer was washed with water (15 mL) and brine (15 mL) before it was dried (MgSO$_4$), filtered and the solvent removed in vacuo. The crude product was purified by MDAP and the one clean fraction was concentrated in vacuo to give E19 (12 mg) as a white solid, $^1$H NMR (d6-DMSO) δ 11.88 (1H, s), 8.32 (1H, d), 8.27 (1H, s), 7.85 (2H, d), 7.51 (1H, t), 7.44 (2H, t), 7.31 (1H, s), 5.10 (2H, s), 4.10 (2H, d), 4.02 (1H, m), 2.97 (2H, t), 2.13 (3H, s), 1.83 (2H, d), 1.67 (2H, ddd), MS(ES+) 362 [M+H]$^+$.

Example 20 (E20)

N-{1-[5-(1-Methylethyl)-1H-pyrrolo[2,3-d]pyrimidin-4-yl]-4-piperidinyl}benzamide

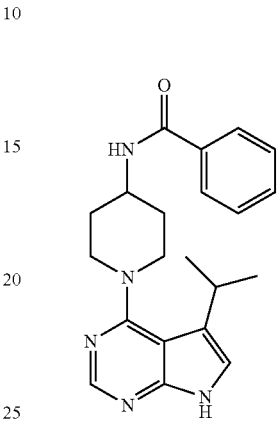

To a solution of N-{1-[5-(1-methylethyl)-7-(phenylsulfonyl)-7H-pyrrolo[2,3-d]pyrimidin-4-yl]-4-piperidinyl}benzamide D9 (140 mg) in THF (2 mL) and MeOH (1 mL) was added cesium carbonate (272 mg, 0.834 mmol) and the mixture stirred for 2 hours. LCMS showed a small amount of starting material so the reaction was stirred for a further 2 hours. The mixture was then partitioned between EtOAc (20 mL) and water (20 mL) and the organic phase washed with water (20 mL) and brine (20 mL) before it was dried (MgSO$_4$), filtered and the solvent removed in vacuo. The crude product was purified by MDAP. The compound-containing fractions were concentrated and dried in a vacuum oven to give E20 (23 mg) as a white solid, $^1$H NMR (d6-DMSO) δ 11.62 (1H, s), 8.39 (1H, d), 8.26 (1H, s), 7.88 (2H, d), 7.52 (1H, t), 7.46 (2H, t), 7.09 (1H, s), 4.05 (1H, m), 3.90 (2H, d), 3.16 (1H, septet), 3.00 (2H, t), 1.94 (2H, d), 1.77 (2H, ddd), 1.28 (6H, d), MS(ES+) 364 [M+H]$^+$.

Example 21 (E21)

N-[1-(5-Methyl-1H-pyrrolo[2,3-d]pyrimidin-4-yl)-4-piperidinyl]-2-pyridinecarboxamide

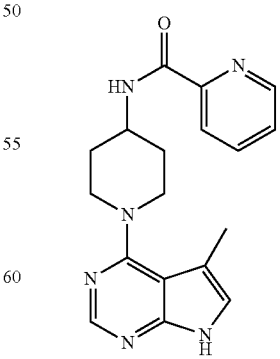

To a mixture of 2-pyridine carboxylic acid (41.4 mg, 0.336 mmol), EDC (68.7 mg, 0.359 mmol), HOBt (54.9 mg, 0.359 mmol) and DIPEA (0.098 mL, 0.560 mmol) in DCM (1 mL), prestirred for 10 minutes, was added 1-(5-methyl-7H-pyrrolo[2,3-d]pyrimidin-4-yl)-4-piperidinamine hydrochloride D11 (60 mg) and the mixture stirred for 18 hours. The mixture was partitioned between DCM (4 mL) and aqueous sodium bicarbonate (4 mL) and the aqueous phase extracted with further DCM (4 mL). The combined organic fractions were concentrated in vacuo and purified by MDAP. The solvent was then removed in vacuo from the product-containing fractions, to afford E21 (34 mg), $^1$H NMR (d6-DMSO) δ 11.52 (1H, s), 8.69 (1H, d), 8.65 (1H, d), 8.21 (1H, s), 8.06 (1H, d), 8.00 (1H, t), 7.61 (1H, t), 7.06 (1H, s), 4.08 (1H, m), 4.00 (2H, d), 3.05 (2H, t), 2.37 (3H, s), 2.0-1.7 (4H, m), MS(ES+) 337 [M+H]$^+$.

Example 22 (E22)

6-Methyl-N-[1-(5-methyl-1H-pyrrolo[2,3-d]pyrimidin-4-yl)-4-piperidinyl]-3-pyridinecarboxamide

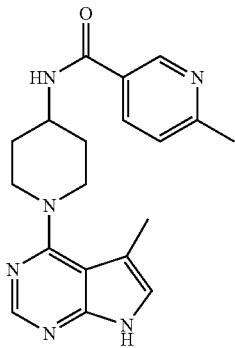 [SMILES: Cc1ccc(C(=O)NC2CCN(c3ncnc4[nH]cc(C)c34)CC2)cn1]

To a mixture of 6-methyl-3-pyridinecarboxylic acid (46.1 mg, 0.336 mmol), EDC (68.7 mg, 0.359 mmol), HOBt (54.9 mg, 0.359 mmol) and DIPEA (0.098 mL, 0.560 mmol) in DCM (1 mL), prestirred for 10 minutes, was added 1-(5-methyl-7H-pyrrolo[2,3-d]pyrimidin-4-yl)-4-piperidinamine hydrochloride D11 (60 mg) and the mixture stirred for 18 hours. The mixture was partitioned between DCM (4 mL) and aqueous sodium bicarbonate (4 mL) and the aqueous phase was extracted with further DCM (4 mL). The combined organic fractions were concentrated in vacuo and purified by MDAP. The solvent was then removed in vacuo from the product containing fractions, to afford E22 (14 mg), $^1$H NMR (d6-DMSO) δ 11.53 (1H, s), 8.90 (1H, s), 8.47 (1H, d), 8.22 (1H, s), 8.10 (1H, d), 7.35 (1H, d), 7.07 (1H, s), 4.08 (1H, m), 4.02 (2H, d), 3.95 (2H, t), 2.47 (3H, s), 2.37 (3H, s), 1.95 (2H, d), 1.73 (2H, ddd), MS(ES+) 351 [M+H]$^+$.

Example 23 (E23)

2-(Methyloxy)-N-[1-(5-methyl-1H-pyrrolo[2,3-d]pyrimidin-4-yl)-4-piperidinyl]-4-pyridinecarboxamide

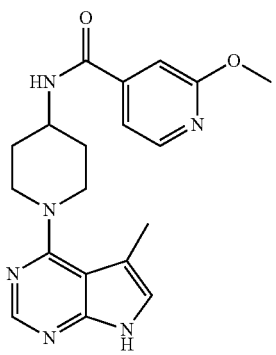 [SMILES: COc1cc(C(=O)NC2CCN(c3ncnc4[nH]cc(C)c34)CC2)ccn1]

A mixture of 2-(methyloxy)-4-pyridinecarboxylic acid (40 mg, 0.261 mmol), EDC (80 mg, 0.418 mmol), HOBt (64.1 mg, 0.418 mmol) and DIPEA (0.114 mL, 0.654 mmol) in DCM (1 mL) was prestirred for 10 minutes before adding 1-(5-methyl-7H-pyrrolo[2,3-d]pyrimidin-4-yl)-4-piperidinamine hydrochloride D11 (70 mg) and the mixture was stirred at room temperature for 18 hours. The reaction mixture was then partitioned between DCM (4 mL) and 2M NaOH (4 mL) and the organic phase dried (phase separator) before it was concentrated in vacuo. The crude material was then purified by MDAP. After concentrating the product-containing fractions in vacuo the mixture was triturated with Et$_2$O and filtered to give the title compound E23 as white solid (16 mg), $^1$H NMR (d6-DMSO) δ 11.54 (1H, s), 8.59 (1H, d), 8.28 (1H, d), 8.22 (1H, s), 7.36 (1H, d), 7.21 (1H, s), 7.07 (1H, s), 4.14-3.99 (3H, m), 3.89 (3H, s), 3.05 (2H, t), 2.36 (3H, s), 1.94 (2H, d), 1.73 (2H, ddd), MS(ES+) 367 [M+H]$^+$.

Example 24 (E24)

3-(Methyloxy)-N-[1-(5-methyl-1H-pyrrolo[2,3-d]pyrimidin-4-yl)-4-piperidinyl]benzamide

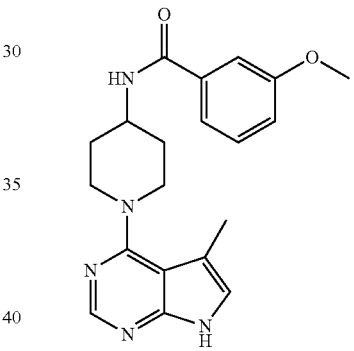

To a mixture of 1-(5-methyl-7H-pyrrolo[2,3-d]pyrimidin-4-yl)-4-piperidinamine hydrochloride D11 (70 mg) and DIPEA (0.159 mL, 0.908 mmol) in DCM (1 mL) was added 3-(methyloxy)benzoyl chloride (56.8 mg, 0.333 mmol) and the reaction stirred for 18 hours. The mixture was partitioned between DCM (4 mL) and aqueous sodium bicarbonate (4 mL). The organic phase was then washed with 2M HCl (4 mL) before it was dried (phase separator) and concentrated. The crude product was purified by MDAP but the product was not clean, so it was then purified by silica chromatography eluting 2-10% MeOH in DCM to give E24 (17 mg) as a white solid, $^1$H NMR (d6-DMSO) δ 11.53 (1H, s), 8.33 (1H, d), 8.22 (1H, s), 7.45 (1H, d), 7.41 (1H, s), 7.37 (1H, t), 7.08 (1H, d), 7.07 (1H, s), 4.12-3.99 (3H, m), 3.81 (3H, s), 3.04 (2H, t), 2.37 (3H, s), 1.94 (2H, d), 1.74 (2H, ddd), MS(ES+) 366 [M+H]$^+$.

Example 25 (E25)

2-Methyl-N-[1-(5-methyl-7H-pyrrolo[2,3-d]pyrimidin-4-yl)-4-piperidinyl]-4-pyridinecarboxamide

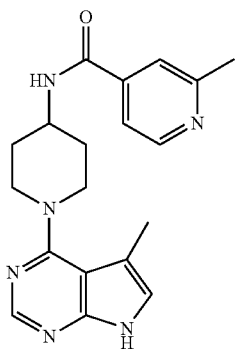

To a mixture of 2-methyl-4-pyridinecarboxylic acid (41 mg, 0.299 mmol), EDC (86 mg, 0.448 mmol), HOBt (68.6 mg, 0.448 mmol) and DIPEA (0.130 mL, 0.747 mmol) in DCM (1 mL), prestirred for 10 minutes, was added 1-(5-methyl-7H-pyrrolo[2,3-d]pyrimidin-4-yl)-4-piperidinamine hydrochloride D11 (80 mg) and the mixture stirred at room temperature for 18 hours. The solvent was removed in vacuo and the mixture purified by MDAP to give the title compound E25 (37 mg), $^1$H NMR (d6-DMSO) δ 11.52 (1H, s), 8.59 (1H, d), 8.57 (1H, d), 8.22 (1H, s), 7.65 (1H, d), 7.56 (1H, d), 7.07 (1H, s), 4.11-3.99 (3H, m), 3.06 (2H, t), 2.53 (3H, s), 2.37 (3H, s), 1.94 (2H, d), 1.73 (2H, ddd), MS(ES+) 351 [M+H]$^+$.

Example 26 (E26)

2-Methyl-N-[1-(5-methyl-7H-pyrrolo[2,3-d]pyrimidin-4-yl)-4-piperidinyl]benzamide

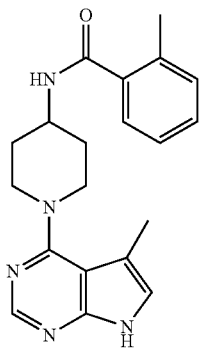

To a mixture of 1-(5-methyl-7H-pyrrolo[2,3-d]pyrimidin-4-yl)-4-piperidinamine hydrochloride D11 (70 mg) and DIPEA (0.11 mL, 0.605 mmol) in DCM (1 mL) was added 2-methylbenzoyl chloride (70.2 mg, 0.454 mmol) and the reaction stirred at room temperature for 18 hours. The solvent was removed in vacuo and the mixture purified by MDAP to give the title compound E26 (25 mg) as a pale pink solid, $^1$H NMR (d6-DMSO) 11.55 (1H, brs), 8.26 (1H, d), 8.21 (1H, s), 7.30 (2H, m), 7.25 (2H, m), 7.06 (1H, s), 4.0 (3H, m), 3.06 (2H, t), 2.35 (3H, s), 2.35 (3H, s), 1.94 (2H, m), 1.67 (2H, m), MS(ES+) 350 [M+H]$^+$.

Example 27 (E27)

N-[1-(5-methyl-7H-pyrrolo[2,3-d]pyrimidin-4-yl)-4-piperidinyl]-4-pyridinecarboxamide

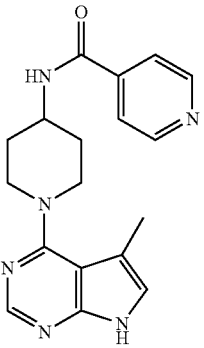 [SMILES: Cc1c[nH]c2ncnc(N3CCC(NC(=O)c4ccncc4)CC3)c12]

To a solution of 4-pyridinecarboxylic acid (59.8 mg, 0.486 mmol), EDC.HCl (115 mg, 0.598 mmol), HOBt (92 mg, 0.598 mmol) and N,N-diisopropylethylamine (0.163 mL, 0.934 mmol) in N,N-dimethylformamide (1 mL), stirred for 10 minutes, was added 1-(5-methyl-7H-pyrrolo[2,3-d]pyrimidin-4-yl)-4-piperidinamine hydrochloride (100 mg), D11, and the reaction stirred for 18 h. The solvent was removed in vacuo and the mixture purified by high pH MDAP to give the title compound E27 (45 mg). $^1$H NMR (d6-DMSO) δ 11.53 (1H, s), 8.72 (2H, d), 8.66 (1H, d), 8.22 (1H, s), 7.78 (2H, d), 7.07 (1H, s), 4.09 (1H, m), 4.02 (2H, d), 3.06 (2H, t), 2.37 (3H, s), 1.95 (2H, d), 1.74 (2H, ddd), MS(ES+) 337 [M+H]$^+$.

Example 28 (E28)

3,5-dimethyl-N-[1-(5-methyl-7,1-pyrrolo[2,3-d]pyrimidin-4-yl)-4-piperidinyl]-4-isoxazolecarboxamide

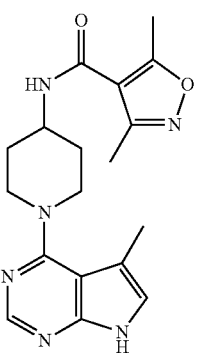 [SMILES: Cc1noc(C)c1C(=O)NC1CCN(c2ncnc3[nH]cc(C)c23)CC1]

To a mixture of 3,5-dimethyl-4-isoxazolecarboxylic acid (68.5 mg, 0.486 mmol), EDC.HCl (115 mg, 0.598 mmol), HOBt (92 mg, 0.598 mmol) and N,N-diisopropylethylamine (0.163 mL, 0.934 mmol) in N,N-dimethylformamide (1 mL), stirred for 10 minutes, was added 1-(5-methyl-7H-pyrrolo[2,3-d]pyrimidin-4-yl)-4-piperidinamine hydrochloride (100 mg), D11, and the reaction stirred for 18 h. The solvent was removed in vacuo and the mixture purified by high pH MDAP to give the title compound E28 (60 mg). $^1$H NMR (d6-DMSO) δ 11.53 (1H, s), 8.21 (1H, s), 8.00 (1H, d), 7.07 (1H, s), 4.02-3.94 (3H, m), 3.07 (2H, t), 2.48 (3H, s), 2.36 (3H, s), 2.28 (3H, s), 1.96 (2H, d), 1.68 (2H, ddd), MS(ES+) 355 [M+H]$^+$.

Example 29 (E29)

N-[1-(5-bromo-7H-pyrrolo[2,3-d]pyrimidin-4-yl)-4-piperidinyl]benzamide

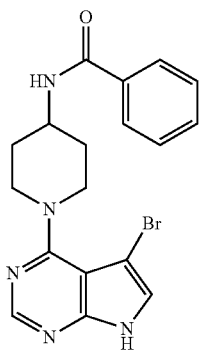 [SMILES: O=C(NC1CCN(c2ncnc3[nH]cc(Br)c23)CC1)c1ccccc1]

To a mixture of N-{1-[5-bromo-7-(phenylsulfonyl)-7H-pyrrolo[2,3-d]pyrimidin-4-yl]-4-piperidinyl}benzamide (100 mg), D6, in methanol (1 mL) and tetrahydrofuran (2 mL) was added cesium carbonate (181 mg, 0.555 mmol) and the mixture stirred at room temperature for 3 h. The reaction mixture was partitioned between water (10 mL) and ethyl acetate (15 mL) and the organic phase dried (phase separator) and the solvent removed in vacuo. The crude material was purified by MDAP to give the title compound E29 (32 mg) as a white solid. $^1$H NMR (d6-DMSO) δ 12.24 (1H, s), 8.38 (1H, d), 8.29 (1H, s), 7.87 (2H, d), 7.55 (1H, s), 7.53 (1H, t), 7.46 (2H, t), 4.18 (2H, d), 4.08 (1H, m), 3.09 (2H, t), 1.94 (2H, d), 1.81 (2H, ddd), MS(ES+) 400 [M($C_{18}H_{18}{}^{79}BrN_5O$)+H]$^+$.

Example 30 (E30)

N-methyl-N-[1-(7H-pyrrolo[2,3-d]pyrimidin-4-yl)-4-piperidinyl]benzamide

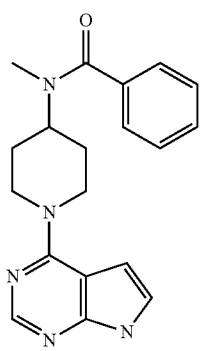

DIPEA (642 µl, 3.67 mmol) was added to a mixture of N-methyl-1-(7H-pyrrolo[2,3-d]pyrimidin-4-yl)-4-piperidinamine D13 (177 mg), benzoic acid (93 mg, 0.765 mmol), HATU (349 mg, 0.918 mmol), aza-HOBt (62.5 mg, 0.459 mmol) in N,N-Dimethylformamide (DMF) (2551 µl). The mixture was stirred at room temperature during 2 h. Then the solvents were evaporated. The crude was finally purified via MDAP using a high pH method. Because of the NMR the solid was purified again using the High pH MDAP method. Fractions of each MDAP were combined and evaporated together to give a white solid of E30 in 51 mg. LCMS [M+H]+ 336.19@0.62 min (2 min run)

Example 31 (E31)

2,6-dimethyl-N-[1-(5-methyl-7,1-pyrrolo[2,3-d]pyrimidin-4-yl)-4-piperidinyl]benzamide hydrochloride

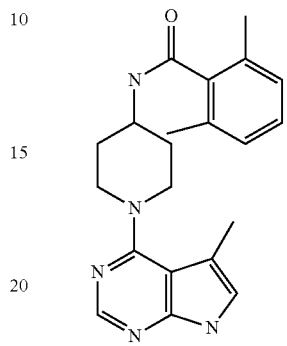

To a mixture of 1-(5-methyl-7H-pyrrolo[2,3-d]pyrimidin-4-yl)-4-piperidinamine (D11a) (60 mg) and 2,6-dimethylbenzoyl chloride (40.5 mg, 0.240 mmol, commercially available from e.g. fluorochem or butt park) in Dichloromethane (DCM) (1 mL) at 0° C. was added N,N-diisopropylethylamine (0.063 mL, 0.361 mmol) and the mixture stirred at room temperature for 6 h. LCMS showed incomplete reaction plus by-products. Further 2,6-dimethylbenzoyl chloride (40.5 mg, 0.240 mmol) and N,N-diisopropylethylamine (0.063 mL, 0.361 mmol) were added and the reaction stirred for 1 h and allowed to stand for 60 h (over weekend. The solvent was removed in vacuo and the crude product purified by MDAP to give 20 mg of product. This was very insoluble and was dissolved in 2M HCl followed by evaporation of the solvent to form the hydrochloride salt of E31 as a bright pink solid in 15 mg. LCMS [M+H]+364.16@ 0.71 min (2 min run)

Example 32 (E32)

N-methyl-N-[1-(5-methyl-7H-pyrrolo[2,3-d]pyrimidin-4-yl)-4-piperidinyl]benzamide

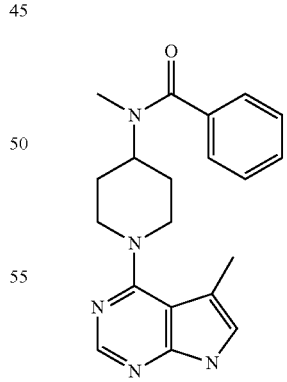

To 4-chloro-5-methyl-7H-pyrrolo[2,3-d]pyrimidine D4 (0.154 g) and N-methyl-N-4-piperidinylbenzamide D15 (0.2 g) was added Ethanol (5 mL) and the reaction was heated at 150° C. for 30 minutes in the microwave. The reaction was heated again at 150° C. for 20 minutes. During the cooling, a white precipitate formed. This precipitate was filtered off and washed with Ethanol before being dried in vacuo at 40° C. to afford product in 49 mg. The filtrate was removed in vacuo and the crude residue purified by MDAP using the formic acid method. Fractions corresponding to the desired product were combined and solvent removed to give the product E32 in 22 mg. LCMS [M+H]+350.12@0.66 min (2 min run)

Example 33 (E33)

1-methyl-N-[1-(5-methyl-7H-pyrrolo[2,3-d]pyrimidin-4-yl)-4-piperidinyl]-1H-imidazole-5-carboxamide

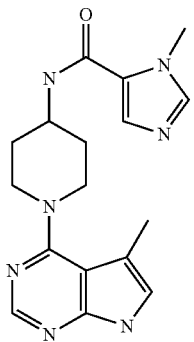 [SMILES: Cc1c[nH]c2ncnc(N3CCC(NC(=O)c4cncn4C)CC3)c12]

To a mixture of 1-methyl-1H-imidazole-5-carboxylic acid (61.2 mg, 0.486 mmol, commercially available from e.g. Maybridge, Apollo or Butt Park), EDC (107 mg, 0.560 mmol), HOBt (86 mg, 0.560 mmol) and N,N-diisopropylethylamine (0.163 nit, 0.934 mmol) in Dichloromethane (DCM) (2 mL), prestirred for 10 minutes, was added 1-(5-methyl-7H-pyrrolo[2,3-d]pyrimidin-4-yl)-4-piperidinamine hydrochloride
D11 (100 mg) and the mixture stirred for 18 h. The reaction mixture was partitioned between DCM and aqueous sodium bicarbonate. The aqueous layer was extracted with further DCM and then the combined organic fractions were dried (phase separator) and the solvent removed in vacuo. The crude product was purified by high pH MDAP to give the product E33 in 33 mg as a white solid. LCMS [M+H]+ 340.23@1.66 min (5 min run)

Examples 34-35

N-[3-(methyloxy)-1-(5-methyl-7H-pyrrolo[2,3-d]pyrimidin-4-yl)-4-piperidinyl]benzamide (E34 and E35)

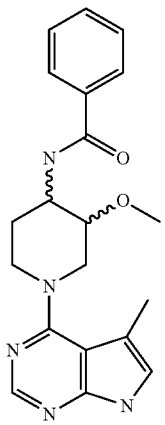 [SMILES: COC1CN(c2ncnc3[nH]cc(C)c23)CCC1NC(=O)c1ccccc1]

To a suspension of N-[3-(methyloxy)-4-piperidinyl]benzamide D21 (440 mg), 4-chloro-5-methyl-7H-pyrrolo[2,3-d]pyrimidine(D4) (315 mg, 1.88 mmol) and cesium carbonate (306 mg, 0.94 mmol) in EtOH (5 ml) was microwaved at 130° C. for 2 hours. The resulting mixture was poured into water (50 ml), extracted with DCM (3×50 ml). The organic layer was dried over anhydrous MgSO$_4$, concentrated in vacuo. The crude product was purified on silica gel eluting with DCM/MeOH 50/1, DCM/MeOH 15/1 to obtain 1 clean isomer E34 in 150 mg as a white solid. LCMS [MH+] 366@1.54 min (5 min run)

The other isomer needed a further purification by prep-HPLC (column: shimadzu 20 mmx 250 mm×2; mobile phase A 10 mmol/L NH$_4$HCO$_3$ solution B MeCN; flow rate 30 mL/min 0=7.5 min 40% MeCN, 7.5~7.8 min 40-~95%, 7.8~12.8 min 95% MeCN) to obtain other isomer E35 in 85 mg as a white solid. LCMS [MH+] 366@1.51 min (5 min run)

Chiral Separation of E35 to Give E36 and E37.

Analytical Conditions:

Chiralpak AD (4.6 mm×250 mm, 10 μm)

Heptane:Ethanol (50:50) v/v pump-mixed; flow rate=1.0 mL/min

U.V. Absorbance@254 nm

Autosampler injection (10 μl or 25 ul on column)

Isocratic Run-time=20 minutes

Preparative Conditions

Chiralpak AD (4.6 mm×250 mm, 10 μm)

Heptane:Ethanol (50:50) v/v pump-mixed; flow rate=17.0 mL/min

U.V. Absorbance @215 nm

Autosampler injection (900 μl on column)

Isocratic Run-time=20 minutes

Method:

50 mg were submitted for prep of which approximately 1 mg was removed and dissolved in 1 ml of EtOH for method development.

Method developed as described in analytical conditions section:

Faster eluting enantiomer=6.2 minutes

Slower eluting enantiomer=10.8 minutes 49 mg were dissolved in 4 ml of ethanol.

900 ul injected onto column×4 and sample purified using the preparative method described hereinabove.

The faster eluting enantiomer (Vial 11 in representative chromatogram) were collected and combined. A small aliquot (1 ml) was removed for QC analysis. The sample was dried using a rotary evaporator. 23 mg recovered of faster eluting enantiomer, E36.

e.e=>99.9% (no evidence of the other enantiomer)

The slower eluting enantiomer (Vial 12 in representative chromatogram) were collected and combined. A small aliquot (1 ml) was removed for QC analysis. The sample was dried using a rotary evaporator. 23 mg recovered of slower eluting enantiomer, E37.

e.e. =98.5%

Example 38 (E38)

N-methyl-N-[1-(5-methyl-7H-pyrrolo[2,3-s]pyrimidin-4-yl)-4-piperidinyl]-4-pyridinecarboxamide

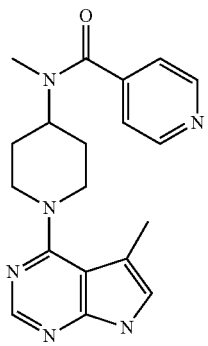 [SMILES: Cc1c[nH]c2ncnc(N3CCC(N(C)C(=O)c4ccncc4)CC3)c12]

4-pyridinecarboxylic acid (52.4 mg, 0.426 mmol) was dissolve in N,N-Dimethylformamide (DMF) (5 mL) under argon flow. HATU (148 mg, 0.390 mmol) was added. After 30 minutes of stirring, N-methyl-1-(5-methyl-7H-pyrrolo[2,3-d]pyrimidin-4-yl)-4-piperidinamine hydrochloride D23 (100 mg) was added. After 20 minutes of stirring, diisopropylethylamine (45.9 mg, 0.355 mmol) was added. The mixture was stirred at room temperature under argon flow for 2 h00. DCM 10 mL has been added to the mixture. A work-up has been done with 2×10 mL of $Na_2CO_3$, 10 mL of brine. The organic layer was filtrated with a phase separator. The solvent was removed in vacuo. The crude material was purified by high pH MDAP. The fractions have been collected and evaporated to give the product E38 in 14 mg. The product was dried overnight in the vacuum drier. LCMS [M+H]+351.14@1.74 min (5 min run) Some material left in a vial after MDAP—this was purified by further MDAP to give a further 14 mg of desired material E38. LCMS [M+H]+351.08@1.75 min (5 min run)

Example 39 (E39)

N-[1-(5-bromo-7H-pyrrolo[2,3-d]pyrimidin-4-yl)-4-piperidinyl]-N-methyl-4-pyridinecarboxamide

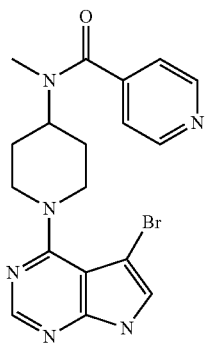 [SMILES: CN(C(=O)c1ccncc1)C1CCN(c2ncnc3[nH]cc(Br)c23)CC1]

N-{1-[5-bromo-7-(phenylsulfonyl)-7H-pyrrolo[2,3-d]pyrimidin-4-yl]-4-piperidinyl}-N-methyl-4-pyridinecarboxamide D26 (41 mg) was dissolved with Tetrahydrofuran (THF) (1 mL) and Methanol (0.500 mL). Cesium carbonate (72.2 mg, 0.221 mmol) was added. The mixture was stirred at room temperature for 30 min. The mixture was partitioned between ethyl acetate (15 mL) and water (5 mL). The aqueous layer was extracted with ethyl acetate (15 mL). The combined organic phase was filtered by a phase separator and the solvent was removed in vacuo. The crude material was purified by MDAP. Evaporated the solvent and put in the vacuum oven to give the product E39 in 0.0168 g as a white powder. LCMS [M+H]+414.94/416.94@1.86 min (5 min run)

Example 40 (E40)

N-{1-[5-(1-methyl-1H-pyrazol-4-yl)-1H-pyrrolo[2,3-d]pyrimidin-4-yl]-4-piperidinyl}benzamide

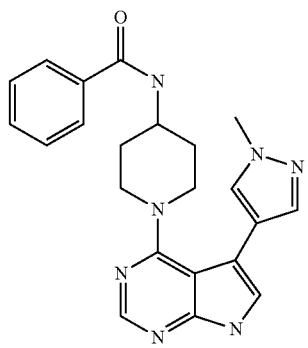 [SMILES: Cn1cc(-c2c[nH]c3ncnc(N4CCC(NC(=O)c5ccccc5)CC4)c23)cn1]

N-{1-[5-(1-methyl-1H-pyrazol-4-yl)-7-(phenylsulfonyl)-7H-pyrrolo[2,3-d]pyrimidin-4-yl]-4-piperidinyl}benzamide D27 (160 mg) and cesium carbonate (285 mg, 0.88 mmol) in MeOH (2 ml) and THF (4 ml) was stirred under nitrogen at room temperature for 1 hour. EtOAc was added followed by water and the aqueous layer was extracted with EtOAc. The combined extracts were washed with brine, dried over $MgSO_4$ and concentrated to give crude product. This was purified by TLC preparation eluting with EtOAc to give 50 mg of desired product E40. LCMS [MH+] 402.2@1.44 min (5 min run)

Example 41 (E41)

N-{1-[5-(3-furanyl)-1H-pyrrolo[2,3-d]pyrimidin-4-yl]-4-piperidinyl}benzamide

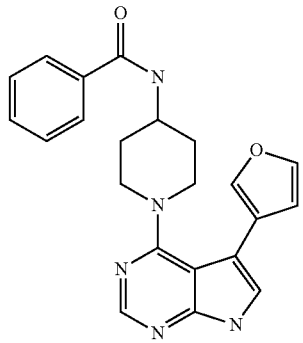 [SMILES: O=C(NC1CCN(c2ncnc3[nH]cc(-c4ccoc4)c23)CC1)c1ccccc1]

N-{1-[5-(3-furanyl)-7-(phenylsulfonyl)-7H-pyrrolo[2,3-d]pyrimidin-4-yl]-4-piperidinyl}benzamide D28 (60 mg) and cesium carbonate (110 mg, 0.34 mmol) in MeOH (1.5 ml) and THF (3 ml) were stirred under nitrogen for 1 hour. Reaction filtered, concentrated to give crude product. Purified by TLC preparation to give 30 mg of impure product. Repurified by prep HPLC (Venusti XBP C18 10 uM, 100 A m 30×250 mm, A: 0.1% TFA/Water, B: MeCN 0-6.8 mins 25-75% MeCN, 6.8-7.0 min 75-95% MeCN, 7.0-10 min 95-95% MeCN, flow rate 40 ml/min) to give 10 mg of desired product E41. LCMS [MH+] 388.2@1.12 min (5 min run)

Example 42 (E42)

N-[3-[(methyloxy)methyl]-1-(5-methyl-7H-pyrrolo[2,3-d]pyrimidin-4-yl)-4-piperidinyl]benzamide

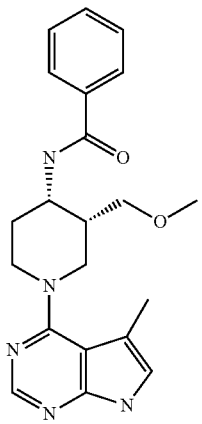 [SMILES: COC[C@@H]1CN(c2ncnc3[nH]cc(C)c23)CC[C@@H]1NC(=O)c1ccccc1]

4-chloro-5-methyl-7H-pyrrolo[2,3-d]pyrimidine D4 (218 mg), N-{3-[(methyloxy)methyl]-4-piperidinyl}benzamide D35 (500 mg) and N,N-diisopropylethylamine (504 mg, 3.9 mmol) were dissolved in NMP (10 ml). The tube was sealed and the reaction carried out in the microwave. The reaction was heated at 150° C. for 3 hours. The reaction mixture was poured into ethyl acetate (120 ml), washed with water (3×30 ml), brine (2×30 ml). Organic layer collected and dried with MgSO$_4$, filtered and solvent removed. Purification of the crude product by chromatography on silica gel eluting with DCM/MeOH 30/1 to give product. Repurified by prep-HPLC (column: x-bridge C18sun, 30×, 50 mm; mobile phase: A 10 mmol/L NH$_3$.H$_2$O B ACN; gradient: 35-40% ACN in 6-7 min. Rt 6.3 min to give the product E42 as a yellow solid in 86 mg. LCMS [M+H] 380.2@1.57 min (mixture of 2 isomers) (5 min run)

Example 43 (E43)

N-[1-(5-methyl-7H-pyrrolo[2,3-d]pyrimidin-4-yl)-4-piperidinyl]-3-{[2-(1-pyrrolidinyl)ethyl]oxy}benzamide

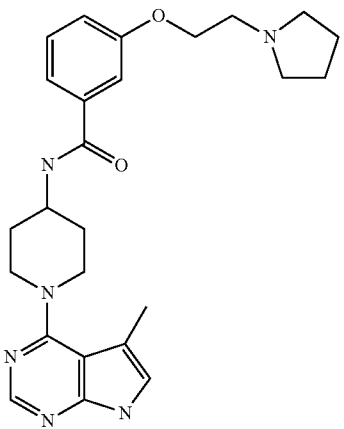 [SMILES: Cc1c[nH]c2ncnc(N3CCC(NC(=O)c4cccc(OCCN5CCCC5)c4)CC3)c12]

3-{[2-(1-pyrrolidinyl)ethyl]oxy}benzoic acid D38 (200 mg) and 2-chloro-4,6-dimethoxy-1,3,5-triazine (171 mg, 0.98 mmol) was dissolved under argon in MeCN (20 ml) and cooled down to 0° C. Then N-methylmorpholine (0.3 ml) was added and the mixture was stirred at 0° C. for 2 hours. To this mixture was added 1-(5-methyl-7H-pyrrolo[2,3-d]pyrimidin-4-yl)-4-piperidinamine hydrochloride D11 (240 mg) in small portions, afterwards the reaction was then warmed up to room temperature. After stirring for 16 hours, the reaction was filtered and concentrated to give crude product. This product was purified by prep-HPLC (A 0.01% NH$_4$HCO$_3$/Water, B: ACN, 0~8 min 25-50%, 50%~60% 8-12 min, 60%~95% 12-15 min, 95~95% 15-18 min) to give 50 mg of white solid of desired product E43. LCMS [MH+] 449.2@1.52 min (5 min run)

Example 44 (E44)

N-[1-(5-chloro-1H-pyrrolo[2,3-d]pyrimidin-4-yl)-4-piperidinyl]benzamide

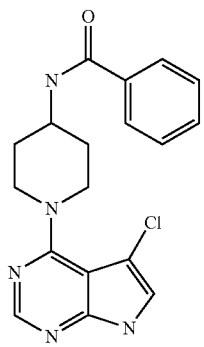 [SMILES: O=C(NC1CCN(c2ncnc3[nH]cc(Cl)c23)CC1)c1ccccc1]

N-{1-[5-chloro-7-(phenylsulfonyl)-7H-pyrrolo[2,3-d]pyrimidin-4-yl]-4-piperidinyl}benzamide D41 (240 mg) and sodium methoxide (157 mg, 2.9 mmol) were dissolved in MeOH (15 ml). The reaction mixture was heated at 75° C. for 30 min and then extracted with EtOAc (150 ml); washed with water (60 ml), brine (2×60 ml). Yellow oil obtained, solvent removed to afford a yellow solid which was purified by prep HPLC (mobile phase: A: 0.01% NH$_4$HCO$_3$/H$_2$O B; ACN. Column shimazu PRC-ODS 10.0 uM, 20×250 mm. Method 07.8 min 40-50% ACN 8-10 min 95~95% ACN. Flow rate 30 mL/min to give product E44 as an ashen solid in 73 mg. LCMS [MH+] 356.0@1.58 min (5 min run)

Example 45 (E45)

N-[1-(5-cyano-1H-pyrrolo[2,3-d]pyrimidin-4-yl)-4-piperidinyl]benzamide

N-{1-[5-cyano-7-({[2-(trimethylsilyl)ethyl]oxy}methyl)-7H-pyrrolo[2,3-d]pyrimidin-4-yl]-4-piperidinyl}benzamide D44 (69 mg) and LiBF$_4$ (85 mg, 0.9 mmol) were dissolved in MeCN (10 ml) and then the reaction mixture was heated at 80° C. for 16 hours.

Crude product purified by flash chromatography on silica gel eluting with pet eth/EtOAc 3/1~1/1 to give the desired product E45 as a yellow solid in 48 mg. LCMS [MH+] 347.0@1.49 min (5 min run)

Example 46 (E46)

N-[1-(5-methyl-1H-pyrrolo[2,3-d]pyrimidin-4-yl)-4-piperidinyl]-3-{[2-(4-morpholinyl)ethyl]oxy}benzamide hydrochloride To a solution of 1-(5-methyl-1H-pyrrolo[2,3-d]pyrimidin-4-yl)-4-piperidinamine D11a (99 mg), 3-{[2-(4-morpholinyethyl]oxy}benzoic acid D51 (90 mg, 0.358 mmol) and DIPEA (0.188 mL, 1.075 mmol) in the mixture solvent of NMP (5 mL) and DCM (5 mL) stirred at 20° C. was added EDC (200 mg, 1.043 mmol) and HOBT (200 mg, 1.306 mmol). The reaction mixture was stirred at 20° C. overnight. Then the reaction mixture was washed with water (50 ml) and extracted with DCM (50 ml×3). The combined organic layer was dried with Na$_2$SO$_4$ and concentrated. The residue was purified via Gilson GX-281.

Instrument: Gilson 281
Mobile Phase: A=0.01% NH$_4$HCO$_3$/H$_2$O, B=MeCN
Flow Rate: 30.0 ml/minute
Column: Shimadzu PRC-ODS 15 μm 19 mm×250 mm
Method:

$$B: A = \begin{matrix} 35\%: 65\% \text{ to } 45\%: 55\% & 0 \text{ to } 7 \text{ minutes} \\ 95\%: 5\% & 7 \text{ to } 14 \text{ minutes} \end{matrix}$$

Target peak: at 8.0 minutes

The target peak was collected and concentrated and acidified to be HCl salt of the target compound E46 in 145 mg as a white solid. LCMS Retention time=1.48 minutes, [M C$_6$H$_{12}$NO]$^+$350 (5 minutes run)

Example 47 (E47)

3-({2-[(3R)-3-fluoro-1-pyrrolidinyl]ethyl}oxy)-N-[1-(5-methyl-1H-pyrrolo[2,3d]pyrimidin-4-yl)-4-piperidinyl]benzamide hydrochloride To a solution of 1-(5-methyl-1H-pyrrolo[2,3-d]pyrimidin-4-yl)-4-piperidinamine D11a (241 mg), 3-({2-[(3R)-3-fluoro-1-pyrrolidinyl]ethyl}oxy)benzoic acid D52 (220 mg) and DIPEA (400 mg, 3.09 mmol) in the mixture solvent of NMP (5 ml) and DCM (15 mL) stirred at 20° C. was added EDC (237 mg, 1.236 mmol) and HOBT (220 mg, 1.437 mmol). The reaction mixture was stirred at 20° C. overnight. Then the reaction mixture was washed with water (50 ml) and extracted with DCM (50 ml×3). The combined organic layer was dried with Na$_2$SO$_4$ and concentrated.

The residue was purified via Gilson GX-281.
Instrument: Gilson 281
Mobile Phase: A=0.01% NH$_4$HCO$_3$/H$_2$O, B=MeCN
Flow Rate: 30.0 ml/minute
Column: Shimadzu PRC-ODS 15 μm 19 mm×250 mm Method:

$$B: A = \begin{matrix} 35\%: 65\% \text{ to } 45\%: & 55\% & 0 \text{ to } 7 \text{ minutes} \\ 95\%: 5\% & & 7 \text{ to } 14 \text{ minutes} \end{matrix}$$

Target peak: at 7.5 min

The target peak was collected and concentrated and acidified to be HCl salt of the title compound E47 as a pink solid. LCMS Retention time=1.56 minutes, [M+H]$^+$467 (5 minutes run)

Example E48 (E48)

3-{[2-(3,3-difluoro-1-pyrrolidinyl)ethyl]oxy}-N-[1-(5-methyl-1H-pyrrolo[2,3-d]pyrimidin-4-yl)-4-piperidinyl]benzamide hydrochloride

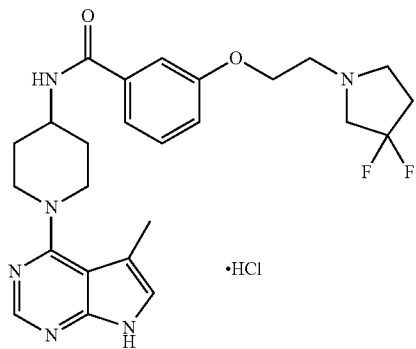 [SMILES: Cc1c[nH]c2ncnc(N3CCC(NC(=O)c4cccc(OCCN5CCC(F)(F)C5)c4)CC3)c12 ; Cl]

To a solution of 3-{[2-(3,3-difluoro-1-pyrrolidinyl)ethyl]oxy}benzoic acid D53 (127 mg), EDC (149 mg, 0.778 mmol) and HOBT (119 mg, 0.778 mmol) in DCM (15 mL) stirred at 25° C. was added a solution of 1-(5-methyl-1H-pyrrolo[2,3-d]pyrimidin-4-yl)-4-piperidinamine D11a (90 mg) and DIEA (201 mg, 1.556 mmol) in N-Methyl-2-pyrrolidone (NMP) (5 mL).

The reaction mixture was stirred at 25° C. overnight. Then the mixture was washed with water (30 ml) and the organic layer was separated. The aqueous layer was extracted with DCM (20 ml×2) and the combined organic layer was concentrated.

The residue was purified by silica gel (DCM/MeOH=100/5, 0.5% TEA) and about 130 mg of the crude product was got. The crude product was purified by preparing HPLC on a Gilson GX-281.
Instrument: Gilson 281
Mobile Phase: A=10M NH$_4$HCO$_3$/H$_2$O, B=MeCN
Flow Rate: 30.0 ml/minute
Column: Shimadzu PRC-ODS 15 μm 19 mm×250 mm
Method:

$$B: A = \begin{matrix} 40\%: 60\% \text{ to } 60\%: & 40\% & 0 \text{ to } 7 \text{ minutes} \\ 95\%: 5\% & & 7 \text{ to } 14 \text{ minutes} \end{matrix}$$

Target peak: at 8.5 min

The target peak was collected and concentrated and acidified to be HCl salt of the title compound E48 in 61.6 mg as a white solid.

Example E49 (E49)

3-({2-[(2R)-2-methyl-1-pyrrolidinyl]ethyl}oxy)-N-[1-(5-methyl-7H-pyrrolo[2,3-d]pyrimidin-4-yl)-4-piperidinyl]benzamide hydrochloride

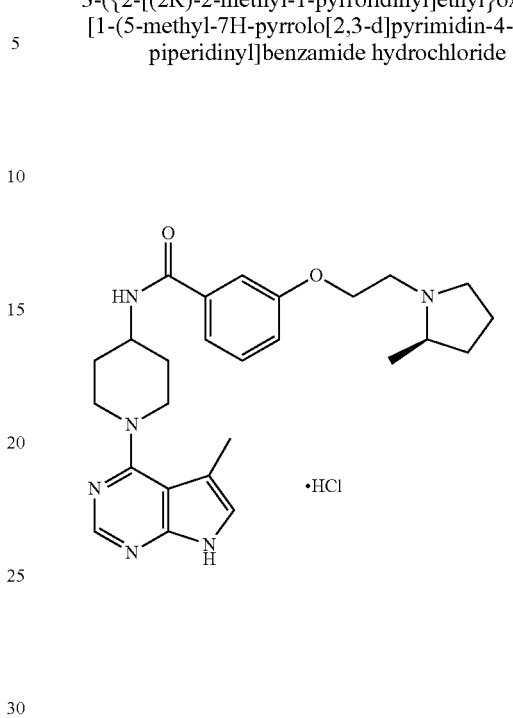

To a solution of 3-({2-[(2R)-2-methyl-1-pyrrolidinyl]ethyl}oxy)benzoic acid D54 (116 mg), HOBT (119 mg, 0.778 mmol) and EDC (149 mg, 0.778 mmol) in Dichloromethane (DCM) (15 mL) stirred at 25° C. was added a solution of 1-(5-methyl-1H-pyrrolo[2,3-d]pyrimidin-4-yl)-4-piperidinamine D11a (90 mg, 0.389 mmol) and DIEA (201 mg, 1.556 mmol) in N-Methyl-2-pyrrolidone (NMP) (5 mL). The reaction mixture was stirred at 25° C. overnight. Then the mixture was washed with water (30 ml) and the organic layer was separated. The aqueous layer was extracted with DCM (20 ml×2) and the combined organic layer was concentrated.

The residue was purified by silica gel (DCM/MeOH=100/5, 0.5% TEA) and 120 mg of the crude product was got. The crude product was purified by preparing HPLC on a Gilson GX-281.
Instrument: Gilson 281
Mobile Phase: A=10M NH$_4$HCO$_3$/H$_2$O, B=MeCN
Flow Rate: 30.0 ml/minute
Column: Shimadzu PRC-ODS 15 μm 19 mm×250 mm
Method:

$$B: A = \begin{matrix} 46\%: 54\% \text{ to } 55\%: & 45\% & 0 \text{ to } 7.2 \text{ minutes} \\ 55\%: 45\% \text{ to } 95\%: & 5\% & 7.2 \text{ to } 7.5 \text{ minutes} \\ 95\%: 5\% & & 7.5 \text{ to } 11.5 \text{ minutes} \end{matrix}$$

The target peak was collected and concentrated and acidified to be HCl salt of the title compound E49 in 78.2 mg as a white solid. LCMS Retention time=1.55 minutes, [M+H]$^+$ 463 (5 minutes run)

Example 50

2-(phenyloxy)-N-[1-(7H-pyrrolo[2,3-d]pyrimidin-4-yl)-4-piperidinyl]acetamide (formate salt)

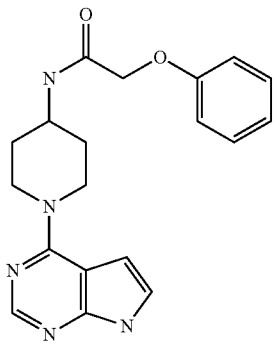 [SMILES: O=C(COc1ccccc1)NC1CCN(c2ncnc3[nH]ccc23)CC1]

Phenyloxy)acetyl chloride (0.033 ml, 0.240 mmol, commercially available from e.g. Sigma-aldrich, or Fluka) in DCM (1.5 ml) was added to a solution of 1-(7H-pyrrolo[2,3-d]pyrimidin-4-yl)-4-piperidinamine D2 (0.043 g, 0.200 mmol) and POL-NMM (0.279 g, 0.600 mmol) in DMF (1.5 ml). The mixture was shaken overnight at room temperature on a mini block. The resulting mixture was washed using DCM DMF (1:1) and the acid chloride left was removed using an NH2 cartridge. Then the solvents were evaporated overnight using the genevac. The crude was finally purified via MDAP using a formic acid method to afford the product E50 in 36 mg. LCMS: [M+H]+352.05@064 min (2 min run) free base.

Example 51

2-phenyl-N-[1-(7H-pyrrolo[2,3-d]pyrimidin-4-yl)-4-piperidinyl]acetamide (formate salt)

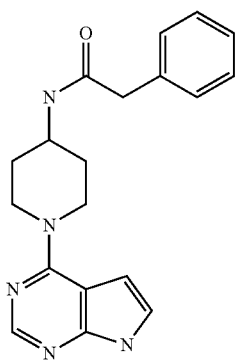 [SMILES: O=C(Cc1ccccc1)NC1CCN(c2ncnc3[nH]ccc23)CC1]

Phenylacetyl chloride (0.037 g, 0.240 mmol, commercially available from e.g sigma-aldrich or fluka) in Dichloromethane (DCM) (1.5 ml) was added to a solution of 1-(7H-pyrrolo[2,3-d]pyrimidin-4-yl)-4-piperidinamine D2 (0.043 g) and POL-NMM (0.279 g, 0.600 mmol) in DMF (1.5 ml). The mixture was shaken overnight at room temperature on a mini block. The resulting mixture was washed using DCM DMF (1:1) and the acid chloride left was removed using an NH2 cartridge. Then the solvents were evaporated overnight using the genevac. The crude was finally purified via MDAP using a formic acid method to obtain the desired product E51 in 24 mg. LCMS [M+H]+336.06@0.62 min (2 min run)

Example 52

Determination of ASK1 Inhibitor Activity

IMAP™ Technology Description

ASK1 activity was measured in an Immobilised Metal Ion Affinity-Based Fluorescence Polarisation (IMAP™ FP) assay (Sportsman R J et al (2004) ASSAY and Drug Development Technologies (2) p205), which measures the degree of phosphorylation of a fluorescently labelled peptide substrate. IMAP™ technology is based on high affinity binding of phosphate at high salt concentrations by immobilized metal ($M^{III}$). The IMAP™ "binding reagent" complexes with phosphate groups on the phosphopeptide generated by the kinase reaction. Binding causes a change in the rate of the molecular motion of the peptide, resulting in an increase in fluorescence polarization (FP) observed. Hence, inhibition of activity is seen as a decrease in FP signal due to a lack of phospho-peptide.

ASK1 Assay Description

The peptide substrate that was used in the ASK1 assay was derived from a 'parent' peptide, RP7140, which was identified by the screening of ASK1 against Molecular Devices Corporation's (MDC) proprietary IMAP™ Substrate Finder kit.

RP7140, which is labelled at the N-terminus with 5FAM, has the following amino acid sequence:

```
                                           (SEQ ID NO: 1)
5FAM-GTFRSSIRRLSTRRR-OH.
```

However, it was noted that RP7140 contained multiple phosphorylation sites and therefore a number of derivative peptides were designed and synthesised which had just single phosphorylation sites. Of these derivative peptides the T2 peptide was identified as the preferential substrate peptide for the assay.

T2 peptide, which is labelled at the N-terminus with 5TAMRA, has the following amino acid sequence and forms part of the present invention:

```
                                           (SEQ ID NO: 2)
5TAMRA-GTFRAAIRRLAARRR-OH.
```

The T2 peptide is not a native substrate for ASK1 and it does not share any homology with MKK7. MKK7 is believed to be the native substrate for ASK1 (Ichijo H et al (2002) Journal of Cellular Physiology 191(1) p95).

ASK1 Assay Conditions and Protocol

The assay was configured to run using the following conditions;

100 μM ATP (0.5K.)

100 nM peptide 3 nM ASK1. The ASK1 used in the assay was full-length human ASK1 (GenBank accession number NP 005914) having a GST tag attached to the N-terminal methionine: the GST tag having the sequence:

(SEQ ID NO: 3)
MAPILGYWKIKGLVQPTRLLLEYLEEKYEEHLYERDEGDKWRNKKFELGLEFPNLPYYIDGDVKLTQ

SMAIIRYIADKHNMLGGCPKERAEISMLEGAVLDIRYGVSRIAYSKDFETLKVDFLSKLPEMLKMFED

RLCHKTYLNGDHVTHPDFMLYDALDVVLYMDPMCLDAFPKLVCFKKRIEAIPQIDKYLKSSKYIAWPL

QGWQATFGGGDHPPKSDLVPRHNQTSLYKKAGS

The assay used the following buffer conditions;
10 mM Tris Cl pH7.2
10 mM $MgCl_2$
0.05% $NaN_3$
0.01% Tween-20
1 mM DTT The IMAP™ reagents were purchased in a kit format from MDC(RP8124).

Experimental
1) 100 nl or 50 nl of the test compound in 100% DMSO were added to low volume 384 or 1536 well plates, respectively. For a single concentration experiment 50 nl of test compound (1.25 mM final assay concentration) was used and for a dose response experiment a 1 in 4 dilution of compound (20 µM top final concentration) was used;
2) 3 µl of ASK1 (3 nM final assay concentration) were added to each well except in the control well to which 3 µl buffer were added;
3) the plates were incubated for 15 minutes at room temperature;
4) 3 µl of substrate (100 nM peptide and 10004 ATP final assay concentration) were added to each well;
5) the plates were incubated for 60 minutes at room temperature;
6) 6 µl of IMAP™ binding reagent were added to each well and spun for 1 minute at 1000 rpm;
7) the plates were incubated for 60 minutes at room temperature;
8) the plates were read on a Perkin Elmer Envision plate reader.

Data Analysis

Data was exported from the Envision in a text file and transferred into Activity Base. A Microsoft Excel template analysis the imported data using the ID Business Solutions (IDBS) XC50v2 curve fitting addin.

The data was normalised to the controls using the following equation to give a percentage inhibition (% I):

(High Control−Sample)/*ABS*(High Control−Low Control)*100

The analysis used the following key settings;
Minimum constrained if less than −20% I or greater than 20% I
Maximum constrained if less than 80% I or greater than 120% I
Slope constrained if less than 0.5 or greater than 2.5

Example 53

Determination of ASK1 Inhibitor Activity

AlphaLISA® Technology Description

ASK1 activity was quantified in an AlphaLISA®[3] assay (Eglen R M et al (2008) Curr Chem Genomics 1 p2) which measures the degree of phosphorylation of a protein substrate (MKK4 or MKK7). AlphaLISA0 technology is based on the binding of a substrate to two types of beads, acceptor and donor. Binding to one bead is through the tag of the substrate protein. Binding of the second bead is through phosphospecific binding of a antibody to the phosphosite of the substrate. This forms a sandwich, with the acceptor and donor beads in close proximity. When the donor beads are excited by light in the 680 nm range, a singlet oxygen is released and causes emission of light from the acceptor in the 620 nm range which can be detected using a suitable plate reader.

ASK1 AlphaLISA0 Assay Description

The ASK1 AlphaLISA0 assays were enabled by binding of full length MKK4 or MKK7 to glutathione donor beads through the use of GST-tags. The phosphorylation site on MKK4 (Thr275) or MKK7 (Ser271/Thr275) is then recognised by a phosphospecific antibody. The phosphospecific antibody is bound to the AlphaLISA® acceptor beads through a Protein-A interaction. Phosphorylation of MKK4 or MKK7 by ASK1 subsequently facilitates the bringing together of the donor and acceptor beads into close proximity whereupon the transfer of the singlet oxygen leads to the generation of the AlphaLISA® signal.

ASK1 AlphaLISA® Reagents, Conditions and Protocol

Human ASK1 (GenBank accession number NP 005914) with an N-terminal 6His-Avi tag (SEQ ID NO: 4)
(MGHHHHHHAGGLNDIFEAQKIEWHETSTSLYKKAGT;

attached to the N terminal methionine.

Rat ASK1 (NCBI protein sequence XP_001073260.1 but (i) which has no lysine at position 604 and (ii) where the residues 959 to 965 are ALSTGSN in place of the corresponding GMWLHGE in the NCBI sequence) and having an N-terminal GST tag and linker attached to the N-terminal methionine of the rat ASK1 sequence, the GST tag and linker having the sequence:

(SEQ ID NO: 5)
MAPILGYWKIKGLVQPTRLLLEYLEEKYEEHLYERDEGDKWRNKKFELGLEFPNLPYYIDGDVKLTQ

SMAIIRYIADKHNMLGGCPKERAEISMLEGAVLDIRYGVSRIAYSKDFETLKVDFLSKLPEMLKMFED

RLCHKTYLNGDHVTHPDFMLYDALDVVLYMDPMCLDAFPKLVCFKKRIEAIPQIDKYLKSSKYIAWPL

QGWQATFGGGDHPPKSDLVPRHNQTSLYKKAGSAAAPFT

Mouse MKK4 (residues 34-397 of GenBank accession number AAB81554) having a GST tag attached to the N-terminal residue, the GST tag having the sequence:

(SEQ ID NO: 6)
MSPILGYWKIKGLVQPTRLLLEYLEEKYEEHLYERDEGDKWRNKKFEL

GLEFPNPLYYIDGDVKLTQSMAIIRYIADKHNMLGGCPKERAEISMLE

GAVLDIRYGVSRIAYSKDFETLKVDFLSKLPEMLHMFEDRLCHKTYLN

GDHVTHPDFMLYDALAVVLYMDPMCLDAFPKLVCFKKRIEAIPQIDKY

LKSSKYIAWPLQGWQATFGGGDHPPKSDLVPRG

Human MKK7 (residues 2 to 419 of GenBank accession number NP_660186 having a GST and a Flag tag attached to the N-terminal residue, the GSK and Flag tag having the sequence:

(SEQ ID NO: 7)
MSPILGYWKIKGLVQPTRLLLEYLEEKYEEHLYERDEGDKWRNKKFEL

GLEFPNPLYYIDGDVKLTQSMAIIRYIADKHNMLGGCPKERAEISMLE

GAVLDIRYGVSRIAYSKDFETLKVDFLSKLPEMLHMFEDRLCHKTYLN

GDHVTHPDFMLYDALAVVLYMDPMCLDAFPKLVCFKKRIEAIPQIDKY

LKSSKYIAWPLQGWQATFGGGDHPPKSDLVPRGSATMDYKDDDDK

Phospho-SEK1/MKK4 (Thr261) antibody (Cell Signalling Technologies product no. 9151) detects endogenous levels of SEK1/MKK4 protein only when phosphorylated at threonine 261. This antibody does not cross-react with the corresponding phosphorylated residues of MEK1, MEK2 or MKK3.

Phospho-MKK7 (Ser171/Thr275) antibody (Cell Signalling Technologies product no. 4171) detects endogenous levels of MKK7 phosphorylated at serine 271 and threonine 275.

ASK1-MKK4

The assay was configured to run using the following conditions;
230 µM ATP ($K_m$)
400 nM MKK4 ($K_m$)
2.5 nM ASK1

ASK1-MKK7

The assay was configured to run using the following conditions;
150 µM ATP ($K_{1n}$)
200 nM MKK4 ($K_m$)
80 pM ASK1

Rat ASK1-MKK7

The assay was configured to run using the following conditions;
150 µM ATP ($K_m$)
200 nM MKK7 ($K_m$)
200 pM rat ASK1

All AlphaLISA assays used the following buffer conditions;
50 mM HEPES pH 7.4
150 mM NaCl
10 mM $MgCl_2$/60 mM EDTA ($MgCl_2$ is used for the enzyme reaction additions, EDTA is used for the quench/bead additions)
1 mM CHAPS
1 mM DTT Experimental
1) 100 nl of test compound (1 in 3 dilution from 20 µM top final concentration) in 100% DMSO was added to low volume 384 well plates
2) 2.5 µl of human ASK1 or rat ASK1 (80 µM/200 µM final concentration, respectively) was added to each well except in the control well to which 2.5 µl buffer were added
3) the plate was incubated for 15 minutes at room temperature
4) 2.5 µl of MKK4 or MKK7 (400 nM or 200 nM final concentration, respectively) were added to the wells
5) the plate was incubated for 60 minutes at room temperature
6) the Protein-A acceptor beads and phospho-specific antibody was incubated for 30 minutes
7) 2.5 µl of Protein-A acceptor beads/phospho-specific antibody mix (5 µg/ml acceptor beads final concentration and 1/400 antibody final dilution) was added to each well
8) the plate was incubated for 30 minutes at room temperature
9) 2.5 µl of GSH donor beads (40 µg/ml acceptor beads final concentration) were added to each well
10) the plate was spun for 1 minute at 1000 rpm
11) the plate was incubated for 60 minutes at room temperature
12) the plate was read on a Perkin Elmer Envision plate reader.

Data Analysis

Data was exported from the Envision plate reader in a text file and analysed in Microsoft Excel using the IDBS XC50v2 curve fitting addin.

The data was normalised to the controls using the following equation to give a percentage inhibition (% I);

(High Control−Sample)/$ABS$(High Control−Low Control)*100

The analysis used the following key settings;
Min constrained if less than −20%1 or greater than 20% I
Max constrained if less than 80%1 or greater than 120% I
Slope constrained if less than 0.5 or greater than 2.5

Compounds of Examples 1 to 51 were tested according to the method of example 52 or the method of example 53. All compounds gave pIC50 values from 5.5 to 8.6 at the human ASK1 kinase.

The compound 4-(1-pyrrolidinyl)-N-[1-(1H-pyrrolo[2,3-d]pyrimidin-4-yl)-4-piperidinyl]benzamide gives a pIC50 value of 4.6.

Example 54

ASK1 Kinase Dead Knock-in (ki) Mice have a Protective Phenotype in the FCA-Induced Model of Mechanical Hypersensitivity To test the role of ASK1 in pain responses, the behaviour of mice homozygous for an ASK1 dead allele (lysine at amino acid 716 substituted with arginine) were tested in pain models. Hypersensitivity to mechanical stimulus following acute inflammation was tested using the established model of intraplantar Freund's Complete Adjuvant (FCA)-induced inflammation Animals were tested for changes in mechanical hypersensitivity using an analgesymeter (mean paw withdrawal latency) at 1, 5, 9 and 14 days following FCA injection or weight bearing 24 hours after FCA injection. Results were expressed as mean ipsilateral/contralateral ratio for each test day and analysed using 2-way analysis of variance in Statistica with genotype and days post FCA being used as independent variables. Follow up analysis was carried out using Duncan's test. The results are shown in FIG. 1.

Following intraplantar FCA injection, analysis of the ipsilateral/contralateral weight bearing ratio or paw withdrawal thresholds revealed a significant effect of genotype between ASK1$^{ki/ki}$ and WT mice. ASK1$^{ki/ki}$ mice, homozygous for a loss of function ASK1 allele, failed to develop significant hypersensitivity at any time after FCA injection, whereas the WT mice displayed a significant reduction in ipsilateral/contralateral ratios. These data are consistent with the hypothesis that ASK1 may play a role in pain sensitivity.

Example 55

A Small Molecule Inhibitor of ASK1 Reverses Inflammatory Mechanical Hypersensitivity In order to replicate the phenotype observed with the ASK1 knock-in mice from example 54, but using a pharmacological tool, a small molecule inhibitor of ASK1 was used. The anti-hyperalgesic properties of N-[1-(5-methyl-1H-pyrrolo[2,3-d]pyrimidin-4-yl)-4-piperidinyl]benzamide (the compound of example 17) was trialled using the established model of intraplantar Freund's Complete Adjuvant (FCA)-induced inflammation. 24 hours after injection of FCA the compound was dosed orally and the effect on mechanical hypersensitivity assessed using weightbearing. The results are shown in FIG. 2.
N-[1-(5-methyl-1H-pyrrolo[2,3-d]pyrimidin-4-yl)-4-piperidinyl]benzamide was found to partially reverse the inflammatory mechanical hypersensitivity caused by FCA at 30 mg/kg. This data is consistent with the hypothesis that ASK1 may play a role in inflammatory mechanical hypersensitivity.

Example 56

A Small Molecule ASK1 Inhibitor Significantly Decreases Chronic Constriction Injury Induced Mechanical Allodynia In order to establish if an ASK1 inhibitor is able to reverse hypersensitivity caused by neuronal injury in addition to inflammatory hypersensitivity, N-[1-(5-methyl-1H-pyrrolo[2,3-d]pyrimidin-4-yl)-4-piperidinyl]benzamide was trialled in the rat chronic constriction injury (CCI) model of neuropathic pain. The results are shown in FIG. 3.
N-[1-(5-methyl-1H-pyrrolo[2,3-d]pyrimidin-4-yl)-4-piperidinyl]benzamide partially reversed the mechanical allodynia caused by the nerve injury in the CCI model. This data suggests that ASK1 inhibitors may have therapeutic potential in neuropathic, in addition to inflammatory, pain states.

BRIEF EXPLANATION OF THE FIGURES

FIG. 1. Delayed mechanical hypersensitivity of ASK1$^{ki/ki}$ mice following FCA induced inflammation. Animals were tested for changes in mechanical hypersensitivity after FCA injection (30 µL, 1 mg/mL) using either: (FIG. 1a WT vs Baseline *$P<0.001$.

SEQUENCE LISTING

Figure 1A:
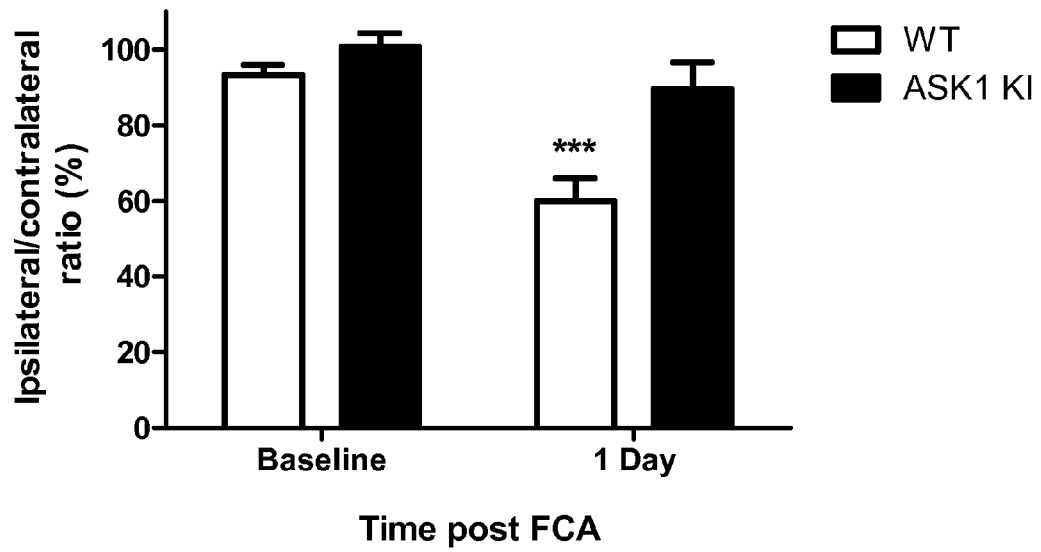
(FIG. 1a) weight bearing at 24 h in female mice, (n=12 per group) or (FIG. 1b) paw withdrawal latency average at 1, 5, 9 and 14 days following FCA injection in male mice (n=12 ASK1$^{ki/ki}$ mice and n=12 wild-type littermates).
Figure 1B:
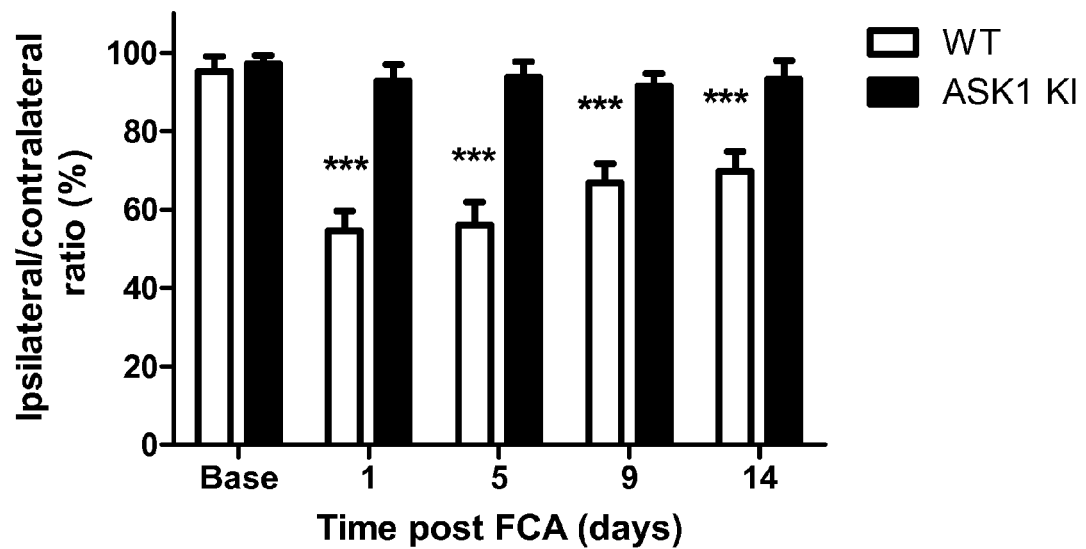
FIG. 1b *$P<0.001$ at day 1, 5, 9 and 14 for WT versus Baseline).
Figure 2:
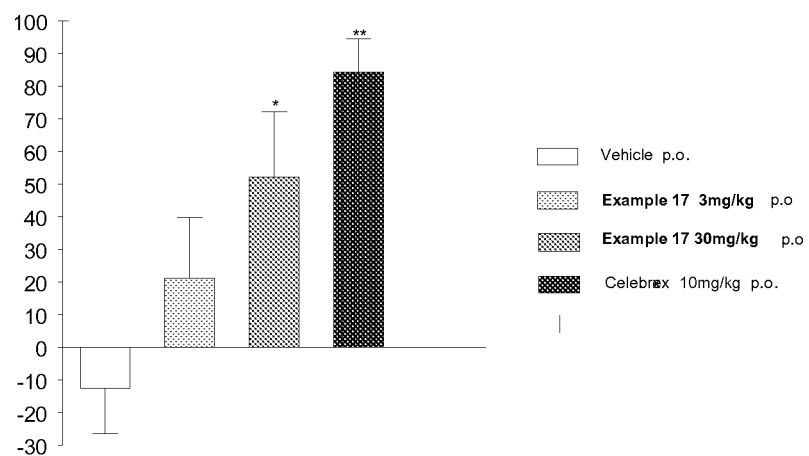
FIG. 2 A small molecule inhibitor of ASK1, N-[1-(5-methyl-1H-pyrrolo[2,3-d]pyrimidin-4-yl)-4-piperidinyl]benzamide, reverses inflammatory mechanical hypersensitivity. 24 hours after intraplantar injection of FCA (100 µL), rats (n=7 per group) were dosed with 1% methylcellulose vehicle, N-[1-(5-methyl-1H-pyrrolo[2,3-d]pyrimidin-4-yl)-4-piperidinyl]benzamide (3 mg/kg po, 30 mg/kg po) or celebrex (10 mg/kg po) and 1 hour later mechanical hypersensitivity was measured by weightbearing. (*$P=0.013$, **$P=0.0004$; statistical significance was determined using ANOVA followed by Fisher's LSD posthoc test comparing vehicle to response).
Figure 3:
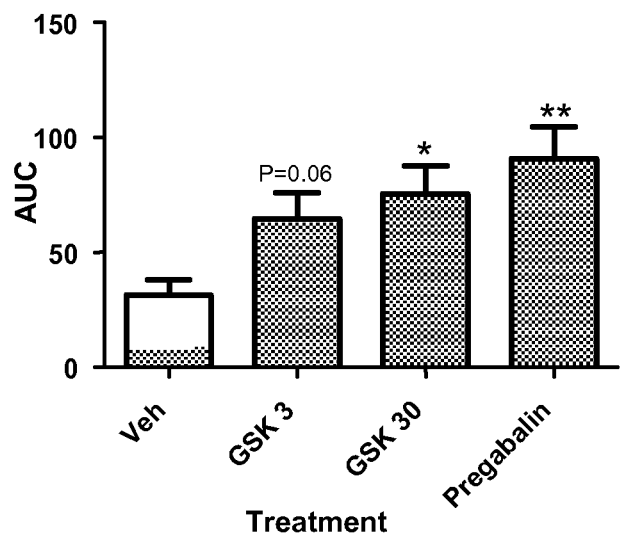
FIG. 3. N-[1-(5-methyl-1H-pyrrolo[2,3-d]pyrimidin-4-yl)-4-piperidinyl]benzamide partially reverses mechanical allodynia in the CCI model of nerve injury. Chronic constriction injury was performed on rats. Baseline readings of mechanical thresholds were taken on days −1 and 19 post surgery. Randomized groups of rats with allodynia (n=9-10) were dosed from day 20 to day 27 with either vehicle, N-[1-(5-methyl-1H-pyrrolo[2,3-d]pyrimidin-4-yl)-4-piperidinyl]benzamide (3 mg/kg po, 30 mg/kg po bid) or pregabalin (30 mg/kg pop bid). Mechanical allodynia was measured using Von Frey hairs 1 hour post morning dose on days 22, 25 and 27. The hypersensitivity observed was expressed as the area under the curve in grams·days (AUC), calculated using the Trapezoidal rule. (*$p<0.05$, **$p<0.01$, statistical significance was determined using one way ANOVA followed by Fisher's LSD posthoc test comparing to vehicle response).

```
<160> NUMBER OF SEQ ID NOS: 7

<210> SEQ ID NO 1
<211> LENGTH: 15
<212> TYPE: PRT
<213> ORGANISM: Artificial
<220> FEATURE:
<223> OTHER INFORMATION: Synthetic Peptide

<400> SEQUENCE: 1

Gly Thr Phe Arg Ser Ser Ile Arg Arg Leu Ser Thr Arg Arg Arg
1               5                   10                  15

<210> SEQ ID NO 2
<211> LENGTH: 15
<212> TYPE: PRT
<213> ORGANISM: Artificial
<220> FEATURE:
<223> OTHER INFORMATION: Synthetic Peptide
```

```
<400> SEQUENCE: 2

Gly Thr Phe Arg Ala Ala Ile Arg Arg Leu Ala Ala Arg Arg Arg
1               5                  10                  15

<210> SEQ ID NO 3
<211> LENGTH: 236
<212> TYPE: PRT
<213> ORGANISM: Human

<400> SEQUENCE: 3

Met Ala Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

His Asn Gln Thr Ser Leu Tyr Lys Lys Ala Gly Ser
225                 230                 235

<210> SEQ ID NO 4
<211> LENGTH: 36
<212> TYPE: PRT
<213> ORGANISM: Artificial
<220> FEATURE:
<223> OTHER INFORMATION: Synthetic Peptide

<400> SEQUENCE: 4

Met Gly His His His His His His Ala Gly Gly Leu Asn Asp Ile Phe
1               5                   10                  15

Glu Ala Gln Lys Ile Glu Trp His Glu Thr Ser Thr Ser Leu Tyr Lys
            20                  25                  30

Lys Ala Gly Thr
        35

<210> SEQ ID NO 5
```

```
<211> LENGTH: 242
<212> TYPE: PRT
<213> ORGANISM: Rat

<400> SEQUENCE: 5

Met Ala Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

His Asn Gln Thr Ser Leu Tyr Lys Lys Ala Gly Ser Ala Ala Ala Pro
225                 230                 235                 240

Phe Thr

<210> SEQ ID NO 6
<211> LENGTH: 225
<212> TYPE: PRT
<213> ORGANISM: Mouse

<400> SEQUENCE: 6

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Pro Leu Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95
```

```
Gly Ala Val Leu Asp Ile Arg Tyr Gly Val Ser Arg Ile Ala Tyr Ser
            100                 105                 110
Lys Asp Phe Glu Thr Leu Lys Val Asp Phe Leu Ser Lys Leu Pro Glu
        115                 120                 125
Met Leu His Met Phe Glu Asp Arg Leu Cys His Lys Thr Tyr Leu Asn
    130                 135                 140
Gly Asp His Val Thr His Pro Asp Phe Met Leu Tyr Asp Ala Leu Ala
145                 150                 155                 160
Val Val Leu Tyr Met Asp Pro Met Cys Leu Asp Ala Phe Pro Lys Leu
                165                 170                 175
Val Cys Phe Lys Lys Arg Ile Glu Ala Ile Pro Gln Ile Asp Lys Tyr
            180                 185                 190
Leu Lys Ser Ser Lys Tyr Ile Ala Trp Pro Leu Gln Gly Trp Gln Ala
        195                 200                 205
Thr Phe Gly Gly Gly Asp His Pro Pro Lys Ser Asp Leu Val Pro Arg
    210                 215                 220
Gly
225

<210> SEQ ID NO 7
<211> LENGTH: 237
<212> TYPE: PRT
<213> ORGANISM: Human

<400> SEQUENCE: 7

Met Ser Pro Ile Leu Gly Tyr Trp Lys Ile Lys Gly Leu Val Gln Pro
1               5                   10                  15
Thr Arg Leu Leu Leu Glu Tyr Leu Glu Glu Lys Tyr Glu Glu His Leu
            20                  25                  30
Tyr Glu Arg Asp Glu Gly Asp Lys Trp Arg Asn Lys Lys Phe Glu Leu
        35                  40                  45
Gly Leu Glu Phe Pro Asn Pro Leu Tyr Tyr Ile Asp Gly Asp Val Lys
    50                  55                  60
Leu Thr Gln Ser Met Ala Ile Ile Arg Tyr Ile Ala Asp Lys His Asn
65                  70                  75                  80
Met Leu Gly Gly Cys Pro Lys Glu Arg Ala Glu Ile Ser Met Leu Glu
                85                  90                  95
Gly Ala Val Leu Asp Ile Arg Tyr Gly Val Ser Arg Ile Ala Tyr Ser
            100                 105                 110
Lys Asp Phe Glu Thr Leu Lys Val Asp Phe Leu Ser Lys Leu Pro Glu
        115                 120                 125
Met Leu His Met Phe Glu Asp Arg Leu Cys His Lys Thr Tyr Leu Asn
    130                 135                 140
Gly Asp His Val Thr His Pro Asp Phe Met Leu Tyr Asp Ala Leu Ala
145                 150                 155                 160
Val Val Leu Tyr Met Asp Pro Met Cys Leu Asp Ala Phe Pro Lys Leu
                165                 170                 175
Val Cys Phe Lys Lys Arg Ile Glu Ala Ile Pro Gln Ile Asp Lys Tyr
            180                 185                 190
Leu Lys Ser Ser Lys Tyr Ile Ala Trp Pro Leu Gln Gly Trp Gln Ala
        195                 200                 205
Thr Phe Gly Gly Gly Asp His Pro Pro Lys Ser Asp Leu Val Pro Arg
    210                 215                 220
```

```
Gly Ser Ala Thr Met Asp Tyr Lys Asp Asp Asp Lys
225                 230              235
```

The invention claimed is:
1. A compound of formula (I)

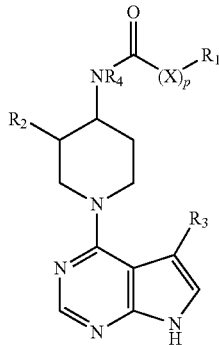

where
X is $(CH_2)_m$ or $CH_2O$, where m is 1 or 2;
p is 0 or 1;
$R_1$ is phenyl or a 5 or 6 membered heteroaryl group selected from the group consisting of imidazolyl, isoxazolyl, pyridinyl, pyridazinyl or pyrimidinyl, which phenyl or heteroaryl group is optionally substituted with 1 or 2 substituents selected from the group consisting of $(C_{1-4})$alkyl, $(C_{1-4})$alkoxy, halo, $(CH_2)_nNR_5R_6$ where $R_5$ and $R_6$ are independently H or $(C_{1-4})$alkyl and n is 0 or 1, pyrrolidinyl, morpholinyl, piperidinyl, pyrrolidin($C_{1-4}$) alkyl, morpholin($C_{1-4}$)alkyl, piperidin($C_{1-4}$)alkyl, pyrrolidin($C_{1-4}$)alkoxy, morpholin($C_{1-4}$)alkoxy, piperidin ($C_{1-4}$)alkoxy wherein said pyrrolidinyl, morpholinyl or piperidinyl groups are optionally substituted with halo or $(C_{1-4})$alkyl, with the proviso that when $R_1$ is phenyl or a 6 membered heteroaryl group, which phenyl or 6 membered heteroaryl group has a substitutent on the atom at the para position, said substituent is selected from the group consisting of methyl, ethyl, isopropyl, methoxy, halo or $(CH_2)_nNR_5R_6$ where $R_5$ and $R_6$ are methyl;
$R_2$ is H, methoxy, ethoxy or $CH_2OCH_3$;
$R_3$ is H, $(C_{1-4})$alkyl, $(C_{2-4})$alkenyl, halo, cyano, furanyl or pyrazolyl, which pyrazolyl is optionally substituted with 1 methyl group;
$R_4$ is H or $(C_{1-4})$alkyl;
or a pharmaceutically acceptable salt thereof.
2. A compound according to claim 1 where p is 0, or a pharmaceutically acceptable salt thereof.
3. A compound according to claim 1 where p is 1, or a pharmaceutically acceptable salt thereof.
4. A compound according to claim 3 where X is methyl or methoxy, or a pharmaceutically acceptable salt thereof.
5. A compound according to claim 1 where $R_2$ is H, or a pharmaceutically acceptable salt thereof.
6. A compound according to claim 1 where $R_3$ is methyl, or a pharmaceutically acceptable salt thereof.
7. A compound according to claim 1 where $R_4$ is H, or a pharmaceutically acceptable salt thereof.
8. A compound according to claim 1 where $R_1$ is unsubstituted phenyl or an unsubstituted 5 or 6 membered heteroaryl group selected from the group consisting of imidazolyl, isoxazolyl, pyridinyl, pyridazinyl or pyrimidinyl, or a pharmaceutically acceptable salt thereof.
9. A compound according to claim 8 where $R_1$ is unsubstituted phenyl.
10. A compound according to claim 1 where $R_1$ is phenyl substituted with $(C_{1-4})$alkyl or $(C_{1-4})$alkoxy.
11. A compound according claim 1 where $R_1$ is pyridinyl substituted with $(C_{1-4})$alkyl or $(C_{1-4})$alkoxy, or a pharmaceutically acceptable salt thereof.
12. A compound according to claim 1 where $R_1$ is isoxazolyl substituted with 1 or 2 $(C_{1-4})$alkyl groups, or a pharmaceutically acceptable salt thereof.
13. A compound according to claim 1 where $R_1$ is imidazolyl substituted with 1 or 2 $(C_{1-4})$alkyl groups, or a pharmaceutically acceptable salt thereof.
14. A compound according to claim 1 which is selected from the group consisting of:
N-[1-(7H-Pyrrolo[2,3-d]pyrimidin-4-yl)-4-piperidinyl] benzamide;
3-(Methyloxy)-N-[1-(1H-pyrrolo[2,3-d]pyrimidin-4-yl)-4-piperidinyl]benzamide;
3-(Dimethylamino)-N-[1-(1H-pyrrolo[2,3-d]pyrimidin-4-yl)-4-piperidinyl]benzamide;
4-(Dimethylamino)-N-[1-(1H-pyrrolo[2,3-d]pyrimidin-4-yl)-4-piperidinyl]benzamide;
2-(Dimethylamino)-N-[1-(1H-pyrrolo[2,3-d]pyrimidin-4-yl)-4-piperidinyl]benzamide;
3-[(Dimethylamino)methyl]-N-[1-(1H-pyrrolo[2,3-d]pyrimidin-4-yl)-4-piperidinyl]benzamide;
3-(1-Pyrrolidinyl)-N-[1-(1H-pyrrolo[2,3-d]pyrimidin-4-yl)-4-piperidinyl]benzamide;
3-(4-Morpholinyl)-N-[1-(1H-pyrrolo[2,3-d]pyrimidin-4-yl)-4-piperidinyl]benzamide;
N-[1-(1H-Pyrrolo[2,3-d]pyrimidin-4-yl)-4-piperidinyl]-2-pyridinecarboxamide;
N-[1-(1H-Pyrrolo[2,3-d]pyrimidin-4-yl)-4-piperidinyl]-3-pyridinecarboxamide;
N-[1-(1H-Pyrrolo[2,3-d]pyrimidin-4-yl)-4-piperidinyl]-4-pyridinecarboxamide;
2-Methyl-N-[1-(1H-pyrrolo[2,3-d]pyrimidin-4-yl)-4-piperidinyl]-4-pyridinecarboxamide;
N-[1-(1H-Pyrrolo[2,3-d]pyrimidin-4-yl)-4-piperidinyl]-4-pyridazinecarboxamide;
N-[1-(1H-Pyrrolo[2,3-d]pyrimidin-4-yl)-4-piperidinyl]-5-pyrimidinecarboxamide;
2-(Methyloxy)-N-[1-(1H-pyrrolo[2,3-d]pyrimidin-4-yl)-4-piperidinyl]-4-pyridinecarboxamide;
5-Methyl-N-[1-(1H-pyrrolo[2,3-d]pyrimidin-4-yl)-4-piperidinyl]-3-isoxazolecarboxamide;
N-[1-(5-Methyl-1H-pyrrolo[2,3-d]pyrimidin-4-yl)-4-piperidinyl]benzamide;
N-[1-(5-Ethyl-1H-pyrrolo[2,3-d]pyrimidin-4-yl)-4-piperidinyl]benzamide;
N-{1-[5-(1-Methylethenyl)-1H-pyrrolo[2,3-d]pyrimidin-4-yl]-4-piperidinyl}benzamide;
N-{1-[5-(1-Methylethyl)-1H-pyrrolo[2,3-d]pyrimidin-4-yl]-4-piperidinyl}benzamide;
N-[1-(5-Methyl-1H-pyrrolo[2,3-d]pyrimidin-4-yl)-4-piperidinyl]-2-pyridinecarboxamide;

6-Methyl-N-[1-(5-methyl-1H-pyrrolo[2,3-d]pyrimidin-4-yl)-4-piperidinyl]-3-pyridinecarboxamide;
2-(Methyloxy)-N-[1-(5-methyl-1H-pyrrolo[2,3-d]pyrimidin-4-yl)-4-piperidinyl]-4-pyridinecarboxamide;
3-(Methyloxy)-N-[1-(5-methyl-1H-pyrrolo[2,3-d]pyrimidin-4-yl)-4-piperidinyl]benzamide;
2-Methyl-N-[1-(5-methyl-7H-pyrrolo[2,3-d]pyrimidin-4-yl)-4-piperidinyl]-4-pyridinecarboxamide;
2-Methyl-N-[1-(5-methyl-7H-pyrrolo[2,3-d]pyrimidin-4-yl)-4-piperidinyl]benzamide;
N-[1-(5-methyl-7H-pyrrolo[2,3-d]pyrimidin-4-yl)-4-piperidinyl]-4-pyridinecarboxamide;
3,5-dimethyl-N-[1-(5-methyl-7H-pyrrolo[2,3-d]pyrimidin-4-yl)-4-piperidinyl]-4-isoxazolecarboxamide;
N-[1-(5-bromo-7H-pyrrolo[2,3-d]pyrimidin-4-yl)-4-piperidinyl]benzamide;
N-methyl-N-[1-(7H-pyrrolo[2,3-d]pyrimidin-4-yl)-4-piperidinyl]benzamide;
2,6-dimethyl-N-[1-(5-methyl-7H-pyrrolo[2,3-d]pyrimidin-4-yl)-4-piperidinyl]benzamide;
N-methyl-N-[1-(5-methyl-7H-pyrrolo[2,3-d]pyrimidin-4-yl)-4-piperidinyl]benzamide;
1-methyl-N-[1-(5-methyl-7H-pyrrolo[2,3-d]pyrimidin-4-yl)-4-piperidinyl]-1H-imidazole-5-carboxamide;
N-[3-(methyloxy)-1-(5-methyl-7H-pyrrolo[2,3-d]pyrimidin-4-yl)-4-piperidinyl]benzamide;
N-methyl-N-[1-(5-methyl-7H-pyrrolo[2,3-d]pyrimidin-4-yl)-4-piperidinyl]-4-pyridinecarboxamide;
N-[1-(5-bromo-7H-pyrrolo[2,3-d]pyrimidin-4-yl)-4-piperidinyl]-N-methyl-4-pyridinecarboxamide;
N-{1-[5-(1-methyl-1H-pyrazol-4-yl)-1H-pyrrolo[2,3-d]pyrimidin-4-yl]-4-piperidinyl}benzamide;
N-{1-[5-(3-furanyl)-1H-pyrrolo[2,3-d]pyrimidin-4-yl]-4-piperidinyl}benzamide;
N-[3-[(methyloxy)methyl]-1-(5-methyl-7H-pyrrolo[2,3-d]pyrimidin-4-yl)-4-piperidinyl]benzamide;
N-[1-(5-methyl-7H-pyrrolo[2,3-d]pyrimidin-4-yl)-4-piperidinyl]-3-{[2-(1-pyrrolidinyl)ethyl]oxy}benzamide;
N-[1-(5-chloro-1H-pyrrolo[2,3-d]pyrimidin-4-yl)-4-piperidinyl]benzamide;
N-[1-(5-cyano-1H-pyrrolo[2,3-d]pyrimidin-4-yl)-4-piperidinyl]benzamide;
N-[1-(5-methyl-1H-pyrrolo[2,3-d]pyrimidin-4-yl)-4-piperidinyl]-3-{[2-(4-morpholinyl)ethyl]oxy}benzamide;
3-({2-[(3R)-3-fluoro-1-pyrrolidinyl]ethyl}oxy)-N-[1-(5-methyl-1H-pyrrolo[2,3-d]pyrimidin-4-yl)-4-piperidinyl]benzamide;
3-{[2-(3,3-difluoro-1-pyrrolidinyl)ethyl]oxy}-N-[1-(5-methyl-1H-pyrrolo[2,3-d]pyrimidin-4-yl)-4-piperidinyl]benzamide;
3-({2-[(2R)-2-methyl-1-pyrrolidinyl]ethyl}oxy)-N-[1-(5-methyl-7H-pyrrolo[2,3-d]pyrimidin-4-yl)-4-piperidinyl]benzamide;
2-(phenyloxy)-N-[1-(7H-pyrrolo[2,3-d]pyrimidin-4-yl)-4-piperidinyl]acetamide; and
2-phenyl-N-[1-(7H-pyrrolo[2,3-d]pyrimidin-4-yl)-4-piperidinyl]acetamide,
or a pharmaceutically acceptable salt thereof.

15. The compound according to claim 14 which is N-[1-(5-Methyl-1H-pyrrolo[2,3-d]pyrimidin-4-yl)-4-piperidinyl]benzamide or a pharmaceutically acceptable salt thereof.

16. A pharmaceutical composition comprising a) the compound as defined in claim 1, or a pharmaceutically acceptable salt thereof, and b) a pharmaceutically acceptable carrier.

17. A method of treating rheumatoid arthritis, which comprises administering to a subject in need thereof an effective amount of a compound as defined in claim 1, or a pharmaceutically acceptable salt thereof.

\* \* \* \* \*